(12) United States Patent
Gollner et al.

(10) Patent No.: US 10,138,251 B2
(45) Date of Patent: Nov. 27, 2018

(54) SPIRO[3H-INDOLE-3,2'-PYRROLIDIN]-2(1H)-ONE COMPOUNDS AND DERIVATIVES AS MDM2-P53 INHIBITORS

(71) Applicant: Boehringer Ingelheim International GmbH, Ingelheim am Rhein (DE)

(72) Inventors: Andreas Gollner, Vienna (AT); Christiane Kofink, Perchtoldsdorf (AT); Juergen Ramharter, Vienna (AT); Harald Weinstabl, Vienna (AT); Tobias Wunberg, Hinterbruehl (AT)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 0 days.

(21) Appl. No.: 14/683,173

(22) Filed: Apr. 10, 2015

(65) Prior Publication Data
US 2015/0291611 A1    Oct. 15, 2015

(30) Foreign Application Priority Data
Apr. 11, 2014   (EP) ..................................... 14164388

(51) Int. Cl.
| | |
|---|---|
| *C07D 487/20* | (2006.01) |
| *A61K 31/407* | (2006.01) |
| *C07D 471/22* | (2006.01) |
| *A61K 31/437* | (2006.01) |
| *C07D 487/10* | (2006.01) |
| *A61K 45/06* | (2006.01) |
| *A61K 31/4439* | (2006.01) |

(52) U.S. Cl.
CPC .......... *C07D 487/20* (2013.01); *A61K 31/407* (2013.01); *A61K 31/437* (2013.01); *A61K 31/4439* (2013.01); *A61K 45/06* (2013.01); *C07D 471/22* (2013.01); *C07D 487/10* (2013.01)

(58) Field of Classification Search
CPC .. C07D 403/10; C07D 209/54; C07D 209/96; C07D 487/20; C07D 471/22; A61K 31/407; A61K 31/437
USPC .......................... 548/410, 411; 514/409, 278
See application file for complete search history.

(56) References Cited

U.S. PATENT DOCUMENTS

| | | |
|---|---|---|
| 8,119,623 B2 | 2/2012 | Burdack et al. |
| 9,045,414 B2 | 6/2015 | Burdack et al. |
| 2010/0075949 A1 | 3/2010 | Burdack et al. |
| 2012/0071499 A1 | 3/2012 | Chu et al. |
| 2012/0122839 A1 | 5/2012 | Burdack et al. |
| 2016/0000764 A1 | 1/2016 | Weinstabl et al. |
| 2016/0052938 A1 | 2/2016 | Ramharter et al. |
| 2017/0174695 A1 | 6/2017 | Gollner et al. |
| 2017/0247394 A1 | 8/2017 | Ramharter et al. |

FOREIGN PATENT DOCUMENTS

| | | |
|---|---|---|
| CN | 103910746 A | 7/2014 |
| WO | 9912964 A1 | 3/1999 |
| WO | 2012038307 A1 | 3/2012 |
| WO | 2012116989 A1 | 9/2012 |
| WO | 2015155332 A1 | 10/2015 |
| WO | 2016027195 A1 | 2/2016 |

OTHER PUBLICATIONS

Ke Ding et al, 2006, Structure based design of Spiro-oxoindoles.*
Chen, G. et al., "Spiro[pyrrolidine-2,3'-oxindole] derivatives synthesized by novel regionselective 1,3-dipolar cycloadditions." Molecular Diversity, 2011, vol. 16, No. 1, pp. 151-156.
European Search Report for EP 14175620.5 dated Aug. 8, 2014.
International Search Report and Written Opinion for PCT/EP2015/057839 dated May 15, 2015.
Krzysztof, A. et al., "Mdm2 and MdmX inhibitors for the treatment of cancer: a petent review (2011-present)." Expert Opinion on Therapeutic Patents, 2013, vol. 23, No. 4, pp. 425-448.
Abstract in English for NPL: Li, B. et al., "Molecular Docking, QSAR and Molecular Dynamics Simulation on Spiro-oxindoles as MDM2 Inhibitors." Acta Chimica Sinica, 2013, vol. 71, No. 10, p. 1396.
International Search Report and Written Opinion for PCT/EP2015/069174 dated Sep. 22, 2015.
Li, B. et al., "Molecular Docking, QSAR and Molecular Dynamics Simulation on Spiro-oxindoles as MDM2 Inhibitors." Acta Chimica Sinica, 2013, vol. 71, No. 10, pp. 1396-1403.
Marx, M. et al., "Synthetic Design for Combinatorial Chemistry. Solution and Polymer-Supported Synthesis of Polycyclic Lactams by Intramolecular Cyclization of Azomethine Ylides." Journal of the American Chemical Society, 1997, vol. 119, No. 26, pp. 6153-6167.

(Continued)

*Primary Examiner* — Rita J Desai
(74) *Attorney, Agent, or Firm* — Edouard G. Lebel

(57) ABSTRACT

The present invention encompasses compounds of formula (I)

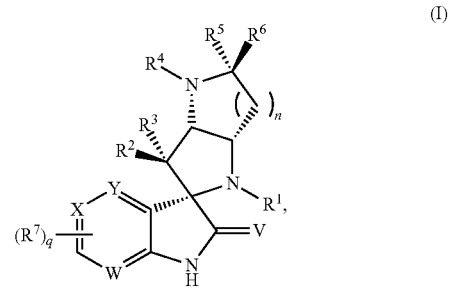

wherein the groups $R^1$ to $R^7$, V, W, X, Y, n and q are defined herein, their use as inhibitors of MDM2-p53 interaction, pharmaceutical compositions which contain compounds of this kind, their use as medicaments, especially as agents for treatment and/or prevention of oncological diseases and synthetic intermediates.

12 Claims, No Drawings

(56) References Cited

OTHER PUBLICATIONS

International Search Report and Written Opinion for corresponding application PCT/EP2016/074008, dated Nov. 3, 2016.
Tisato, MDM2/X inhibitors under clinical evaluation: perpspectives for the mamagement of hematological malignancies and pediatric cancer, Journal of Hematology and Oncology, 2017, vol. 10, p. 1-17.
Kojima, Pharmacological activation of wild-type p53 in the therapy of leukemia, Exp. Hematol. 2016, p. 791-798.
Cecil Textbook of Medicine, edited by Bennet, J.C., 20th Edition, vol. 1, 1004-1010, 1996.
Freshney, Culture of Animal Cells, A Manual of Basic Technique, Liss, Inc., 1983, p. 4.
Dermer, Another Anniversary for the war on Cancer, Bio/Technology, 1994, vol. 12, p. 320-328.
Golub, Molecular Classification of Cancer: Class Discovery and Class Prediction by Gene Expression Monitoring, Science, vol. 286, 1999, p. 531-537.
U.S. Appl. No. 14/790,032, filed Jul. 2, 2015, Harald Weinstabl.
U.S. Appl. No. 14/683,173, filed Apr. 10, 2015, Andreas Gollner.
U.S. Appl. No. 61/096,964, filed Sep. 15, 2008, Christoph Burdack.
U.S. Appl. No. 12/560,051, filed Sep. 15, 2009, Christoph Burdack.
U.S. Appl. No. 13/351,914, filed Jan. 17, 2012, Christoph Burdack.
U.S. Appl. No. 14/831,241, filed Aug. 20, 2015, Juergen Ramharter.
U.S. Appl. No. 15/503,754, filed Feb. 14, 2017, Juergen Ramharter.
U.S. Appl. No. 15/287,958, filed Oct. 7, 2016, Andreas Gollner.
U.S. Appl. No. 16/005,316, filed Jun. 11, 2018. Inventor: Andreas Gollner.
U.S. Appl. No. 16/003,232, filed Jun. 8, 2018. Inventor: Andreas Gollner.
Chemical Abstracts Service, 2006, Accession No. 897585-13-6.
Chemical Abstracts Service, 2006, Accession No. 897585-15-8.
Chemical Abstracts Service, 2006, Accession No. 897585-17-0.
Dandia, Reaction of Indole-2,3-Diones with 3-aminopropanol, Organic Preparations and Procedures, International, the New Journal for Organic Synthesis, 2003, vol. 35, No. 4, p. 433-438.
International Search Report and Written Opinion for corresponding application PCT/EP2015/069174, dated Sep. 22, 2015.
Waite, Reductive Amination of Substituted Indole-2,3-diones, J. Chem. Soc, 1970. p. 550-552.
Zak, Krzysztof et al. Mdm2 and MdmX inhibitors for the treatment of cancer: a patent review (2011-present), (2013) Expert Opinion on Therapeutic Patents, 23:4, 425-448.

* cited by examiner

SPIRO[3H-INDOLE-3,2'-PYRROLIDIN]-2(1H)-ONE COMPOUNDS AND DERIVATIVES AS MDM2-P53 INHIBITORS

The present invention relates to new spiro[3H-indole-3,2'-pyrrolidin]-2(1H)-one compounds and derivatives, and their use as inhibitors of MDM2-p53 interaction, pharmaceutical compositions which contain compounds of this kind, their use as medicaments, especially as agents for treatment and/or prevention of oncological diseases and synthetic intermediates.

BACKGROUND OF THE INVENTION

The tumor suppressor protein p53 is a sequence specific transcription factor and plays a central role in the regulation of several cellular processes, including cell cycle and growth arrest, apoptosis, DNA repair, senescence, angiogenesis, and innate immunity. The Mouse Double Minute 2 (MDM2) protein (or its human homolog also known as HDM2) acts to down-regulate p53 activity in an auto-regulatory manner, and under normal cellular conditions (absence of stress), the MDM2 protein serves to maintain p53 activity at low levels. MDM2 directly inhibits the transactivation function of p53, exports p53 out of the nucleus, and promotes proteasome-mediated degradation of p53 through its E3 ubiquitin ligase activity.

Deregulation of the MDM2/p53 balance by overexpression of MDM2 or by p53 mutation or loss leads to malignant transformation of normal cells. Presently p53 is known to play a key role in practically all types of human cancers, and the mutation or loss of the p53 gene can be identified in more than 50% of all human cancers worldwide. Analysis of 28 different types of human cancers in nearly 4,000 human tumor samples showed that MDM2 is amplified in 7% of human cancers and that MDM2 overexpression by amplification and p53 mutations are largely mutually exclusive (Momand et al., Nucleic Acid Res (1998) 26:3453-3459).

Because of the powerful tumor suppressor function of p53, reactivation of p53 has been long sought as a potentially novel cancer therapeutic strategy. In tumor harboring wild-type p53, MDM2 is the primary cellular inhibitor of p53 activity, and overexpression of MDM2 was found in many human tumors. Since MDM2 inhibits p53 through a direct protein-protein interaction, blocking this interaction using small molecules was pursued in several academic and industrial pharmaceutical laboratories in the last decade. A variety of non-peptide, drug-like small molecule as e.g. imidazole compounds (e.g. Nutlins or RG7112), benzodiazepinedione compounds, spirooxindole compounds (e.g. MI-219), substituted piperidines, pyrrolidinone compounds (e.g. PXN820-dl) and modifications thereof have been selected and designed in order to block MDM2/p53 interaction as a means to reactivate p53 in cells (Vassilev et al., Science (2004) 303:844-848; Grasberger et al., J Med Chem (2005) 48:909-912; Parks et al., Bioorg Med Chem Lett (2005) 15:765; Ding et al., J Am Soc (2005) 127:10130-10131; WO 2010/028862, U.S. Pat. No. 7,884,107, WO 2008/119741). A number of potent MDM2/p53 inhibitors have been evaluated in animal models of human cancer for their anti-tumor activity (Vassilev et al., Science (2004) 303:844-848; Tovar et al, Cancer Res (2013) 73 (8): 2587-2597; Ding et al, Journal of Medicinal Chemistry (2013) 56 (14): 5979-5983; Rew et al, Journal of Medicinal Chemistry (2012) 55: 4936-4954; Sun et al, Journal of Medicinal Chemistry (2014) 57 (4): 1454-1472).

In the pediatric preclinical testing program (PPTP) of the NCI, early evidence for high level anti-proliferative activity of RG7112, an inhibitor of the MDM2-p53 interaction, could be observed in vitro and in vivo. In particular, RG-7112 showed cytotoxic activity with lower median $IC_{50}$ values for p53 wild-type vs. p53 mutant cell lines (Carol et aL, Pediatric Blood and Cancer (2013) 60(4):633-641). Moreover, RG-7112 induced tumor growth inhibition in solid tumor xenograft models and was particularly efficacious in in acute lymphoblastic leukemia (ALL) xenograft models with mixed-lineage leukemia (MLL) rearrangement, (Carol et al., Pediatric Blood and Cancer (2013) 60(4):633-641). Additionally, the antiproliferative and proapoptotic activity of RG7112 has been observed in human acute myeloid leukemia (AML) and human prostate tumor xenograft models harboring p53 wild-type (Tovar et al, Cancer Res (2013) 73 (8): 2587-2597).

Accordingly, small molecule inhibitors of the MDM2 protein interactions offer an important approach towards cancer therapy, either as a single agent, or in combination with a broad variety of anti-tumor therapies and thus, there is the need for further MDM2 inhibitors which can be useful in the treatment of cancer.

The following documents disclose spiro oxindole compounds as inhibitors of MDM2-p53 interaction:
WO 2007/104664; WO 2007/104714; WO 2008/141917; WO 2008/141975; WO 2009/077357; WO 2009/080488; WO 2010/084097; WO 2010/121995; WO 2011/067185; WO 2011/101297; WO 2011/134925; WO 2012/038307; WO 2012/022707; WO 2012/116989; WO 2006/091646; WO 2008/036168; WO 2011/060049; WO 2012/065022; WO 2012/155066; WO 2010/028862; WO 2011/153509 and WO 2012/121361.

The aim of the present invention is to provide new compounds which can be used for the prevention and/or treatment of a disease and/or condition characterised by excessive or abnormal cell proliferation, especially a disease and/or condition wherein the inhibition of the interaction between MDM2 and p53 is of therapeutic benefit.

The compounds according to the invention are characterised by a powerful inhibitory effect on the interaction between MDM2 and p53 and in turn a high efficacy against tumour cells, e.g. osteosarcoma, ALL etc., which is mediated through the inhibition of the interaction between MDM2 and p53. In addition to the inhibitory effect and cellular potency the compounds show good PK properties and selectivity against p53 mutant cell lines. Furthermore, they have good metabolic stability and, in contrast to many compounds known in the prior art, good chemical stability, i.e. they are for example less prone to epimerisation, a problem identified for many known representatives of spiro oxindoles in the prior art (see e.g. Zhao et al. J. Am. Chem. Soc 2013, 135, 7223-7234; Shu et al. Org. Process Res. Dev. 2013, 17, 247-256; WO 2012/065022).

DETAILED DESCRIPTION OF THE INVENTION

It has now been found that, surprisingly, the compounds according to the invention act as inhibitors of the interaction of specific proteins which are involved in controlling cell proliferation. Thus, the compounds according to the invention may be used for example for the treatment of diseases connected with this protein-protein interaction and characterised by excessive or abnormal cell proliferation.

The present invention ("embodiment 1") relates to a compound of formula (I)

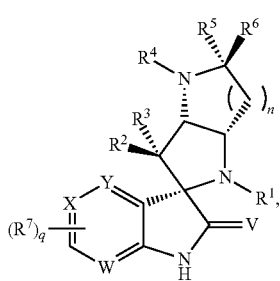

(I)

wherein $R^1$ is a group, optionally substituted by one or more, identical or different $R^{b1}$ and/or $R^{c1}$, selected from the group consisting of $C_{1-6}$alkyl, $C_{2-6}$alkenyl, $C_{2-6}$alkynyl, $C_{1-6}$haloalkyl, $C_{3-6}$cycloalkyl, $C_{4-6}$cycloalkenyl, $C_{6-10}$aryl, 5-10 membered heteroaryl and 3-10 membered heterocyclyl;

each $R^{b1}$ is independently selected from the group consisting of —$OR^{c1}$, —$NR^{c1}R^{c1}$, halogen, —CN, —C(O)$R^{c1}$, —C(O)O$R^{c1}$, —C(O)N$R^{c1}R^{c1}$, —S(O)$_2R^{c1}$, —S(O)$_2$N$R^{c1}R^{c1}$, —NHC(O)$R^{c1}$ and —N(C$_{1-4}$alkyl)C(O)$R^{c1}$;

each $R^{c1}$ independently of one another denotes hydrogen or a group, optionally substituted by one or more, identical or different $R^{d1}$ and/or $R^{e1}$, selected from the group consisting of $C_{1-6}$alkyl, $C_{2-6}$alkenyl, $C_{2-6}$alkynyl, $C_{1-6}$haloalkyl, $C_{3-6}$cycloalkyl, $C_{4-6}$cycloalkenyl, $C_{6-10}$aryl, 5-10 membered heteroaryl and 3-10 membered heterocyclyl;

each $R^{d1}$ is independently selected from the group consisting of —$OR^{e1}$, —$NR^{e1}R^{e1}$, halogen, —CN, —C(O)$R^{e1}$, —C(O)O$R^{e1}$, —C(O)N$R^{e1}R^{e1}$, —S(O)$_2R^{e1}$, —S(O)$_2$N$R^{e1}R^{e1}$, —NHC(O)$R^{e1}$ and —N(C$_{1-4}$alkyl)C(O)$R^{e1}$;

each $R^{e1}$ independently of one another denotes hydrogen or a group, optionally substituted by one or more, identical or different $R^{f1}$ and/or $R^{g1}$, selected from the group consisting of $C_{1-6}$alkyl, $C_{2-6}$alkenyl, $C_{2-6}$alkynyl, $C_{1-6}$haloalkyl, $C_{3-6}$cycloalkyl, $C_{4-6}$cycloalkenyl, $C_{6-10}$aryl, 5-10 membered heteroaryl and 3-10 membered heterocyclyl;

each $R^{f1}$ is independently selected from the group consisting of —$OR^{g1}$, —$NR^{g1}R^{g1}$, halogen, —CN, —C(O)$R^{g1}$, —C(O)O$R^{g1}$, —C(O)N$R^{g1}R^{g1}$, —S(O)$_2R^{g1}$, —S(O)$_2$N$R^{g1}R^{g1}$, —NHC(O)$R^{g1}$ and —N(C$_{1-4}$alkyl)C(O)$R^{g1}$;

each $R^{g1}$ is independently selected from the group consisting of hydrogen, $C_{1-6}$alkyl, $C_{2-6}$alkenyl, $C_{2-6}$alkynyl, $C_{1-6}$haloalkyl, $C_{3-6}$cycloalkyl, $C_{4-6}$cycloalkenyl, $C_{6-10}$aryl, 5-10 membered heteroaryl and 3-10 membered heterocyclyl;

$R^2$ and $R^3$, each independently, is selected from the group consisting of hydrogen, $C_{6-10}$aryl, 5-10 membered heteroaryl and 3-10 membered heterocyclyl, wherein this $C_{6-10}$aryl, 5-10 membered heteroaryl and 3-10 membered heterocyclyl is optionally substituted by one or more, identical or different $R^{b2}$ and/or $R^{c2}$;

each $R^{b2}$ is independently selected from the group consisting of —$OR^{c2}$, —$NR^{c2}R^{c2}$, halogen, —CN, —C(O)$R^{c2}$, —C(O)O$R^{c2}$, —C(O)N$R^{c2}R^{c2}$, —S(O)$_2R^{c2}$, —S(O)$_2$N$R^{c2}R^{c2}$, —NHC(O)$R^{c2}$ and —N(C$_{1-4}$alkyl)C(O) $R^{c2}$;

each $R^{c2}$ independently of one another denotes hydrogen or a group selected from the group consisting of $C_{1-6}$alkyl, $C_{2-6}$alkenyl, $C_{2-6}$alkynyl, $C_{1-6}$haloalkyl, $C_{3-6}$cycloalkyl, $C_{4-6}$cycloalkenyl, $C_{6-10}$aryl, 5-10 membered heteroaryl and 3-10 membered heterocyclyl;

$R^4$ is hydrogen or a group, optionally substituted by one or more, identical or different $R^{b3}$ and/or $R^{c3}$, selected from the group consisting of $C_{1-6}$alkyl, $C_{2-6}$alkenyl, $C_{2-6}$alkynyl, $C_{1-6}$haloalkyl, $C_{3-6}$cycloalkyl, $C_{4-6}$cycloalkenyl, $C_{6-10}$aryl, 5-10 membered heteroaryl and 3-10 membered heterocyclyl; or $R^4$ is selected from the group consisting of —CN, —C(O)$R^{c3}$, —C(O)O$R^{c3}$, —C(O)N$R^{c3}R^{c3}$, —S(O)$_2R^{c3}$ and —S(O)$_2$N$R^{c3}R^{c3}$;

each $R^{b3}$ is independently selected from the group consisting of —$OR^{c3}$, —$NR^{c3}R^{c3}$, halogen, —CN, —C(O)$R^{c3}$, —C(O)O$R^{c3}$, —C(O)N$R^{c3}R^{c3}$, —C(O)N$R^{g3}$O$R^{c3}$, —S(O)$_2R^{c3}$, —S(O)$_2$N$R^{c3}R^{c3}$, —NHC(O)$R^{c3}$ and —N(C$_{1-4}$alkyl)C(O)$R^{c3}$;

each $R^{c3}$ independently of one another denotes hydrogen or a group, optionally substituted by one or more, identical or different $R^{d3}$ and/or $R^{e3}$, selected from the group consisting of $C_{1-6}$alkyl, $C_{2-6}$alkenyl, $C_{2-6}$alkynyl, $C_{1-6}$haloalkyl, $C_{3-6}$cycloalkyl, $C_{4-6}$cycloalkenyl, $C_{6-10}$aryl, 5-10 membered heteroaryl and 3-10 membered heterocyclyl;

each $R^{d3}$ is independently selected from the group consisting of —$OR^{e3}$, —$NR^{e3}R^{e3}$, halogen, —CN, —C(O)$R^{e3}$, —C(O)O$R^{e3}$, —C(O)N$R^{e3}R^{e3}$, —C(O)N$R^{g3}$O$R^{e3}$, —S(O)$_2R^{e3}$, —S(O)$_2$N$R^{e3}R^{e3}$, —NHC(O)$R^{e3}$ and —N(C$_{1-4}$alkyl)C(O)$R^{e3}$;

each $R^{e3}$ independently of one another denotes hydrogen or a group, optionally substituted by one or more, identical or different $R^{f3}$ and/or $R^{g3}$, selected from the group consisting of $C_{1-6}$alkyl, $C_{2-6}$alkenyl, $C_{2-6}$alkynyl, $C_{1-6}$haloalkyl, $C_{3-6}$cycloalkyl, $C_{4-6}$cycloalkenyl, $C_{6-10}$aryl, 5-10 membered heteroaryl and 3-10 membered heterocyclyl;

each $R^{f3}$ is independently selected from the group consisting of —$OR^{g3}$, —$NR^{g3}R^{g3}$, halogen, —CN, —C(O)$R^{g3}$, —C(O)O$R^{g3}$, —C(O)N$R^{g3}R^{g3}$, —C(O)N$R^{g3}$O$R^{g3}$, —S(O)$_2R^{g3}$, —S(O)$_2$N$R^{g3}R^{g3}$, —NHC(O)$R^{g3}$ and —N(C$_{1-4}$alkyl)C(O)$R^{g3}$;

each $R^{g3}$ is independently selected from the group consisting of hydrogen, $C_{1-6}$alkyl, $C_{2-6}$alkenyl, $C_{2-6}$alkynyl, $C_{1-6}$haloalkyl, $C_{3-6}$cycloalkyl, $C_{4-6}$cycloalkenyl, $C_{6-10}$aryl, 5-10 membered heteroaryl and 3-10 membered heterocyclyl;

$R^5$ and $R^6$, each independently, is hydrogen or a group, optionally substituted by one or more, identical or different $R^{b4}$ and/or $R^{c4}$, selected from the group consisting of $C_{1-6}$alkyl, $C_{2-6}$alkenyl, $C_{2-6}$alkynyl, $C_{1-6}$haloalkyl, $C_{3-6}$cycloalkyl, $C_{4-6}$cycloalkenyl, $C_{6-10}$aryl, 5-10 membered heteroaryl and 3-10 membered heterocyclyl;

each $R^{b4}$ is independently selected from the group consisting of —$OR^{c4}$, —$NR^{c4}R^{c4}$, halogen, —CN, —C(O)$R^{c4}$, —C(O)O$R^{c4}$, —C(O)N$R^{c4}R^{c4}$, —C(O)N$R^{g4}$O$R^{c4}$, —S(O)$_2R^{c4}$, —S(O)$_2$N$R^{c4}R^{c4}$, —NHC(O)$R^{c4}$ and —N(C$_{1-4}$alkyl)C(O)$R^{c4}$;

each $R^{c4}$ independently of one another denotes hydrogen or a group, optionally substituted by one or more, identical or different $R^{d4}$ and/or $R^{e4}$, selected from the group consisting of $C_{1-6}$alkyl, $C_{2-6}$alkenyl, $C_{2-6}$alkynyl, $C_{1-6}$haloalkyl, $C_{3-6}$cycloalkyl, $C_{4-6}$cycloalkenyl, $C_{6-10}$aryl, 5-10 membered heteroaryl and 3-10 membered heterocyclyl;

each $R^{d4}$ is independently selected from the group consisting of —$OR^{e4}$, —$NR^{e4}R^{e4}$, halogen, —CN, —C(O)$R^{e4}$, —C(O)O$R^{e4}$, —C(O)N$R^{e4}R^{e4}$, —C(O)

$NR^{g4}OR^{e4}$, —$S(O)_2R^{e4}$, —$S(O)_2NR^{e4}R^{e4}$, —NHC(O)$R^{e4}$ and —$N(C_{1-4}alkyl)C(O)R^{e4}$;

each $R^{e4}$ independently of one another denotes hydrogen or a group, optionally substituted by one or more, identical or different $R^{f4}$ and/or $R^{g4}$, selected from the group consisting of $C_{1-6}$alkyl, $C_{2-6}$alkenyl, $C_{2-6}$alkynyl, $C_{1-6}$haloalkyl, $C_{3-6}$cycloalkyl, $C_{4-6}$cycloalkenyl, $C_{6-10}$aryl, 5-10 membered heteroaryl and 3-10 membered heterocyclyl;

each $R^{f4}$ is independently selected from the group consisting of —$OR^{g4}$, —$NR^{g4}R^{g4}$, halogen, —CN, —$C(O)R^{g4}$, —$C(O)OR^{g4}$, —$C(O)NR^{g4}R^{g4}$, —$C(O)NR^{g4} OR^{g4}$, —$S(O)_2R^{g4}$, —$S(O)_2NR^{g4}R^{g4}$, —NHC(O)$R^{g4}$ and —$N(C_{1-4}alkyl)C(O)R^{g4}$;

each $R^{g4}$ is independently selected from the group consisting of hydrogen, $C_{1-6}$alkyl, $C_{2-6}$alkenyl, $C_{2-6}$alkynyl, $C_{1-6}$haloalkyl, $C_{3-6}$cycloalkyl, $C_{4-6}$cycloalkenyl, $C_{6-10}$aryl, 5-10 membered heteroaryl and 3-10 membered heterocyclyl;

each $R^7$ is independently selected from the group consisting of halogen, $C_{1-4}$alkyl, —CN, $C_{1-4}$haloalkyl, —$OC_{1-4}$alkyl and —$OC_{1-4}$haloalkyl;

q denotes the number 0, 1, 2 or 3;

W, X and Y is each independently selected from —N═ and —CH═ with the proviso that the hydrogen in each —CH═ may be replaced by a substituent $R^7$ if present and that a maximum of two of W, X and Y can be —N═;

V is oxygen or sulfur;

n denotes the number 1, 2 or 3;

or a salt thereof.

The definition of $R^1$ in the first embodiment is referred to herein as structural aspect "[A0]."

The definitions of $R^2$ and $R^3$ in the first embodiment are referred to herein as structural aspect "[B0]."

The definition of $R^4$ in the first embodiment is referred to herein as structural aspect "[C0]."

The definitions of $R^5$ and $R^6$ in the first embodiment are referred to herein as structural aspect "[D0]."

The definition of $R^7$ in the first embodiment is referred to herein as structural aspect "[E0]."

The definitions of W, X and Y in the first embodiment are referred to herein as structural aspect "[F0]."

The definition of V in the first embodiment is referred to herein as structural aspect "[G0]."

The definition of n in the first embodiment is referred to herein as structural aspect "[H0]."

In one aspect the invention relates to the compound of formula (Ia)

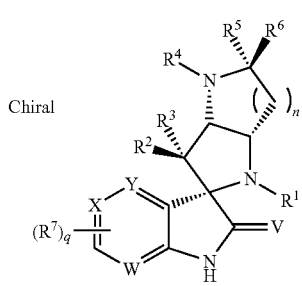

(Ia)

Chiral or a salt thereof, wherein the groups $R^1$ to $R^7$, V, W, X, Y, n and q are defined as for formula (I).

In another aspect the invention relates to the compound of formula (Ib)

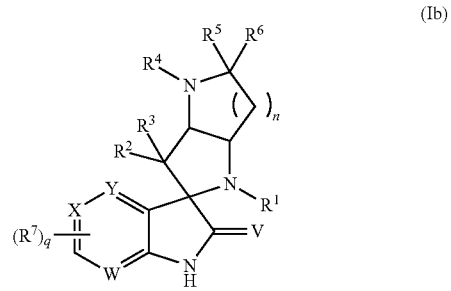

(Ib)

or a salt thereof, wherein the groups $R^1$ to $R^7$, V, W, X, Y, n and q are defined as for formula (I).

It is to be understood that compounds (Ia) are a subset of compounds (I) and that whenever the term "compounds (I)" is used this also includes compounds (Ia) unless stated otherwise.

It is to be understood that compounds (I) and compounds (Ia) are a subset of compounds (Ib) and that whenever the term "compounds (Ib)" is used this also includes compounds (I) and compounds (Ia) unless stated otherwise.

In another aspect [A1] the invention relates to a compound of formula (I) or (Ia) or (Ib), wherein $R^1$ is $C_{1-6}$alkyl, optionally substituted by a group selected from the group consisting of $C_{3-6}$cycloalkyl, $C_{6-10}$aryl and 5-10 membered heteroaryl, wherein this $C_{3-6}$cycloalkyl, $C_{6-10}$aryl and 5-10 membered heteroaryl is optionally substituted by one or more, identical or different $R^{d1}$ and/or $R^{e1}$;

each $R^{d1}$ is independently selected from the group consisting of —$OR^{e1}$, —$NR^{e1}R^{e1}$, halogen, —CN, —$C(O)R^{e1}$, —$C(O)OR^{e1}$, —$C(O)NR^{e1}R^{e1}$, —$S(O)_2R^{e1}$, —$S(O)_2NR^{e1}R^{e1}$, —NHC(O)$R^{e1}$ and —$N(C_{1-4}alkyl)C(O)R^{e1}$;

each $R^{e1}$ independently of one another denotes hydrogen or a group selected from the group consisting of $C_{1-6}$alkyl, $C_{2-6}$alkenyl, $C_{2-6}$alkynyl, $C_{1-6}$haloalkyl, $C_{3-6}$cycloalkyl, $C_{4-6}$cycloalkenyl, $C_{6-10}$aryl, 5-10 membered heteroaryl and 3-10 membered heterocyclyl;

or a salt thereof.

In another aspect [A2] the invention relates to a compound of formula (I) or (Ia) or (Ib), wherein $R^1$ is $C_{1-6}$alkyl, optionally substituted by a group selected from the group consisting of $C_{3-6}$cycloalkyl, phenyl and 5-6 membered heteroaryl, wherein this $C_{3-6}$cycloalkyl, phenyl and 5-6 membered heteroaryl is optionally substituted by one or more, identical or different $R^{d1}$ and/or $R^{e1}$;

each $R^{d1}$ is independently selected from the group consisting of —$OR^{e1}$, —$NR^{e1}R^{e1}$, halogen, —CN, —$C(O)R^{e1}$, —$C(O)OR^{e1}$, —$C(O)NR^{e1}R^{e1}$, —$S(O)_2R^{e1}$, —$S(O)_2NR^{e1}R^{e1}$, —NHC(O)$R^{e1}$ and —$N(C_{1-4}alkyl)C(O)R^{e1}$;

each $R^{e1}$ independently of one another denotes hydrogen or a group selected from the group consisting of $C_{1-6}$alkyl, $C_{2-6}$alkenyl, $C_{2-6}$alkynyl, $C_{1-6}$haloalkyl, $C_{3-6}$cycloalkyl, $C_{4-6}$cycloalkenyl, phenyl, 5-6 membered heteroaryl and 3-7 membered heterocyclyl;

or a salt thereof.

In another aspect [A3] the invention relates to a compound of formula (I) or (Ia) or (Ib), wherein $R^1$ is $C_{1-6}$alkyl, optionally substituted by a group selected from the group consisting of $C_{3-6}$cycloalkyl, phenyl and 5-6 membered heteroaryl, wherein this $C_{3-6}$cycloalkyl, phenyl and 5-6 membered heteroaryl is optionally substituted by one or more, identical or different substituents selected from the group consisting of —$OC_{1-6}$alkyl, halogen, $C_{1-6}$alkyl and $C_{1-6}$haloalkyl;
or a salt thereof.

In another aspect [A4] the invention relates to a compound of formula (I) or (Ia) or (Ib), wherein
$R^1$ is $C_{3-6}$cycloalkyl-$C_{1-6}$ alkyl;
or a salt thereof.

In another aspect [A5] the invention relates to a compound of formula (I) or (Ia) or (Ib), wherein
$R^1$ is cyclopropylmethyl;
or a salt thereof.

In another aspect [A6] the invention relates to a compound of formula (I) or (Ia) or (Ib), wherein
$R^1$ is benzyl, optionally substituted on the phenyl ring by one or more, identical or different $R^{d1}$ and/or $R^{e1}$;
  each $R^{d1}$ is independently selected from the group consisting of —$OR^{e1}$, —$NR^{e1}R^{e1}$, halogen, —CN, —C(O)$R^{e1}$, —C(O)$OR^{e1}$, —C(O)$NR^{e1}R^{e1}$, —S(O)$_2R^{e1}$, —S(O)$_2NR^{e1}R^{e1}$, —NHC(O)$R^{e1}$ and —N($C_{1-4}$alkyl)C(O)$R^{e1}$;
  each $R^{e1}$ independently of one another denotes hydrogen or a group selected from the group consisting of $C_{1-6}$alkyl, $C_{2-6}$alkenyl, $C_{2-6}$alkynyl, $C_{1-6}$haloalkyl, $C_{3-6}$cycloalkyl, $C_{4-6}$cycloalkenyl, phenyl, 5-6 membered heteroaryl and 3-7 membered heterocyclyl;
or a salt thereof.

In another aspect [A7] the invention relates to a compound of formula (I) or (Ia) or (Ib), wherein
$R^1$ is 3-ethoxybenzyl;
or a salt thereof.

In another aspect [B1] the invention relates to a compound of formula (I) or (Ia) or (Ib), wherein
one of $R^2$ and $R^3$ is hydrogen and the other is selected from the group consisting of phenyl and 5-6 membered heteroaryl, wherein this phenyl and 5-6 membered heteroaryl is optionally substituted by one or more, identical or different $R^{b2}$ and/or $R^{c2}$;
each $R^{b2}$ is independently selected from the group consisting of —$OR^{c2}$, —$NR^{c2}R^{c2}$, halogen, —CN, —C(O)$R^{c2}$, —C(O)$OR^{c2}$, —C(O)$NR^{c2}R^{c2}$, —S(O)$_2R^{c2}$, —S(O)$_2NR^{c2}R^{c2}$, —NHC(O)$R^{c2}$ and —N($C_{1-4}$alkyl)C(O) $R^{c2}$;
  each $R^{c2}$ independently of one another denotes hydrogen or a group selected from the group consisting of $C_{1-6}$alkyl, $C_{2-6}$alkenyl, $C_{2-6}$alkynyl, $C_{1-6}$haloalkyl, $C_{3-6}$cycloalkyl, $C_{4-6}$cycloalkenyl, phenyl, 5-6 membered heteroaryl and 3-7 membered heterocyclyl;
or a salt thereof.

In another aspect [B2] the invention relates to a compound of formula (I) or (Ia) or (Ib), wherein
one of $R^2$ and $R^3$ is hydrogen and the other is phenyl optionally substituted by one or more, identical or different substituents selected from the group consisting of —$OC_{1-6}$alkyl, halogen, $C_{1-6}$alkyl and $C_{1-6}$haloalkyl;
or a salt thereof.

In another aspect [B3] the invention relates to a compound of formula (I) or (Ia) or (Ib), wherein
one of $R^2$ and $R^3$ is hydrogen and the other is 3-chloro phenyl or 3-chloro 2-fluoro phenyl or a salt thereof.

In further aspects [B4], [B5], [B6] and [B7] the invention relates to a compound of formula (I) or (Ia) or (Ib) with structural aspects [B0], [B1], [B2] and [B3], wherein
$R^3$ is hydrogen;
or a salt thereof.

In further aspects [B8], [B9], [B10] and [B11] the invention relates to a compound of formula (I) or (Ia) or (Ib) with structural aspects [B0], [B1], [B2] and [B3], wherein
$R^2$ is hydrogen;
or a salt thereof.

In another aspect [C1] the invention relates to a compound of formula (I) or (Ia) or (Ib), wherein
$R^4$ is hydrogen or a group, optionally substituted by one or more, identical or different $R^{b3}$ and/or $R^{c3}$, selected from the group consisting of $C_{1-6}$alkyl, $C_{6-10}$aryl and 5-10 membered heteroaryl; or
$R^4$ is selected from the group consisting of —C(O)$R^{c3}$ and —S(O)$_2R^{c3}$;
  each $R^{b3}$ is independently selected from the group consisting of —$OR^{c3}$, —$NR^{c3}R^{c3}$, halogen, —CN, —C(O)$R^{c3}$, —C(O)$OR^{c3}$, —C(O)$NR^{c3}R^{c3}$, —C(O)$NR^{c3}OR^{c3}$, —S(O)$_2R^{c3}$, —S(O)$_2NR^{c3}R^{c3}$, —NHC(O)$R^{c3}$ and —N($C_{1-4}$alkyl)C(O)$R^{c3}$;
  each $R^{c3}$ independently of one another denotes hydrogen or a group, optionally substituted by one or more, identical or different $R^{d3}$ and/or $R^{e3}$, selected from the group consisting of $C_{1-6}$alkyl, $C_{3-6}$cycloalkyl, $C_{6-10}$aryl, 5-10 membered heteroaryl and 3-10 membered heterocyclyl;
  each $R^{d3}$ is independently selected from the group consisting of —$OR^{e3}$, —$NR^{e3}R^{e3}$, halogen, —CN, —C(O)$R^{e3}$, —C(O)$OR^{e3}$, —C(O)$NR^{e3}R^{e3}$, —C(O)$NR^{e3}OR^{e3}$, —S(O)$_2R^{e3}$, —S(O)$_2NR^{e3}R^{e3}$, —NHC(O)$R^{e3}$ and —N($C_{1-4}$alkyl)C(O)$R^{e3}$;
  each $R^{e3}$ independently of one another is selected from the group consisting of hydrogen, $C_{1-6}$alkyl, $C_{3-6}$cycloalkyl, $C_{6-10}$aryl, 5-10 membered heteroaryl and 3-10 membered heterocyclyl;
or a salt thereof.

In another aspect [C2] the invention relates to a compound of formula (I) or (Ia) or (Ib), wherein
$R^4$ is hydrogen or a group, optionally substituted by one or more, identical or different $R^{b3}$ and/or $R^{c3}$, selected from the group consisting of $C_{1-6}$alkyl, phenyl and 5-6 membered heteroaryl; or
$R^4$ is selected from the group consisting of —C(O)$R^{c3}$ and —S(O)$_2R^{c3}$;
  each $R^{b3}$ is independently selected from the group consisting of —$OR^{c3}$, —$NR^{c3}R^{c3}$, halogen, —CN, —C(O)$R^{c3}$, —C(O)$OR^{c3}$, —C(O)$NR^{c3}R^{c3}$, —C(O)$NR^{c3}OR^{c3}$, —S(O)$_2R^{c3}$, —S(O)$_2NR^{c3}R^{c3}$, —NHC(O)$R^{c3}$ and —N($C_{1-4}$alkyl)C(O)$R^{c3}$;
  each $R^{c3}$ independently of one another denotes hydrogen or a group, optionally substituted by one or more, identical or different $R^{d3}$ and/or $R^{e3}$, selected from the group consisting of $C_{1-6}$alkyl, $C_{3-6}$cycloalkyl, phenyl, 5-6 membered heteroaryl and 3-7 membered heterocyclyl;
  each $R^{d3}$ is independently selected from the group consisting of —$OR^{e3}$, —$NR^{e3}R^{e3}$, halogen, —CN, —C(O)$R^{e3}$, —C(O)$OR^{e3}$, —C(O)$NR^{e3}R^{e3}$, —C(O)$NR^{e3}OR^{e3}$, —S(O)$_2R^{e3}$, —S(O)$_2NR^{e3}R^{e3}$, —NHC(O)$R^{e3}$ and —N($C_{1-4}$alkyl)C(O)$R^{e3}$;
  each $R^{e3}$ independently of one another is selected from the group consisting of hydrogen, $C_{1-6}$alkyl, $C_{3-6}$cycloalkyl, phenyl, 5-6 membered heteroaryl and 3-7 membered heterocyclyl;
or a salt thereof.

In another aspect [C3] the invention relates to a compound of formula (I) or (Ia) or (Ib), wherein
$R^4$ is selected from the group consisting of $C_{1-6}$alkyl, $C_{3-6}$cycloalkyl-$C_{1-6}$alkyl, phenyl-$C_{1-6}$alkyl, and heteroaryl- $C_{1-6}$alkyl (the heteoaryl being 5-6 membered), all substituted by one substituent selected from the group consisting of —C(O)OH, —C(O)OC$_{1-6}$alkyl, —C(O)NH$_2$, —C(O)NHC$_{1-6}$alkyl and —C(O)N(C$_{1-6}$alkyl)$_2$;
or a salt thereof.

In another aspect [C4] the invention relates to a compound of formula (I) or (Ia) or (Ib), wherein
$R^4$ is selected from the group consisting of carboxymethyl and

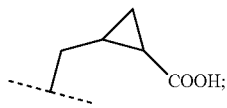

or a salt thereof.

In another aspect [C5] the invention relates to a compound of formula (I) or (Ia) or (Ib), wherein
$R^4$ is —C(O)R$^{c3}$;
 R$^{c3}$ is a group, optionally substituted by one or more, identical or different R$^{d3}$ and/or
 R$^{e3}$, selected from the group consisting of C$_{1-6}$alkyl, phenyl and 5-6 membered heteroaryl;
 each R$^{d3}$ is independently selected from the group consisting of —OR$^{e3}$, —NR$^{e3}$R$^{e3}$, —C(O)OR$^{e3}$, —C(O)NR$^{e3}$R$^{e3}$ and —NHC(O)R$^{e3}$;
 each R$^{e3}$ independently of one another is selected from the group consisting of hydrogen, C$_{1-6}$alkyl and 5-6 membered heteroaryl;
or a salt thereof.

In another aspect [C6] the invention relates to a compound of formula (I) or (Ia) or (Ib), wherein
$R^4$ is hydrogen;
or a salt thereof.

In another aspect [D1] the invention relates to a compound of formula (I) or (Ia) or (Ib), wherein
one of $R^5$ and $R^6$ is hydrogen and the other is hydrogen or a group, optionally substituted by one or more, identical or different R$^{b4}$ and/or R$^{c4}$, selected from the group consisting of C$_{1-6}$alkyl, C$_{6-10}$aryl and 5-10 membered heteroaryl;
 each R$^{b4}$ is independently selected from the group consisting of —OR$^{c4}$, —NR$^{c4}$R$^{c4}$, halogen, —CN, —C(O)R$^{c4}$, —C(O)OR$^{c4}$, —C(O)NR$^{c4}$R$^{c4}$, —C(O)NR$^{c4}$OR$^{c4}$, —S(O)$_2$R$^{c4}$, —S(O)$_2$NR$^{c4}$R$^{c4}$, —NHC(O)R$^{c4}$ and —N(C$_{1-4}$alkyl)C(O)R$^{c4}$;
 each R$^{c4}$ independently of one another denotes hydrogen or a group, optionally substituted by one or more, identical or different R$^{d4}$ and/or R$^{e4}$, selected from the group consisting of C$_{1-6}$alkyl, C$_{3-6}$cycloalkyl, C$_{6-10}$aryl, 5-10 membered heteroaryl and 3-10 membered heterocyclyl;
 each R$^{d4}$ is independently selected from the group consisting of —OR$^{e4}$, —NR$^{e4}$R$^{e4}$, halogen, —CN, —C(O)R$^{e4}$, —C(O)OR$^{e4}$, —C(O)NR$^{e4}$R$^{e4}$, —C(O)NR$^{e4}$OR$^{e4}$, —S(O)$_2$R$^{e4}$, —S(O)$_2$NR$^{e4}$R$^{e4}$, —NHC(O)R$^{e4}$ and —N(C$_{1-4}$alkyl)C(O)R$^{e4}$;
 each R$^{e4}$ independently of one another is selected from the group consisting of hydrogen, C$_{1-6}$alkyl, C$_{3-6}$cycloalkyl, C$_{6-10}$aryl, 5-10 membered heteroaryl and 3-10 membered heterocyclyl;
or a salt thereof.

In another aspect [D2] the invention relates to a compound of formula (I) or (Ia) or (Ib), wherein
one of $R^5$ and $R^6$ is hydrogen and the other is hydrogen or a group, optionally substituted by one or more, identical or different R$^{b4}$ and/or R$^{c4}$, selected from the group consisting of C$_{1-6}$alkyl, phenyl and 5-6 membered heteroaryl;
 each R$^{b4}$ is independently selected from the group consisting of —OR$^{c4}$, —NR$^{c4}$R$^{c4}$, halogen, —CN, —C(O)R$^{c4}$, —C(O)OR$^{c4}$, —C(O)NR$^{c4}$R$^{c4}$, —C(O)NR$^{c4}$OR$^{c4}$, —S(O)$_2$R$^{c4}$, —S(O)$_2$NR$^{c4}$R$^{c4}$, —NHC(O)R$^{c4}$ and —N(C$_{1-4}$alkyl)C(O)R$^{c4}$;
 each R$^{c4}$ independently of one another denotes hydrogen or a group, optionally substituted by one or more, identical or different R$^{d4}$ and/or R$^{e4}$, selected from the group consisting of C$_{1-6}$alkyl, C$_{3-6}$cycloalkyl, phenyl, 5-6 membered heteroaryl and 3-7 membered heterocyclyl;
 each R$^{d4}$ is independently selected from the group consisting of —OR$^{e4}$, —NR$^{e4}$R$^{e4}$, halogen, —CN, —C(O)R$^{e4}$, —C(O)OR$^{e4}$, —C(O)NR$^{e4}$R$^{e4}$, —C(O)NR$^{e4}$OR$^{e4}$, —S(O)$_2$R$^{e4}$, —S(O)$_2$NR$^{e4}$R$^{e4}$, —NHC(O)R$^{e4}$ and —N(C$_{1-4}$alkyl)C(O)R$^{e4}$;
 each R$^{e4}$ independently of one another is selected from the group consisting of hydrogen, C$_{1-6}$alkyl, C$_{3-6}$cycloalkyl, phenyl, 5-6 membered heteroaryl and 3-7 membered heterocyclyl;
or a salt thereof.

In another aspect [D3] the invention relates to a compound of formula (I) or (Ia) or (Ib), wherein
one of $R^5$ and $R^6$ is hydrogen and the other is hydrogen or a group, optionally substituted by one or more, identical or different R$^{b4}$ and/or R$^{c4}$, selected from the group consisting of C$_{1-6}$alkyl, phenyl and 5-6 membered heteroaryl;
 each R$^{b4}$ is independently selected from the group consisting of —OR$^{c4}$, —C(O)OR$^{c4}$ and —C(O)NR$^{c4}$R$^{c4}$;
 each R$^{c4}$ independently of one another denotes hydrogen or a group, optionally substituted by one or more, identical or different R$^{d4}$ and/or R$^{e4}$, selected from the group consisting of C$_{1-6}$alkyl, phenyl and 5-6 membered heteroaryl;
 each R$^{d4}$ is independently selected from the group consisting of —OR$^{e4}$, —C(O)OR$^{e4}$ and —C(O)NR$^{e4}$R$^{e4}$;
 each R$^{e4}$ independently of one another is selected from the group consisting of hydrogen and C$_{1-6}$alkyl;
or a salt thereof.

In another aspect [D4] the invention relates to a compound of formula (I) or (Ia) or (Ib), wherein
one of $R^5$ and $R^6$ is hydrogen and the other is hydrogen or a group, optionally substituted by one or more, identical or different R$^{b4}$, selected from the group consisting of C$_{1-6}$alkyl, phenyl and 5-6 membered heteroaryl;
 each R$^{b4}$ is independently selected from the group consisting of —OC$_{1-6}$alkyl, —C(O)OH, —C(O)OC$_{1-6}$alkyl, —C(O)NH$_2$, —C(O)NHC$_{1-6}$alkyl and —C(O)N(C$_{1-6}$alkyl)$_2$;
or a salt thereof.

In another aspect [D5] the invention relates to a compound of formula (I) or (Ia) or (Ib), wherein
one of $R^5$ and $R^6$ is hydrogen and the other is hydrogen or a group, optionally substituted by one or more, identical or different R$^{b4}$, selected from the group consisting of phenyl and 5-6 membered heteroaryl;
 each R$^{b4}$ is independently selected from the group consisting of —OC$_{1-6}$alkyl, —C(O)OH, —C(O)OC$_{1-6}$alkyl, —C(O)NH$_2$, —C(O)NHC$_{1-6}$alkyl and —C(O)N(C$_{1-6}$alkyl)$_2$;
or a salt thereof.

In another aspect [D6] the invention relates to a compound of formula (I) or (Ia) or (Ib), wherein
one of $R^5$ and $R^6$ is hydrogen and the other is hydrogen or

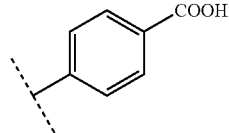

or a salt thereof.

In further aspects [D7], [D8], [D9], [D10], [D11], [D12] and [D13] the invention relates to a compound of formula (I) or (Ia) or (Ib) with structural aspects [D0], [D1], [D2], [D3], [D4], [D5] and [D6], wherein
$R^5$ is hydrogen and $R^6$ is not hydrogen;
or a salt thereof.

In further aspects [D14], [D15], [D16], [D17], [D18], [D19] and [D20] the invention relates to a compound of formula (I) or (Ia) or (Ib) with structural aspects [D0], [D1], [D2], [D3], [D4], [D5] and [D6], wherein
$R^6$ is hydrogen and $R^5$ is not hydrogen;
or a salt thereof.

In another aspect [D21] the invention relates to a compound of formula (I) or (Ia) or (Ib), wherein
$R^5$ and $R^6$ is hydrogen;
or a salt thereof.

In another aspect [E1] the invention relates to a compound of formula (I) or (Ia) or (Ib), wherein
each $R^7$ independently is halogen and q is 1 or 2;
or a salt thereof.

In another aspect [E2] the invention relates to a compound of formula (I) or (Ia) or (Ib), wherein
each $R^7$ independently is chlorine or fluorine and q is 1 or 2;
or a salt thereof.

In another aspect [F1] the invention relates to a compound of formula (I) or (Ia) or (Ib), wherein
W, X and Y are —CH=
with the proviso that the hydrogen in each —CH= may be replaced by a substituent $R^7$ if present;
or a salt thereof.

In another aspect [G1] the invention relates to a compound of formula (I) or (Ia) or (Ib), wherein
V is oxygen;
or a salt thereof.

In another aspect [H1] the invention relates to a compound of formula (I) or (Ia) or (Ib), wherein
n is 1;
or a salt thereof.

In another aspect [H2] the invention relates to a compound of formula (I) or (Ia) or (Ib), wherein
n is 2;
or a salt thereof.

In another aspect [EF1] the invention relates to a compound of formula (I) or (Ia) or (Ib), wherein the 6-membered ring comprising W, X and Y together with the q substituents $R^7$ has a substructure selected from the group consisting of (i) and (ii)

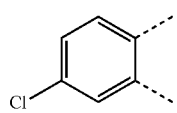

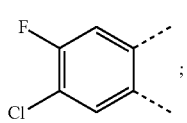

or a salt thereof.

All the above-mentioned structural aspects A1 to A7, B1 to B11, C1 to C6, D1 to D21, E1 and E2, F1, G1, H1 and H2 and EF1 are preferred embodiments of the corresponding aspects A0, B0, C0, D0, E0, F0, EF0, G0 and H0, respectively, wherein EF0 (EF) represents the combination of E0 (E) and F0 (F). The structural aspects A0 to A7, B0 to B11, C0 to C6, D0 to D21, E0 to E2, F0 and F1, EF1, G0 and G1, and H0 to H2 relating to different molecular parts of the compounds (I), (Ia) and (Ib) according to the invention may be permutated with one another as desired in combinations ABCDEFGH, so as to obtain preferred compounds (I), (Ia) and (Ib) (aspects E and F can be replaced by combination aspect EF). Each combination ABCDEFGH represents and defines individual embodiments or generic subsets of compounds according to the invention.

Preferred embodiments of the invention are example compounds I-1 to I-93.

All synthetic intermediates disclosed herein are also part of the invention.

In a further aspect the invention also relates to synthetic intermediates of formula A-4 and their salts, which can be used as key intermediates in the synthesis of compounds of formula (I) or (Ia) or (Ib):

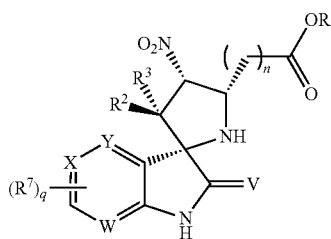

The definitions of groups $R^2$, $R^3$, $R^7$, V, W, X, Y, n and q in A-4 correspond to those as given for compound (I) and (Ia) and (Ib) above, i.e. [B0] for $R^2/R^3$, [E0] for $R^7/q$, [F0] for W/X/Y, [G0] for V and [H0] for n. Residue R in the group —COOR can be any residue that allows reduction of the corresponding alcohol and/or allows attack of metallorganic reagents like GRIGNARD reagents etc. [10]. The skilled person is aware of appropriate residues R. Preferred R are e.g. hydrogen, optionally substituted $C_{1-6}$alkyl, phenyl, benzyl [11] and the like (without being limited to them). More preferred is $C_{1-6}$alkyl[12].

Preferred intermediates A-4 are those which lead to preferred compounds (I) or (Ia) or (Ib) according to the invention, i.e. preferred embodiments of A-4 have structural aspects selected from [B0] to [B11] for $R^2/R^3$, [E0] to [E2] for $R^7/q$, [F0] and [F1] for W/X/Y, [G0] and [G1] for V, [H0] for n, [EF1] for $R^7/q/W/X/Y$ altogether and [I0] to [I2] for R. These structural aspects may be permutated with one another as desired in combinations BEFGHI, so as to obtain preferred intermediates A-4 (aspects E and F can be replaced by combination aspect EF). Each combination BEFGHI represents and defines individual embodiments or generic subsets of intermediates A-4.

In a further aspect the invention also relates to synthetic intermediates of formula A-7 and their salts, which can also be used as key intermediates in the synthesis of compounds of formula (I) or (Ia) or (Ib):

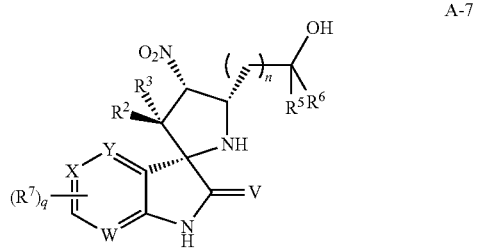

The definitions of groups $R^2$, $R^3$, $R^5$ to $R^7$, V, W, X, Y, n and q in A-7 correspond to those as given for compound (I) and (Ia) and (Ib) above, i.e. [B0] for $R^2/R^3$, [D0] for $R^5/R^6$, [E0] for $R^7/q$, [F0] for W/X/Y, [G0] for V and [H0] for n. Preferred intermediates A-7 are those which lead to preferred compounds (I) or (Ia) or (Ib) according to the invention, i.e. preferred embodiments of A-4 have structural aspects selected from [B0] to [B11] for $R^2/R^3$, [D0] to [D21] for $R^5/R^6$, [E0] to [E2] for $R^7/q$, [F0] and [F1] for W/X/Y, [G0] and [G1] for V, [H0] for n and [EF1] for $R^7/q$/W/X/Y altogether. These structural aspects may be permutated with one another as desired in combinations BDEFGH, so as to obtain preferred intermediates A-7 (aspects E and F can be replaced by combination aspect EF). Each combination BDEFGH represents and defines individual embodiments or generic subsets of intermediates A-7.

In a further aspect the invention also relates to synthetic intermediates of formula A-5, A-8, A-9, A-10, A-11, A-12, A-13, A-14, A-15 and A-16 as depicted in schemes 1, 2, 3, 4 and 5 (i.e. to both the generic group of compounds and the specific intermediates) and their salts, which can all also be used as key intermediates in the synthesis of compounds of formula (I) or (Ia) or (Ib).

The definitions of groups $R^1$ to $R^7$, R, V, W, X, Y, n and q in formulae formula A-5, A-8, A-9, A-10, A-11, A-12, A-13, A-14, A-15 and A-16 (as applicable) correspond to those as given for compound (I) and (Ia) and (Ib) above. Preferred intermediates A-5, A-8, A-9, A-10, A-11, A-12, A-13, A-14, A-15 and A-16 are those which lead to preferred compounds (I) or (Ia) or (Ib) according to the invention. The structural aspects may be permutated with one another as desired, so as to obtain preferred intermediates A-5, A-8, A-9, A-10, A-11, A-12, A-13, A-14, A-15 and A-16. Each combination represents and defines individual embodiments or generic subsets of intermediates A-5, A-8, A-9, A-10, A-11, A-12, A-13, A-14, A-15 and A-16.

In a further aspect the invention also relates to the use of synthetic intermediates of formula A-4 or their salts (and the various embodiments and sub-groups as described and/or defined herein) in the synthesis of compounds (I) or (Ia) or (Ib).

In a further aspect the invention also relates to the use of synthetic intermediates of formula A-7 or their salts (and the various embodiments and sub-groups as described and/or defined herein) in the synthesis of compounds (I) or (Ia) or (Ib).

In a further aspect the invention also relates to the use of synthetic intermediates of formula A-5, A-8, A-9, A-10, A-11, A-12, A-13, A-14, A-15 and A-16 (i.e. to both the generic group of compounds and the specific intermediates) or their salts (and the various embodiments and sub-groups as described and/or defined herein) in the synthesis of compounds (I) or (Ia) or (Ib).

The present invention further relates to hydrates, solvates, polymorphs, metabolites, derivatives, isomers and prodrugs of a compound of formula (I) or (Ia) or (Ib).

Compounds of formula (I) or (Ia) or (Ib) which e.g. bear ester groups are potential prodrugs the ester being cleaved under physiological conditions.

The present invention further relates to a pharmaceutically acceptable salt of a compound of formula (I) or (Ia) or (Ib).

The present invention further relates to a pharmaceutically acceptable salt of a compound of formula (I) or (Ia) or (Ib) with anorganic or organic acids or bases.

The present invention is directed to compounds of formula (I) or (Ia) or (Ib) which are useful in the prevention and/or treatment of a disease and/or condition wherein the inhibition of the interaction between MDM2 and p53 is of therapeutic benefit, including but not limited to the treatment and/or prevention of cancer.

In another aspect the invention relates to a compound of formula (I) or (Ia) or (Ib)—or a pharmaceutically acceptable salt thereof—for use as medicament.

In another aspect the invention relates to a compound of formula (I) or (Ia) or (Ib)—or a pharmaceutically acceptable salt thereof—for use in a method for treatment of the human or animal body.

In another aspect the invention relates to a compound of formula (I) or (Ia) or (Ib)—or a pharmaceutically acceptable salt thereof—for use in the treatment and/or prevention of a disease and/or condition wherein the inhibition of the interaction between MDM2 and p53 is of therapeutic benefit.

In another aspect the invention relates to a compound of formula (I) or (Ia) or (Ib)—or a pharmaceutically acceptable salt thereof—for use in the treatment and/or prevention of cancer, infections, inflammations and autoimmune diseases.

In another aspect the invention relates to a compound of formula (I) or (Ia) or (Ib)—or a pharmaceutically acceptable salt thereof—for use in a method for treatment and/or prevention of cancer, infections, inflammations and autoimmune diseases in the human and animal body.

In another aspect the invention relates to the use of a compound of formula (I) or (Ia) or (Ib)—or a pharmaceutically acceptable salt thereof—for preparing a pharmaceutical composition for the treatment and/or prevention of cancer, infections, inflammations and autoimmune diseases.

In another aspect the invention relates to a compound of formula (I) or (Ia) or (Ib)—or a pharmaceutically acceptable salt thereof—for use in the treatment and/or prevention of cancer.

In another aspect the invention relates to the use of a compound of formula (I) or (Ia) or (Ib)—or a pharmaceutically acceptable salt thereof—for preparing a pharmaceutical composition for the treatment and/or prevention of cancer.

In another aspect the invention relates to a compound of formula (I) or (Ia) or (Ib)—or a pharmaceutically acceptable salt thereof—for use in a method for treatment and/or prevention of cancer in the human or animal body.

In another aspect the invention relates to a compound of formula (I) or (Ia) or (Ib)—or a pharmaceutically acceptable salt thereof—for use in the treatment and/or prevention of acute myeloid leukaemia (AML), prostate cancer and lung cancer, wherein the cancer cells are p53 wild-type.

In another aspect the invention relates to a compound of formula (I) or (Ia) or (Ib)—or a pharmaceutically acceptable salt thereof—for use in the treatment and/or prevention of acute myeloid leukaemia (AML), prostate cancer and lung cancer, wherein the cancer cells are preferably p53 wild-type.

In another aspect the invention relates to the use of a compound of formula (I) or (Ia) or (Ib)—or a pharmaceutically acceptable salt thereof—for preparing a pharmaceutical composition for the treatment and/or prevention of acute myeloid leukaemia (AML), prostate cancer and lung cancer, wherein the cancer cells are p53 wild-type.

In another aspect the invention relates to the use of a compound of formula (I) or (Ia) or (Ib)—or a pharmaceutically acceptable salt thereof—for preparing a pharmaceutical composition for the treatment and/or prevention of acute myeloid leukaemia (AML), prostate cancer and lung cancer, wherein the cancer cells are preferably p53 wild-type.

In another aspect the invention relates to a method for the treatment and/or prevention of a disease and/or condition wherein the inhibition of the interaction between MDM2 and p53 is of therapeutic benefit comprising administering a therapeutically effective amount of a compound of formula (I) or (Ia) or (Ib)—or a pharmaceutically acceptable salt thereof—to a human being.

In another aspect the invention relates to a method for the treatment and/or prevention of cancer comprising administering a therapeutically effective amount of a compound of formula (I) or (Ia) or (Ib)—or a pharmaceutically acceptable salt thereof—to a human being.

In another aspect the invention relates to a pharmaceutical composition comprising at least one compound of formula (I) or (Ia) or (Ib)—or a pharmaceutically acceptable salt thereof—and a pharmaceutically acceptable carrier.

In another aspect the invention relates to a pharmaceutical preparation comprising a compound of formula (I) or (Ia) or (Ib)—or a pharmaceutically acceptable salt thereof—and at least one other cytostatic or cytotoxic active substance, different from formula (I) or (Ia) or (Ib).

In another aspect the invention relates to a compound of formula (I) or (Ia) or (Ib)—or a pharmaceutically acceptable salt thereof—for use in the treatment and/or prevention of cancer, infections, inflammations and autoimmune diseases wherein said compound is administered before, after or together with at least one other cytostatic or cytotoxic active substance.

In another aspect the invention relates to the use of a compound of formula (I) or (Ia) or (Ib)—or a pharmaceutically acceptable salt thereof—for preparing a medicament for the treatment and/or prevention of cancer, infections, inflammations and autoimmune diseases wherein said compound is administered before, after or together with at least one other cytostatic or cytotoxic active substance.

In another aspect the invention relates to a cytostatic or cytotoxic active substance prepared for being administered before, after or together with a compound of formula (I) or (Ia) or (Ib)—or a pharmaceutically acceptable salt thereof—for use in the treatment and/or prevention of cancer, infections, inflammations and autoimmune diseases.

In another aspect the invention relates to a method for the treatment and/or prevention of cancer, infections, inflammations and autoimmune diseases comprising administering a therapeutically effective amount of a compound of formula (I) or (Ia) or (Ib)—or a pharmaceutically acceptable salt thereof—before, after or together with at least one other cytostatic or cytotoxic active substance to a human being.

Definitions

Terms not specifically defined herein should be given the meanings that would be given to them by one of skill in the art in light of the disclosure and the context. As used in the specification, however, unless specified to the contrary, the following terms have the meaning indicated and the following conventions are adhered to:

The use of the prefix $C_{x-y}$, wherein x and y each represent a natural number (x<y), indicates that the chain or ring structure or combination of chain and ring structure as a whole, specified and mentioned in direct association, may consist of a maximum of y and a minimum of x carbon atoms.

The indication of the number of members in groups that contain one or more heteroatom(s) (e.g. heteroalkyl, heteroaryl, heteroarylalkyl, heterocyclyl, heterocyclalkyl) relates to the total number of atoms of all the ring members or chain members or the total of all the ring and chain members.

The indication of the number of carbon atoms in groups that consist of a combination of carbon chain and carbon ring structure (e.g. cycloalkylalkyl, arylalkyl) relates to the total number of carbon atoms of all the carbon ring and carbon chain members. Obviously, a ring structure has at least three members.

In general, for groups comprising two or more subgroups (e.g. heteroarylalkyl, heterocyclalkyl, cycloalkylalkyl, arylalkyl) the last named subgroup is the radical attachment point, for example, the substituent aryl-$C_{1-6}$alkyl means an aryl group which is bound to a $C_{1-6}$alkyl group, the latter of which is bound to the core or to the group to which the substituent is attached.

Alkyl denotes monovalent, saturated hydrocarbon chains, which may be present in both straight-chain (unbranched) and branched form. If an alkyl is substituted, the substitution may take place independently of one another, by mono- or polysubstitution in each case, on all the hydrogen-carrying carbon atoms.

The term "$C_{1-5}$alkyl" includes for example H$_3$C—, H$_3$C—CH$_2$—, H$_3$C—CH$_2$—CH$_2$—, H$_3$C—CH(CH$_3$)—, H$_3$C—CH$_2$—CH$_2$—CH$_2$—, H$_3$C—CH$_2$—CH(CH$_3$)—, H$_3$C—CH(CH$_3$)—CH$_2$—, H$_3$C—C(CH$_3$)$_2$—, H$_3$C—CH$_2$—CH$_2$—CH$_2$—CH$_2$—, H$_3$C—CH$_2$—CH$_2$—CH(CH$_3$)—, H$_3$C—CH$_2$—CH(CH$_3$)—CH$_2$—, H$_3$C—CH(CH$_3$)—CH$_2$—CH$_2$—, H$_3$C—CH$_2$—C(CH$_3$)$_2$—, H$_3$C—C(CH$_3$)$_2$—CH$_2$—, H$_3$C—CH(CH$_3$)—CH(CH$_3$)— and H$_3$C—CH$_2$—CH(CH$_2$CH$_3$)—.

Further examples of alkyl are methyl (Me; —CH$_3$), ethyl (Et; —CH$_2$CH$_3$), 1-propyl (n-propyl; n-Pr; —CH$_2$CH$_2$CH$_3$), 2-propyl (i-Pr; iso-propyl; —CH(CH$_3$)$_2$), 1-butyl (n-butyl; n-Bu; —CH$_2$CH$_2$CH$_2$CH$_3$), 2-methyl-1-propyl (iso-butyl; i-Bu; —CH$_2$CH(CH$_3$)$_2$), 2-butyl (sec-butyl; sec-Bu; —CH(CH$_3$)CH$_2$CH$_3$), 2-methyl-2-propyl (tert-butyl; t-Bu; —C(CH$_3$)$_3$), 1-pentyl (n-pentyl; —CH$_2$CH$_2$CH$_2$CH$_2$CH$_3$), 2-pentyl (—CH(CH$_3$)CH$_2$CH$_2$CH$_3$), 3-pentyl (—CH(CH$_2$CH$_3$)$_2$), 3-methyl-1-butyl (iso-pentyl; —CH$_2$CH$_2$CH(CH$_3$)$_2$), 2-methyl-2-butyl (—C(CH$_3$)$_2$CH$_2$CH$_3$), 3-methyl-2-butyl (—CH(CH$_3$)CH(CH$_3$)$_2$), 2,2-dimethyl-1-propyl (neo-pentyl; —CH$_2$C(CH$_3$)$_3$), 2-methyl-1-butyl (—CH$_2$CH(CH$_3$)CH$_2$CH$_3$), 1-hexyl (n-hexyl; —CH$_2$CH$_2$CH$_2$CH$_2$CH$_2$CH$_3$), 2-hexyl (—CH(CH$_3$)CH$_2$CH$_2$CH$_2$CH$_3$), 3-hexyl (—CH(CH$_2$CH$_3$)(CH$_2$CH$_2$CH$_3$)), 2-methyl-2-pentyl (—C(CH$_3$)$_2$CH$_2$CH$_2$CH$_3$), 3-methyl-2-pentyl (—CH(CH$_3$)CH(CH$_3$)CH$_2$CH$_3$), 4-methyl-2-pentyl (—CH(CH$_3$)CH$_2$CH(CH$_3$)$_2$), 3-methyl-3-pentyl (—C(CH$_3$)(CH$_2$CH$_3$)$_2$), 2-methyl-3-pentyl (—CH(CH$_2$CH$_3$)CH(CH$_3$)$_2$), 2,3-dimethyl-2-butyl (—C(CH$_3$)$_2$CH(CH$_3$)$_2$), 3,3-dimethyl-2-butyl (—CH(CH$_3$)C(CH$_3$)$_3$), 2,3-dimethyl-1-butyl (—CH$_2$CH(CH$_3$)CH(CH$_3$)CH$_3$), 2,2-dimethyl-1-butyl (—CH$_2$C(CH$_3$)$_2$CH$_2$CH$_3$), 3,3- dimethyl-1-butyl (—CH$_2$CH$_2$C(CH$_3$)$_3$), 2-methyl-1-pentyl (—CH$_2$CH(CH$_3$)CH$_2$CH$_2$CH$_3$), 3-methyl-1-pentyl (—CH$_2$CH$_2$CH(CH$_3$)CH$_2$CH$_3$), 1-heptyl (n-heptyl), 2-methyl-1-hexyl, 3-methyl-1-hexyl, 2,2-dimethyl-1-pentyl, 2,3-dimethyl-1-pentyl, 2,4-dimethyl-1-pentyl, 3,3-dimethyl-1-pentyl, 2,2,3-trimethyl-1-butyl, 3-ethyl-1-pentyl, 1-octyl (n-octyl), 1-nonyl (n-nonyl); 1-decyl (n-decyl) etc.

By the terms propyl, butyl, pentyl, hexyl, heptyl, octyl, nonyl, decyl etc. without any further definition are meant saturated hydrocarbon groups with the corresponding number of carbon atoms, wherein all isomeric forms are included.

The above definition for alkyl also applies if alkyl is a part of another (combined) group such as for example $C_{x-y}$alkylamino or $C_{x-y}$alkyloxy.

The term alkylene can also be derived from alkyl. Alkylene is bivalent, unlike alkyl, and requires two binding partners. Formally, the second valency is produced by removing a hydrogen atom in an alkyl. Corresponding groups are for example —CH$_3$ and —CH$_2$—, —CH$_2$CH$_3$ and —CH$_2$CH$_2$— or >CHCH$_3$ etc.

The term "$C_{1-4}$alkylene" includes for example —(CH$_2$)—, —(CH$_2$—CH$_2$)—, —(CH(CH$_3$))—, —(CH$_2$—CH$_2$—CH$_2$)—, —(C(CH$_3$)$_2$)—, —(CH(CH$_2$CH$_3$))—, —(CH(CH$_3$)—CH$_2$)—, —(CH$_2$—CH(CH$_3$))—, —(CH$_2$—CH$_2$—CH$_2$—CH$_2$)—, —(CH$_2$—CH$_2$—CH(CH$_3$))—, —(CH(CH$_3$)—CH$_2$—CH$_2$)—, —(CH$_2$—CH(CH$_3$)—CH$_2$)—, —(CH$_2$—C(CH$_3$)$_2$)—, —(C(CH$_3$)$_2$—CH$_2$)—, —(CH(CH$_3$)—CH(CH$_3$))—, —(CH$_2$—CH(CH$_2$CH$_3$))—, —(CH(CH$_2$CH$_3$)—CH$_2$)—, —(CH(CH$_2$CH$_2$CH$_3$))—, —(CH(CH(CH$_3$))$_2$)— and —C(CH$_3$)(CH$_2$CH$_3$)—.

Other examples of alkylene are methylene, ethylene, propylene, 1-methylethylene, butylene, 1-methylpropylene, 1,1-dimethylethylene, 1,2-dimethylethylene, pentylene, 1,1-dimethylpropylene, 2,2-dimethylpropylene, 1,2-dimethylpropylene, 1,3-dimethylpropylene, hexylene etc.

By the generic terms propylene, butylene, pentylene, hexylene etc. without any further definition are meant all the conceivable isomeric forms with the corresponding number of carbon atoms, i.e. propylene includes 1-methylethylene and butylene includes 1-methylpropylene, 2-methylpropylene, 1,1-dimethylethylene and 1,2-dimethylethylene.

The above definition for alkylene also applies if alkylene is part of another (combined) group such as for example in HO—$C_{x-y}$alkyleneamino or H$_2$N—$C_{x-y}$alkyleneoxy.

Unlike alkyl, alkenyl consists of at least two carbon atoms, wherein at least two adjacent carbon atoms are joined together by a C—C double bond and a carbon atom can only be part of one C—C double bond. If in an alkyl as hereinbefore defined having at least two carbon atoms, two hydrogen atoms on adjacent carbon atoms are formally removed and the free valencies are saturated to form a second bond, the corresponding alkenyl is formed.

Examples of alkenyl are vinyl (ethenyl), prop-1-enyl, allyl (prop-2-enyl), isopropenyl, but-1-enyl, but-2-enyl, but-3-enyl, 2-methyl-prop-2-enyl, 2-methyl-prop-1-enyl, 1-methyl-prop-2-enyl, 1-methyl-prop-1-enyl, 1-methylidenepropyl, pent-1-enyl, pent-2-enyl, pent-3-enyl, pent-4-enyl, 3-methyl-but-3-enyl, 3-methyl-but-2-enyl, 3-methyl-but-1-enyl, hex-1-enyl, hex-2-enyl, hex-3-enyl, hex-4-enyl, hex-5-enyl, 2,3-dimethyl-but-3-enyl, 2,3-dimethyl-but-2-enyl, 2-methylidene-3-methylbutyl, 2,3-dimethyl-but-1-enyl, hexa-1,3-dienyl, hexa-1,4-dienyl, penta-1,4-dienyl, penta-1,3-dienyl, buta-1,3-dienyl, 2,3-dimethylbuta-1,3-diene etc.

By the generic terms propenyl, butenyl, pentenyl, hexenyl, butadienyl, pentadienyl, hexadienyl, heptadienyl, octadienyl, nonadienyl, decadienyl etc. without any further definition are meant all the conceivable isomeric forms with the corresponding number of carbon atoms, i.e. propenyl includes prop-1-enyl and prop-2-enyl, butenyl includes but-1-enyl, but-2-enyl, but-3-enyl, 1-methyl-prop-1-enyl, 1-methyl-prop-2-enyl etc.

Alkenyl may optionally be present in the cis or trans or E or Z orientation with regard to the double bond(s).

The above definition for alkenyl also applies when alkenyl is part of another (combined) group such as for example in $C_{x-y}$alkenylamino or $C_{x-y}$alkenyloxy.

Unlike alkylene, alkenylene consists of at least two carbon atoms, wherein at least two adjacent carbon atoms are joined together by a C—C double bond and a carbon atom can only be part of one C—C double bond. If in an alkylene as hereinbefore defined having at least two carbon atoms, two hydrogen atoms at adjacent carbon atoms are formally removed and the free valencies are saturated to form a second bond, the corresponding alkenylene is formed.

Examples of alkenylene are ethenylene, propenylene, 1-methylethenylene, butenylene, 1-methylpropenylene, 1,1-dimethylethenylene, 1,2-dimethylethenylene, pentenylene, 1,1-dimethylpropenylene, 2,2-dimethylpropenylene, 1,2-dimethylpropenylene, 1,3-dimethylpropenylene, hexenylene etc.

By the generic terms propenylene, butenylene, pentenylene, hexenylene etc. without any further definition are meant all the conceivable isomeric forms with the corresponding number of carbon atoms, i.e. propenylene includes 1-methylethenylene and butenylene includes 1-methylpropenylene, 2-methylpropenylene, 1,1-dimethylethenylene and 1,2-dimethylethenylene.

Alkenylene may optionally be present in the cis or trans or E or Z orientation with regard to the double bond(s).

The above definition for alkenylene also applies when alkenylene is a part of another (combined) group as for example in HO—$C_{x-y}$alkenyleneamino or H$_2$N—$C_{x-y}$alkenyleneoxy. Unlike alkyl, alkynyl consists of at least two carbon atoms, wherein at least two adjacent carbon atoms are joined together by a C—C triple bond. If in an alkyl as hereinbefore defined having at least two carbon atoms, two hydrogen atoms in each case at adjacent carbon atoms are formally removed and the free valencies are saturated to form two further bonds, the corresponding alkynyl is formed.

Examples of alkynyl are ethynyl, prop-1-ynyl, prop-2-ynyl, but-1-ynyl, but-2-ynyl, but-3-ynyl, 1-methyl-prop-2-ynyl, pent-1-ynyl, pent-2-ynyl, pent-3-ynyl, pent-4-ynyl, 3-methyl-but-1-ynyl, hex-1-ynyl, hex-2-ynyl, hex-3-ynyl, hex-4-ynyl, hex-5-ynyl etc.

By the generic terms propynyl, butynyl, pentynyl, hexynyl, heptynyl, octynyl, nonynyl, decynyl etc. without any further definition are meant all the conceivable isomeric forms with the corresponding number of carbon atoms, i.e. propynyl includes prop-1-ynyl and prop-2-ynyl, butynyl includes but-1-ynyl, but-2-ynyl, but-3-ynyl, 1-methyl-prop-1-ynyl, 1-methyl-prop-2-ynyl, etc.

If a hydrocarbon chain carries both at least one double bond and also at least one triple bond, by definition it belongs to the alkynyl subgroup.

The above definition for alkynyl also applies if alkynyl is part of another (combined) group, as for example in $C_{x-y}$alkynylamino or $C_{x-y}$alkynyloxy.

Unlike alkylene, alkynylene consists of at least two carbon atoms, wherein at least two adjacent carbon atoms are joined together by a C—C triple bond. If in an alkylene as hereinbefore defined having at least two carbon atoms, two hydrogen atoms in each case at adjacent carbon atoms are formally removed and the free valencies are saturated to form two further bonds, the corresponding alkynylene is formed.

Examples of alkynylene are ethynylene, propynylene, 1-methylethynylene, butynylene, 1-methylpropynylene, 1,1-dimethylethynylene, 1,2-dimethylethynylene, pentynylene, 1,1-dimethylpropynylene, 2,2-dimethylpropynylene, 1,2-dimethylpropynylene, 1,3-dimethylpropynylene, hexynylene etc.

By the generic terms propynylene, butynylene, pentynylene, hexynylene etc. without any further definition are meant all the conceivable isomeric forms with the corresponding number of carbon atoms, i.e. propynylene includes 1-methylethynylene and butynylene includes 1-methylpropynylene, 2-methylpropynylene, 1,1-dimethylethynylene and 1,2-dimethylethynylene.

The above definition for alkynylene also applies if alkynylene is part of another (combined) group, as for example in HO—$C_{x-y}$alkynyleneamino or $H_2N$—$C_{x-y}$alkynyleneoxy. By heteroatoms are meant oxygen, nitrogen and sulphur atoms.

Haloalkyl (haloalkenyl, haloalkynyl) is derived from the previously defined alkyl (alkenyl, alkynyl) by replacing one or more hydrogen atoms of the hydrocarbon chain independently of one another by halogen atoms, which may be identical or different. If a haloalkyl (haloalkenyl, haloalkynyl) is to be further substituted, the substitutions may take place independently of one another, in the form of mono- or polysubstitutions in each case, on all the hydrogen-carrying carbon atoms.

Examples of haloalkyl (haloalkenyl, haloalkynyl) are —$CF_3$, —$CHF_2$, —$CH_2F$, —$CF_2CF_3$, —$CHFCF_3$, —$CH_2CF_3$, —$CF_2CH_3$, —$CHFCH_3$, —$CF_2CF_2CF_3$, —$CF_2CH_2CH_3$, —CF=$CF_2$, —CCl=$CH_2$, —CBr=$CH_2$, —C≡C—$CF_3$, —$CHFCH_2CH_3$, —$CHFCH_2CF_3$ etc.

From the previously defined haloalkyl (haloalkenyl, haloalkynyl) are also derived the terms haloalkylene (haloalkenylene, haloalkynylene). Haloalkylene (haloalkenylene, haloalkynylene), unlike haloalkyl (haloalkenyl, haloalkynyl), is bivalent and requires two binding partners. Formally, the second valency is formed by removing a hydrogen atom from a haloalkyl (haloalkenyl, haloalkynyl).

Corresponding groups are for example —$CH_2F$ and —CHF—, —$CHFCH_2F$ and —$CHFCHF$— or >$CFCH_2F$ etc.

The above definitions also apply if the corresponding halogen-containing groups are part of another (combined) group.

Halogen relates to fluorine, chlorine, bromine and/or iodine atoms.

Cycloalkyl is made up of the subgroups monocyclic hydrocarbon rings, bicyclic hydrocarbon rings and spiro-hydrocarbon rings. The systems are saturated. In bicyclic hydrocarbon rings two rings are joined together so that they have at least two carbon atoms together. In spiro-hydrocarbon rings one carbon atom (spiroatom) belongs to two rings together.

If a cycloalkyl is to be substituted, the substitutions may take place independently of one another, in the form of mono- or polysubstitutions in each case, on all the hydrogen-carrying carbon atoms. Cycloalkyl itself may be linked as a substituent to the molecule via every suitable position of the ring system.

Examples of cycloalkyl are cyclopropyl, cyclobutyl, cyclopentyl, cyclohexyl, cycloheptyl, bicyclo[2.2.0]hexyl, bicyclo[3.2.0]heptyl, bicyclo[3.2.1]octyl, bicyclo[2.2.2]octyl, bicyclo[4.3.0]nonyl (octahydroindenyl), bicyclo[4.4.0]decyl (decahydronaphthyl), bicyclo[2.2.1]heptyl (norbornyl), bicyclo[4.1.0]heptyl (norcaranyl), bicyclo[3.1.1]heptyl (pinanyl), spiro[2.5]octyl, spiro[3.3]heptyl etc.

The above definition for cycloalkyl also applies if cycloalkyl is part of another (combined) group as for example in $C_{x-y}$cycloalkylamino, $C_{x-y}$cycloalkyloxy or $C_{x-y}$cycloalkylalkyl.

If the free valency of a cycloalkyl is saturated, then an alicyclic group is obtained.

The term cycloalkylene can thus be derived from the previously defined cycloalkyl. Cycloalkylene, unlike cycloalkyl, is bivalent and requires two binding partners. Formally, the second valency is obtained by removing a hydrogen atom from a cycloalkyl. Corresponding groups are for example:

cyclohexyl and

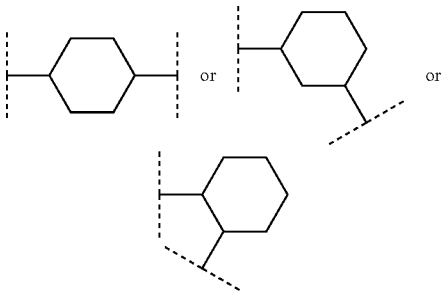

(cyclohexylene).

The above definition for cycloalkylene also applies if cycloalkylene is part of another (combined) group as for example in HO—$C_{x-y}$cycloalkyleneamino or $H_2N$—$C_{x-y}$cycloalkyleneoxy.

Cycloalkenyl is also made up of the subgroups monocyclic hydrocarbon rings, bicyclic hydrocarbon rings and spiro-hydrocarbon rings. However, the systems are unsaturated, i.e. there is at least one C—C double bond but no aromatic system. If in a cycloalkyl as hereinbefore defined two hydrogen atoms at adjacent cyclic carbon atoms are formally removed and the free valencies are saturated to form a second bond, the corresponding cycloalkenyl is obtained.

If a cycloalkenyl is to be substituted, the substitutions may take place independently of one another, in the form of mono- or polysubstitutions in each case, on all the hydrogen-carrying carbon atoms. Cycloalkenyl itself may be linked as a substituent to the molecule via every suitable position of the ring system.

Examples of cycloalkenyl are cycloprop-1-enyl, cycloprop-2-enyl, cyclobut-1-enyl, cyclobut-2-enyl, cyclopent-1-enyl, cyclopent-2-enyl, cyclopent-3-enyl, cyclohex-1-enyl, cyclohex-2-enyl, cyclohex-3-enyl, cyclohept-1-enyl, cyclohept-2-enyl, cyclohept-3-enyl, cyclohept-4-enyl, cyclobuta-1,3-dienyl, cyclopenta-1,4-dienyl, cyclopenta-1,3-dienyl, cyclopenta-2,4-dienyl, cyclohexa-1,3-dienyl, cyclohexa-1,5-dienyl, cyclohexa-2,4-dienyl, cyclohexa-1,4-dienyl, cyclohexa-2,5-dienyl, bicyclo[2.2.1]hepta-2,5-dienyl (norborna-2,5-dienyl), bicyclo[2.2.1]hept-2-enyl (norbornenyl), spiro[4,5]dec-2-enyl etc.

The above definition for cycloalkenyl also applies when cycloalkenyl is part of another (combined) group as for example in $C_{x-y}$cycloalkenylamino, $C_{x-y}$cycloalkenyloxy or $C_{x-y}$cycloalkenylalkyl.

If the free valency of a cycloalkenyl is saturated, then an unsaturated alicyclic group is obtained.

The term cycloalkenylene can thus be derived from the previously defined cycloalkenyl. Cycloalkenylene, unlike cycloalkenyl, is bivalent and requires two binding partners. Formally, the second valency is obtained by removing a hydrogen atom from a cycloalkenyl. Corresponding groups are for example:

cyclopentenyl and

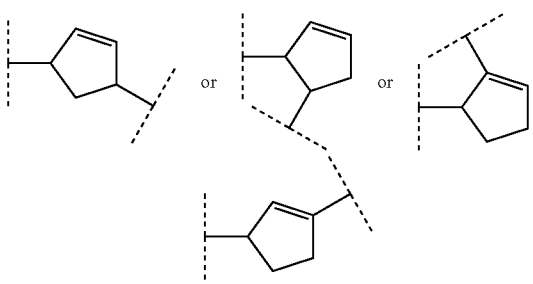

(cyclopentenylene) etc.

The above definition for cycloalkenylene also applies if cycloalkenylene is part of another (combined) group as for example in HO—$C_{x-y}$-cycloalkenyleneamino or $H_2N$—$C_{x-y}$-cycloalkenyleneoxy.

Aryl denotes mono-, bi- or tricyclic carbocycles with at least one aromatic carbocycle. Preferably, it denotes a monocyclic group with six carbon atoms (phenyl) or a bicyclic group with nine or ten carbon atoms (two six-membered rings or one six-membered ring with a five-membered ring), wherein the second ring may also be aromatic or, however, may also be partially saturated.

If an aryl is to be substituted, the substitutions may take place independently of one another, in the form of mono- or polysubstitutions in each case, on all the hydrogen-carrying carbon atoms. Aryl itself may be linked as a substituent to the molecule via every suitable position of the ring system.

Examples of aryl are phenyl, naphthyl, indanyl (2,3-dihydroindenyl), indenyl, anthracenyl, phenanthrenyl, tetrahydronaphthyl (1,2,3,4-tetrahydronaphthyl, tetralinyl), dihydronaphthyl (1,2-dihydronaphthyl), fluorenyl etc.

The above definition of aryl also applies if aryl is part of another (combined) group as for example in arylamino, aryloxy or arylalkyl.

If the free valency of an aryl is saturated, then an aromatic group is obtained.

The term arylene can also be derived from the previously defined aryl. Arylene, unlike aryl, is bivalent and requires two binding partners. Formally, the second valency is formed by removing a hydrogen atom from an aryl. Corresponding groups are for example:

phenyl and

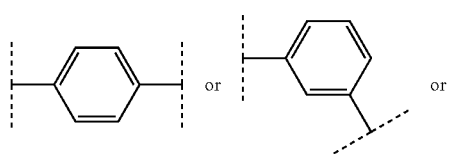

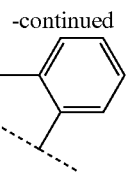

(o, m, p-phenylene), naphthyl and

[naphthyl structures]

etc.

The above definition for arylene also applies if arylene is part of another (combined) group as for example in HO-aryleneamino or $H_2N$-aryleneoxy.

Heterocyclyl denotes ring systems, which are derived from the previously defined cycloalkyl, cycloalkenyl and aryl by replacing one or more of the groups —$CH_2$-independently of one another in the hydrocarbon rings by the groups —O—, —S— or —NH— or by replacing one or more of the groups =CH— by the group =N—, wherein a total of not more than five heteroatoms may be present, at least one carbon atom must be present between two oxygen atoms and between two sulphur atoms or between an oxygen and a sulphur atom and the ring as a whole must have chemical stability. Heteroatoms may optionally be present in all the possible oxidation stages (sulphur→sulphoxide —SO—, sulphone —$SO_2$—; nitrogen→N-oxide). In a heterocyclyl there is no heteroaromatic ring, i.e. no heteroatom is part of an aromatic system.

A direct result of the derivation from cycloalkyl, cycloalkenyl and aryl is that heterocyclyl is made up of the subgroups monocyclic heterorings, bicyclic heterorings, tricyclic heterorings and spiro-heterorings, which may be present in saturated or unsaturated form.

By unsaturated is meant that there is at least one double bond in the ring system in question, but no heteroaromatic system is formed. In bicyclic heterorings two rings are linked together so that they have at least two (hetero)atoms in common. In spiro-heterorings one carbon atom (spiroatom) belongs to two rings together.

If a heterocyclyl is substituted, the substitutions may take place independently of one another, in the form of mono- or polysubstitutions in each case, on all the hydrogen-carrying carbon and/or nitrogen atoms. Heterocyclyl itself may be linked as a substituent to the molecule via every suitable position of the ring system.

Examples of heterocyclyl are tetrahydrofuryl, pyrrolidinyl, pyrrolinyl, imidazolidinyl, thiazolidinyl, imidazolinyl, pyrazolidinyl, pyrazolinyl, piperidinyl, piperazinyl, oxiranyl, aziridinyl, azetidinyl, 1,4-dioxanyl, azepanyl, diazepanyl, morpholinyl, thiomorpholinyl, homomorpholinyl, homopiperidinyl, homopiperazinyl, homothiomorpholinyl, thiomorpholinyl-S-oxide, thiomorpholinyl-S,S-dioxide, 1,3-dioxolanyl, tetrahydropyranyl, tetrahydrothiopyranyl, [1,4]-oxazepanyl, tetrahydrothienyl, homothiomorpholinyl-S,S-dioxide, oxazolidinonyl, dihydropyrazolyl, dihydropyrrolyl, dihydropyrazinyl, dihydropyridyl, dihydro-pyrimidinyl, dihydrofuryl, dihydropyranyl, tetrahydrothienyl-S-oxide, tetrahydrothienyl-S,S-dioxide, homothiomorpholinyl-S-oxide, 2,3-dihydroazet, 2H-pyrrolyl, 4H-pyranyl, 1,4-dihydro-pyridinyl, 8-aza-bicyclo[3.2.1]octyl, 8-aza-bicyclo[5.1.0]octyl, 2-oxa-5-azabicyclo[2.2.1]heptyl, 8-oxa-3-aza-bicyclo[3.2.1]octyl, 3,8-diaza-bicyclo[3.2.1]octyl, 2,5-diaza-bicyclo[2.2.1]heptyl, 1-aza-bicyclo[2.2.2]octyl, 3,8-diaza-bicyclo[3.2.1]octyl, 3,9-diaza-bicyclo[4.2.1]nonyl, 2,6-diaza-bicyclo[3.2.2]nonyl, 1,4-dioxa-spiro[4.5]decyl, 1-oxa-3,8-diaza-spiro[4.5]decyl, 2,6-diaza-spiro[3.3]heptyl, 2,7-diaza-spiro[4.4]nonyl, 2,6-diaza-spiro[3.4]octyl, 3,9-di-aza-spiro[5.5]undecyl, 2.8-diaza-spiro[4,5]decyl etc.

Further examples are the structures illustrated below, which may be attached via each hydrogen-carrying atom (exchanged for hydrogen):

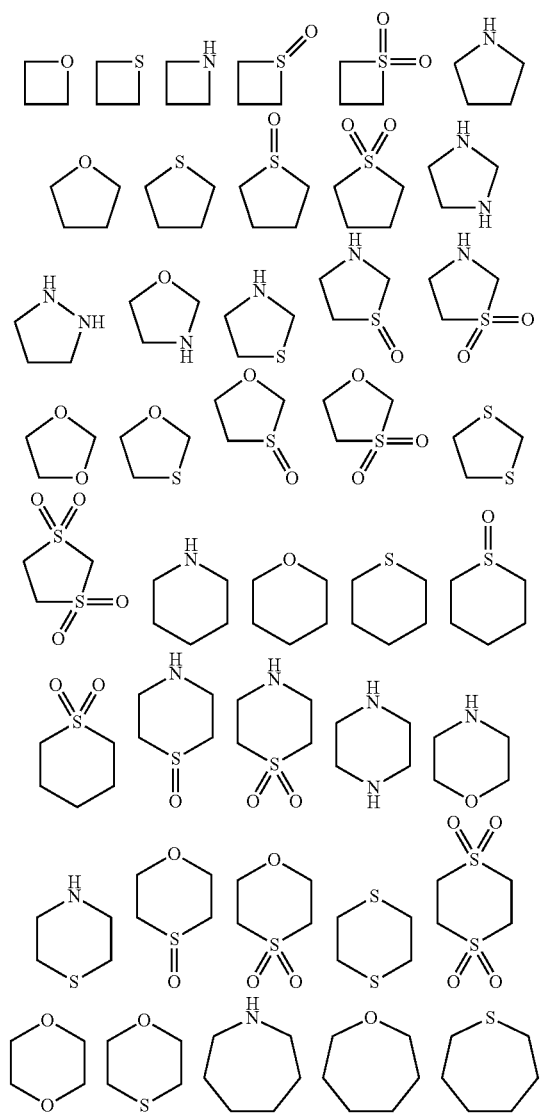
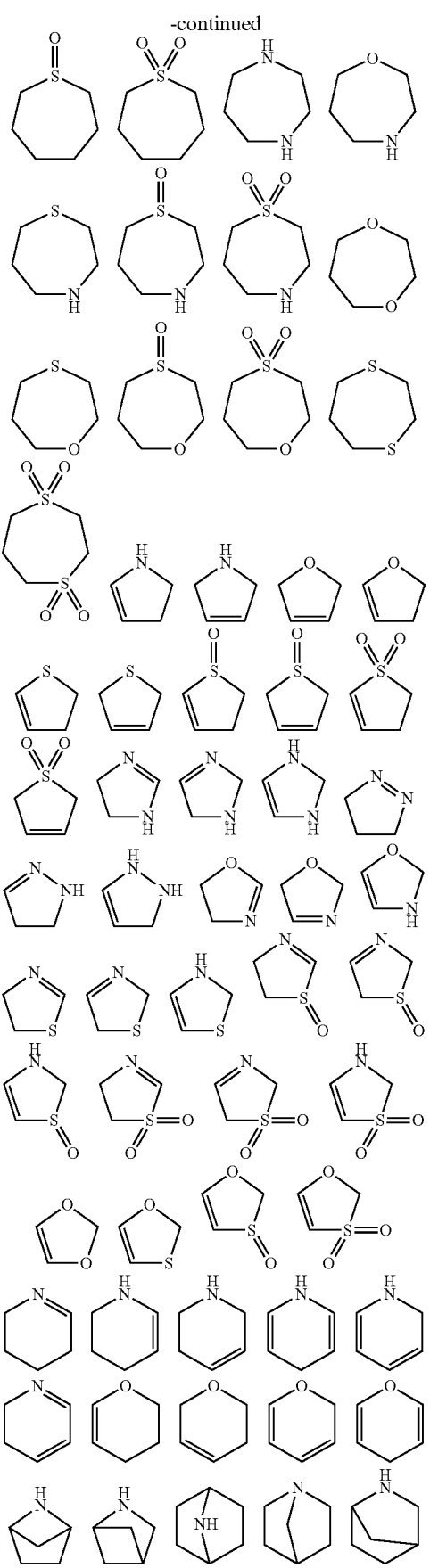

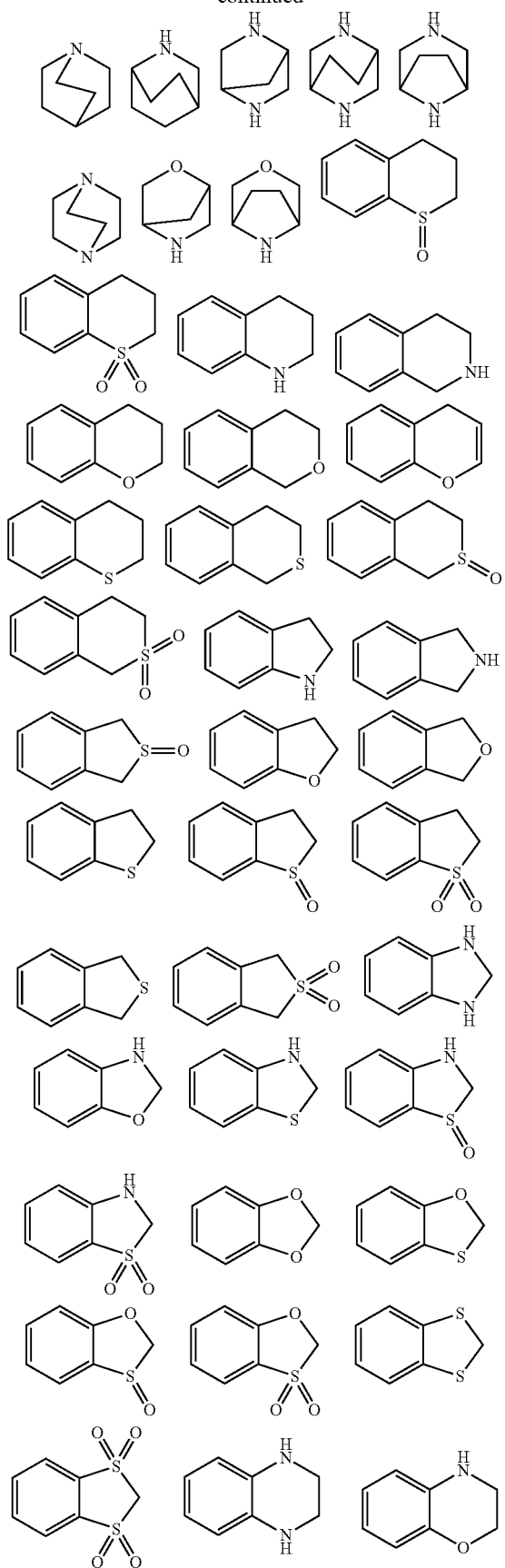

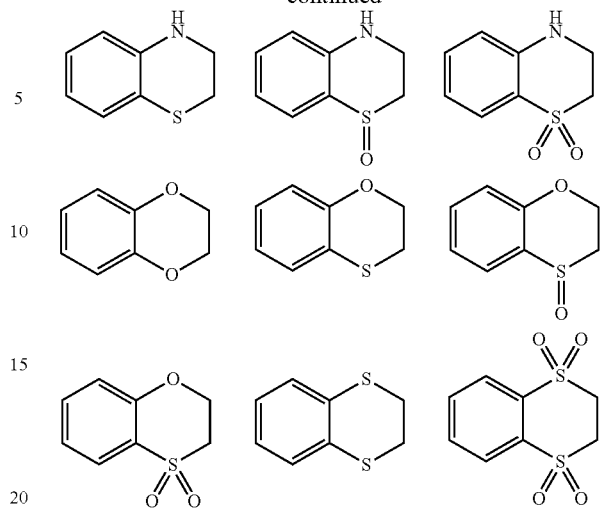

Preferably, heterocyclyls are 4 to 8 membered, monocyclic and have one or two heteroatoms independently selected from oxygen, nitrogen and sulfur Preferred heterocyclyls are: piperazinyl, piperidinyl, morpholinyl, pyrrolidinyl, azetidinyl, tetrahydropyranyl, tetrahydrofuranyl.

The above definition of heterocyclyl also applies if heterocyclyl is part of another (combined) group as for example in heterocyclylamino, heterocyclyloxy or heterocyclylalkyl.

If the free valency of a heterocyclyl is saturated, then a heterocyclic group is obtained.

The term heterocyclylene is also derived from the previously defined heterocyclyl. Heterocyclylene, unlike heterocyclyl, is bivalent and requires two binding partners. Formally, the second valency is obtained by removing a hydrogen atom from a heterocyclyl. Corresponding groups are for example:

piperidinyl and

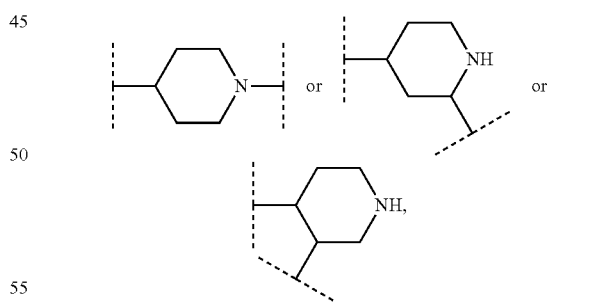

2,3-dihydro-1H-pyrrolyl and

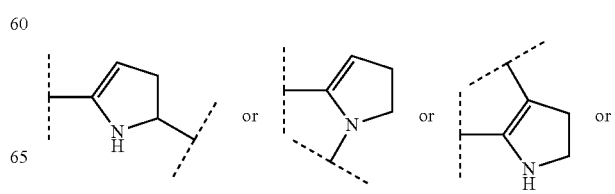

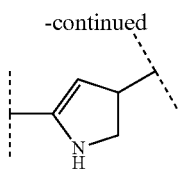

etc.

The above definition of heterocyclylene also applies if heterocyclylene is part of another (combined) group as for example in HO-heterocyclyleneamino or H₂N-heterocyclyleneoxy.

Heteroaryl denotes monocyclic heteroaromatic rings or polycyclic rings with at least one heteroaromatic ring, which compared with the corresponding aryl or cycloalkyl (cycloalkenyl) contain, instead of one or more carbon atoms, one or more identical or different heteroatoms, selected independently of one another from the group consisting of nitrogen, sulphur and oxygen, wherein the resulting group must be chemically stable. The prerequisite for the presence of heteroaryl is a heteroatom and a heteroaromatic system.

If a heteroaryl is to be substituted, the substitutions may take place independently of one another, in the form of mono- or polysubstitutions in each case, on all the hydrogen-carrying carbon and/or nitrogen atoms. Heteroaryl itself may be linked as a substituent to the molecule via every suitable position of the ring system, both carbon and nitrogen.

Examples of heteroaryl are furyl, thienyl, pyrrolyl, oxazolyl, thiazolyl, isoxazolyl, isothiazolyl, pyrazolyl, imidazolyl, triazolyl, tetrazolyl, oxadiazolyl, thiadiazolyl, pyridyl, pyrimidyl, pyridazinyl, pyrazinyl, triazinyl, pyridyl-N-oxide, pyrrolyl-N-oxide, pyrimidinyl-N-oxide, pyridazinyl-N-oxide, pyrazinyl-N-oxide, imidazolyl-N-oxide, isoxazolyl-N-oxide, oxazolyl-N-oxide, thiazolyl-N-oxide, oxadiazolyl-N-oxide, thiadiazolyl-N-oxide, triazolyl-N-oxide, tetrazolyl-N-oxide, indolyl, isoindolyl, benzofuryl, benzothienyl, benzoxazolyl, benzothiazolyl, benzisoxazolyl, benzisothiazolyl, benzimidazolyl, indazolyl, isoquinolinyl, quinolinyl, quinoxalinyl, cinnolinyl, phthalazinyl, quinazolinyl, benzotriazinyl, indolizinyl, oxazolopyridyl, imidazopyridyl, naphthyridinyl, benzoxazolyl, pyridopyridyl, pyrimidopyridyl, purinyl, pteridinyl, benzothiazolyl, imidazopyridyl, imidazothiazolyl, quinolinyl-N-oxide, indolyl-N-oxide, isoquinolyl-N-oxide, quinazolinyl-N-oxide, quinoxalinyl-N-oxide, phthalazinyl-N-oxide, indolizinyl-N-oxide, indazolyl-N-oxide, benzothiazolyl-N-oxide, benzimidazolyl-N-oxide etc.

Further examples are the structures illustrated below, which may be attached via each hydrogen-carrying atom (exchanged for hydrogen):

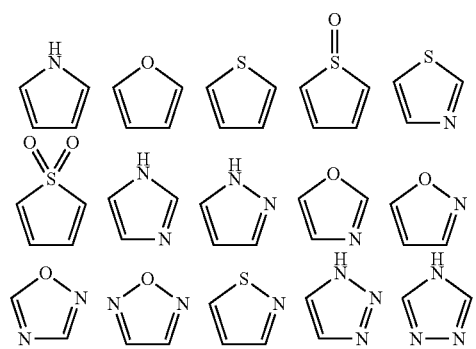

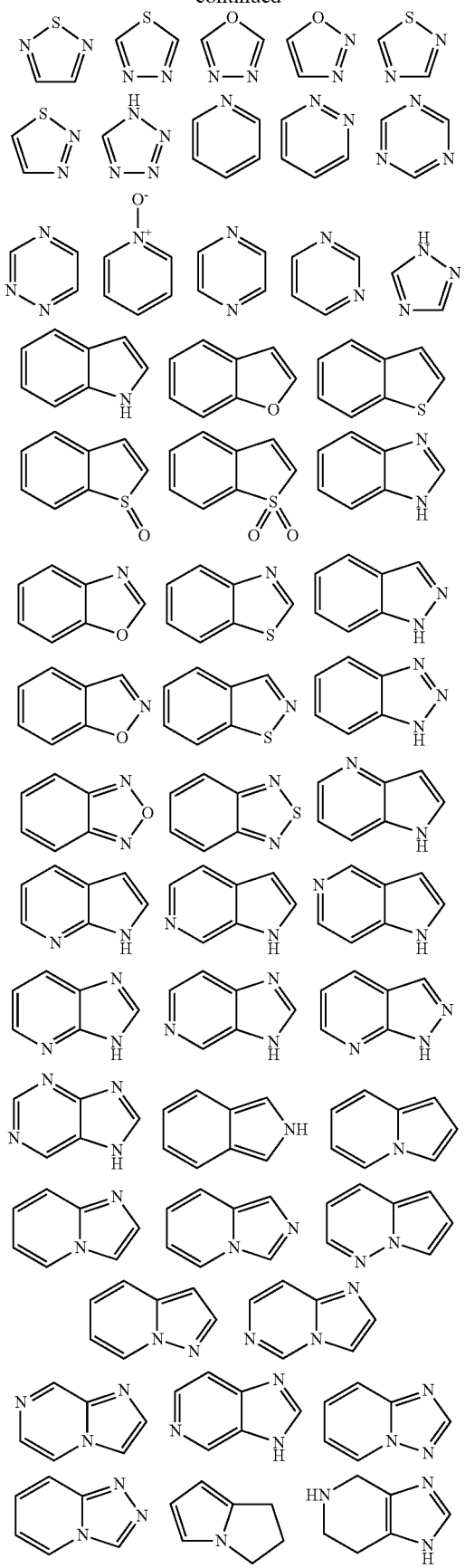

-continued

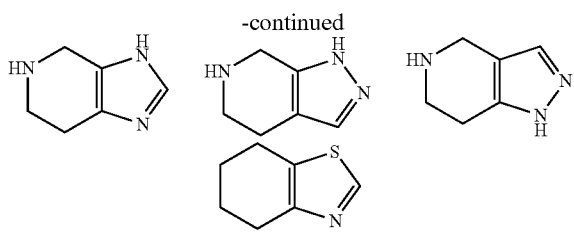

Preferably, heteroaryls are 5-6 membered monocyclic or 9-10 membered bicyclic, each with 1 to 4 heteroatoms independently selected from oxygen, nitrogen and sulfur.

The above definition of heteroaryl also applies if heteroaryl is part of another (combined) group as for example in heteroarylamino, heteroaryloxy or heteroarylalkyl.

If the free valency of a heteroaryl is saturated, a heteroaromatic group is obtained.

The term heteroarylene is also derived from the previously defined heteroaryl. Heteroarylene, unlike heteroaryl, is bivalent and requires two binding partners. Formally, the second valency is obtained by removing a hydrogen atom from a heteroaryl. Corresponding groups are for example: pyrrolyl and

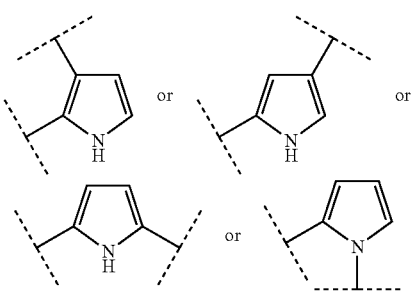

etc.

The above definition of heteroarylene also applies if heteroarylene is part of another (combined) group as for example in HO-heteroaryleneamino or H$_2$N-heteroaryleneoxy.

By substituted is meant that a hydrogen atom which is bound directly to the atom under consideration, is replaced by another atom or another group of atoms (substituent). Depending on the starting conditions (number of hydrogen atoms) mono- or polysubstitution may take place on one atom. Substitution with a particular substituent is only possible if the permitted valencies of the substituent and of the atom that is to be substituted correspond to one another and the substitution leads to a stable compound (i.e. to a compound which is not converted spontaneously, e.g. by rearrangement, cyclisation or elimination).

Bivalent substituents such as =S, =NR, =NOR, =NNRR, =NN(R)C(O)NRR, =N$_2$ or the like, may only be substituents on carbon atoms, wherein the bivalent substituent =O may also be a substituent on sulphur. Generally, substitution may be carried out by a bivalent substituent only at ring systems and requires replacement of two geminal hydrogen atoms, i.e. hydrogen atoms that are bound to the same carbon atom that is saturated prior to the substitution. Substitution by a bivalent substituent is therefore only possible at the group —CH$_2$— or sulphur atoms (=O only) of a ring system.

Stereochemistry/Solvates/Hydrates:

Unless specifically indicated, throughout the specification and appended claims, a given chemical formula or name shall encompass tautomers and all stereo, optical and geometrical isomers (e.g. enantiomers, diastereomers, E/Z isomers, etc.) and racemates thereof as well as mixtures in different proportions of the separate enantiomers, mixtures of diastereomers, or mixtures of any of the foregoing forms where such isomers and enantiomers exist, as well as salts, including pharmaceutically acceptable salts thereof and solvates thereof such as for instance hydrates including solvates of the free compounds or solvates of a salt of the compound.

Salts:

The phrase "pharmaceutically acceptable" is employed herein to refer to those compounds, materials, compositions, and/or dosage forms which are, within the scope of sound medical judgement, suitable for use in contact with the tissues of human beings and animals without excessive toxicity, irritation, allergic response, or other problem or complication, and commensurate with a reasonable benefit/risk ratio.

As used herein "pharmaceutically acceptable salts" refers to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like.

For example, such salts include salts from ammonia, L-arginine, betaine, benethamine, benzathine, calcium hydroxide, choline, deanol, diethanolamine (2,2'-iminobis (ethanol)), diethylamine, 2-(diethylamino)-ethanol, 2-(dimethylamino)-ethanol, 2-aminoethanol, ethylenediamine, N-ethyl-glucamine, hydrabamine, 1H-imidazole, lysine, magnesium hydroxide, 4-(2-hydroxyethyl)-morpholine, piperazine, potassium hydroxide, 1-(2-hydroxyethyl)-pyrrolidine, sodium hydroxide, triethanolamine (2,2',2"-nitrilotris (ethanol), tromethamine, zinc hydroxide, acetic acid, 2,2-dichloro acetic acid, adipic acid, alginic acid, ascorbic acid (L), L-aspartic acid, benzenesulfonic acid, benzoic acid, 2,5-dihydroxybenzoic acid, 4-acetamidobenzoic acid, (+)-camphoric acid, (+)-camphor-10-sulfonic acid, carbonic acid, cinnamic acid, citric acid, cyclamic acid, decanoic acid (capric acid), dodecylsulfuric acid, ethane-1,2-disulfonic acid, ethanesulfonic acid, 2-hydroxyethanesulfonic acid, ethylenediaminetetraacetic acid, formic acid, fumaric acid, galactaric acid, gentisic acid, D-glucoheptonic acid, D-gluconic acid, D-glucuronic acid, glutamic acid, glutaric acid, 2-oxoglutaric acid, glycerophosphoric acid, glycine, glycolic acid, hexanoic acid (caproic acid), hippuric acid, hydrobromic acid, hydrochloric acid, isobutyric acid, DL-lactic acid, lactobionic acid, lauric acid, maleic acid, (−)-L-malic acid, malonic acid, DL-mandelic acid, methanesulfonic acid, naphthalene-1,5-disulfonic acid, naphthalene-2-sulfonic acid, 1-hydroxy-2-naphthoic acid, nicotinic acid, nitric acid, octanoic acid (caprylic acid), oleic acid, orotic acid, oxalic acid, palmitic acid, pamoic acid (embonic acid), phosphoric acid, propionic acid, (−)-L-pyroglutamic acid, salicylic acid, 4-amino-salicylic acid, sebacic acid, stearic acid, succinic acid, sulfuric acid, tannic acid, (+)-L-tartaric acid, thiocyanic acid, p-toluenesulfonic acid and undecylenic acid.

The salts include acetates, ascorbates, benzenesulfonates, benzoates, besylates, bicarbonates, bitartrates, bromides/hydrobromides, Ca-edetates/edetates, camsylates, carbonates, camphorsulfonate, chlorides/hydrochlorides, chlorotheophyllinate, citrates, edisylates, ethane disulfonates, estolates esylates, fumarates, gluceptates, gluconates, glucuronate, glutamates, glycolates, glycollylarsnilates, hexyl-resorcinates, hippurate, hydrabamines, hydroxymaleates, hydroxynaphthoates, iodides, isethionates, isothionates, lactates, lactobionates, laurylsulfates, malates, maleates, mandelates, methanesulfonates, mesylates, methylbromides, methylnitrates, methylsulfates, mucates, naphthoate, napsylates, nitrates, octadecanoates, oleates, oxalates, pamoates, pantothenates, phenylacetates, phosphates/diphosphates, polygalacturonates, propionates, salicylates, stearates subacetates, succinates, sulfamides, sulfates, sulfosalicylates, tannates, tartrates, teoclates, toluenesulfonates, triethiodides, trifluoroacetates, ammonium, benzathines, chloroprocaines, cholines, diethanolamines, ethylenediamines, meglumines and procaines.

Further pharmaceutically acceptable salts can be formed with cations from metals like aluminium, calcium, lithium, magnesium, potassium, sodium, zinc and the like (also see Pharmaceutical salts, Berge, S. M. et al., J. Pharm. Sci., (1977), 66, 1-19).

The pharmaceutically acceptable salts of the present invention can be synthesized from the parent compound which contains a basic or acidic moiety by conventional chemical methods. Generally, such salts can be prepared by reacting the free acid or base form of these compounds with a sufficient amount of the appropriate base or acid in water or in an organic diluent like ether, ethyl acetate, ethanol, isopropanol, or acetonitrile, or a mixture thereof.

Salts of other acids than those mentioned above which for example are useful for purifying or isolating the compounds of the present invention (e.g. trifluoro acetate salts), also comprise a part of the invention.

Some abbreviated notations and their structure correspondences are listed below:

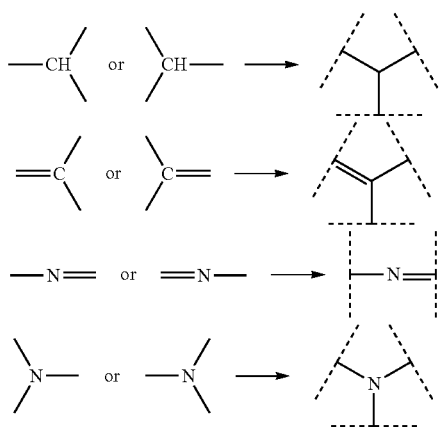

If for example in the sequence X—Y—Z the component Y is supposed to correspond to the structural section —N=, this means both X=N—Z and also X—N=Z.

In a representation such as for example

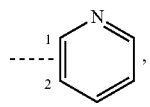

the dotted line means that the ring system may be attached to the molecule via the carbon atom 1 or 2, and is thus equivalent to the following representation

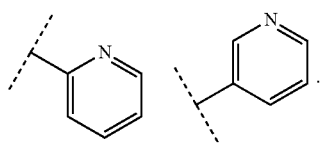

In a representation such as for example

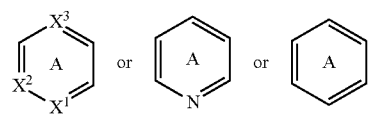

the letter A has the function of a ring designation in order to make it easier, for example, to indicate the attachment of the ring in question to other rings.

For bivalent groups in which it is crucial to determine which adjacent groups they bind and with which valency, the corresponding binding partners are indicated in brackets where necessary for clarification purposes, as in the following representations:

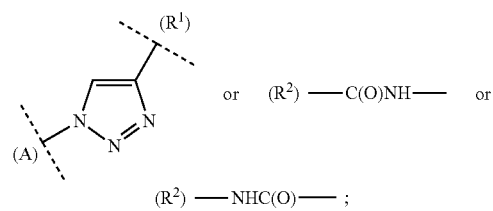

Groups or substituents are frequently selected from the group consisting of a number of alternative groups/substituents with a corresponding group designation (e.g. $R^a$, $R^b$ etc). If such a group is used repeatedly to define a compound according to the invention in different parts of the molecule, it is pointed out that the various uses are to be regarded as totally independent of one another.

By a therapeutically effective amount for the purposes of this invention is meant a quantity of substance that is capable of obviating symptoms of illness or of preventing or alleviating these symptoms, or which prolong the survival of a treated patient.

| List of abbreviations | |
|---|---|
| Ac | acetyl |
| AcCN | acetonitrile |
| aq. | aquatic, aqueous |
| ATP | adenosine triphosphate |
| Bn | benzyl |
| Boc | tert-butyloxycarbonyl |
| Bu | butyl |
| c | concentration |
| d | day(s) |
| dba | dibenzylideneacetone |
| TLC | thin layer chromatography |
| Davephos | 2-dimethylamino-2'-dicyclohexylaminophosphinobiphenyl |
| DBA | dibenzylideneacetone |
| DCM | dichloromethane |
| DEA | diethylamine |
| DEAD | diethyl azodicarboxylate |
| DIPEA | N-ethyl-N,N-diisopropylamine (Hunig's base) |
| DMAP | 4-N,N-dimethylaminopyridine |

List of abbreviations

| | |
|---|---|
| DME | 1,2-dimethoxyethane |
| DMF | N,N-dimethylformamide |
| DMSO | dimethylsulphoxide |
| DPPA | diphenylphosphorylazide |
| dppf | 1,1'-bis(diphenylphosphino)ferrocene |
| EDTA | ethylenediaminetetraacetic acid |
| EGTA | ethyleneglycoltetraacetic acid |
| eq | equivalent(s) |
| ESI | electron spray ionization |
| Et | ethyl |
| Et$_2$O | diethyl ether |
| EtOAc | ethyl acetate |
| EtOH | ethanol |
| h | hour |
| HATU | O-(7-azabenzotriazol-1-yl)-N,N,N',N'-tetramethyl-uronium hexafluorophosphate |
| HPLC | high performance liquid chromatography |
| IBX | 2-iodoxy benzoic acid |
| i | iso |
| conc. | concentrated |
| LC | liquid chromatography |
| LiHMDS | lithium bis(trimethylsilyl)amide |
| sln. | solution |
| Me | methyl |
| MeOH | methanol |
| min | minutes |
| MPLC | medium pressure liquid chromatography |
| MS | mass spectrometry |
| MTBE | methyl tert-butyl ether |
| NBS | N-bromo-succinimide |
| NIS | N-iodo-succinimide |
| NMM | N-methylmorpholine |
| NMP | N-methylpyrrolidone |
| NP | normal phase |
| n.a. | not available |
| PBS | phosphate-buffered saline |
| Ph | phenyl |
| Pr | propyl |
| Py | pyridine |
| rac | racemic |
| red. | reduction |
| Rf (R$_f$) | retention factor |
| RP | reversed phase |
| rt | ambient temperature |
| SFC | supercritical fluid chromatography |
| S$_N$ | nucleophilic substitution |
| TBAF | tetrabutylammonium fluoride |
| TBDMS | tert-butyldimethylsilyl |
| TBME | tert-butylmethylether |
| TBTU | O-(benzotriazol-1-yl)-N,N,N',N'-tetramethyl-uronium tetrafluoroborate |
| tBu | tert-butyl |
| TEA | triethylamine |
| temp. | temperature |
| tert | tertiary |
| Tf | triflate |
| TFA | trifluoroacetic acid |
| THF | tetrahydrofuran |
| TMS | trimethylsilyl |
| t$_{Ret.}$ | retention time (HPLC) |
| TRIS | tris(hydroxymethyl)-aminomethane |
| TsOH | p-toluenesulphonic acid |
| UV | ultraviolet |

Features and advantages of the present invention will become apparent from the following detailed examples which illustrate the principles of the invention by way of example without restricting its scope:

Preparation of the Compounds According to the Invention

General

Unless stated otherwise, all the reactions are carried out in commercially obtainable apparatus using methods that are commonly used in chemical laboratories. Starting materials that are sensitive to air and/or moisture are stored under protective gas and corresponding reactions and manipulations therewith are carried out under protective gas (nitrogen or argon).

The compounds according to the invention are named in accordance with CAS rules using the software Autonom (Beilstein). If a compound is to be represented both by a structural formula and by its nomenclature, in the event of a conflict the structural formula is decisive.

Microwave reactions are carried out in an initiator/reactor made by Biotage or in an Explorer made by CEM or in Synthos 3000 or Monowave 3000 made by Anton Paar in sealed containers (preferably 2, 5 or 20 mL), preferably with stirring.

Chromatography

The thin layer chromatography is carried out on ready-made silica gel 60 TLC plates on glass (with fluorescence indicator F-254) made by Merck.

The preparative high pressure chromatography (RP HPLC) of the example compounds according to the invention is carried out on Agilent or Gilson systems with columns made by Waters (names: SunFire™ Prep C18, OBD™ 10 µm, 50×150 mm or SunFire™ Prep C18 OBD™ 5 µm, 30×50 mm or XBridge™ Prep C18, OBD™ 10 µm, 50×150 mm or XBridge™ Prep C18, OBD™ 5 µm, 30×150 mm or XBridge™ Prep C18, OBD™ 5 µm, 30×50 mm) and YMC (names: Actus-Triart Prep C18, 5 µm, 30×50 mm).

Different gradients of H$_2$O/acetonitrile are used to elute the compounds, while for Agilent systems 5% acidic modifier (20 mL HCOOH to 1 L H$_2$O/acetonitrile (1/1)) is added to the water (acidic conditions). For Gilson systems the water is added 0.1% HCOOH.

For the chromatography under basic conditions for Agilent systems H$_2$O/acetonitrile gradients are used as well, while the water is made alkaline by addition of 5% basic modifier (50 g NH$_4$HCO$_3$+50 mL NH$_3$ (25% in H$_2$O) to 1 L with H$_2$O). For Gilson systems the water is made alkaline as follows: 5 mL NH$_4$HCO$_3$ solution (158 g in 1 L H$_2$O) and 2 mL NH$_3$ (28% in H$_2$O) are replenished to 1 L with H$_2$O.

The supercritical fluid chromatography (SFC) of the intermediates and example compounds according to the invention is carried out on a JASCO SFC-system with the following columns: Chiralcel OJ (250×20 mm, 5 µm), Chiralpak AD (250×20 mm, 5 µm), Chiralpak AS (250×20 mm, 5 µm), Chiralpak IC (250×20 mm, 5 µm), Chiralpak IA (250×20 mm, 5 µm), Chiralcel OJ (250×20 mm, 5 µm), Chiralcel OD (250×20 mm, 5 µm), Phenomenex Lux C2 (250×20 mm, 5 µm).

The analytical HPLC (reaction control) of intermediate compounds is carried out using columns made by Waters (names: XBridge™ C18, 2.5 µm, 2.1×20 mm or XBridge™ C18, 2.5 µm, 2.1×30 mm) and YMC (names: Triart C18, 3.0 µm, 2.0×30 mm). The analytical equipment is also equipped with a mass detector in each case.

HPLC-Mass Spectroscopy/UV-Spectrometry

The retention times/MS-ESI$^+$ for characterizing the example compounds according to the invention are produced using an HPLC-MS apparatus (high performance liquid chromatography with mass detector). Compounds that elute at the injection peak are given the retention time t$_{Ret.}$=0.00.

HPLC-Methods

Method A

HPLC Agilent 1100 Series

MS Agilent LC/MSD SL column Waters, Xbridge™ C18, 2.5 µm, 2.1×20 mm, Part. No. 186003201 solvent A: 20 mM NH$_4$HCO$_3$/NH$_3$ pH 9

B: acetonitrile (HPLC grade)
detection MS: positive and negative
    mass range: 120-900 m/z
    fragmentor: 120
    gain EMV: 1
    threshold: 150
    stepsize: 0.2
    UV: 315 nm
    bandwidth: 170 nm
    reference: off
    range: 230-400 nm
    range step: 1.00 nm
    peakwidth: <0.01 min
    slit: 1 nm
injection 5 μL
flow 1.00 mL/min
column temperature 60° C.
gradient 0.00 min 10% B
    0.00-1.50 min 10%→95% B
    1.50-2.00 min 95% B
    2.00-2.10 min 95%→10% B
Method B
HPLC Agilent 1200 Series
MS Agilent 6130 Quadropole LC/MS
column Waters, Xbridge™ C18, 2.5 μm, 2.1×30 mm
solvent A: 20 mM $NH_4HCO_3/NH_3$ in water; pH 9.3
    B: acetonitrile (HPLC grade)
detection MS:
    polarity: positive
    ionizator: MM-ES+APCI
    mass range: 150-750 m/z
    fragmentor values:

| mass | fragmentor |
|---|---|
| 150 | 70 |
| 750 | 110 | gain EMV: 1.00
    threshold: 150
    stepsize: 0.2
    UV:
    254 nm: reference off
    214 nm: reference off
    range: 190-400 nm
    range step: 2.00 nm
    threshold: 1.00 mAU
    peakwidth: 0.0025 min (0.05 s)
    slit: 4 nm
injection 0.5 μL
flow 1.400 mL/min
column temperature 45° C.
gradient 0.00-1.00 min 15%→95% B
    1.00-1.30 min 95% B
Method C
HPLC Agilent 1200 Series
MS Agilent 6130 Quadropole LC/MS
column YMC, Triart C18, 3.0 μm, 2.0×30 mm, 12 nm
solvent A: water+0.1% HCOOH
    B: acetonitrile+0.1% HCOOH (HPLC grade)
detection MS:
    polarity: positive
    mass range: 150-750 m/z
    fragmentor values:

| mass | fragmentor |
|---|---|
| 150 | 70 |
| 750 | 110 | gain EMV: 1.00
    threshold: 150
    stepsize: 0.20
    UV:
    254 nm: reference off
    214 nm: reference off
    range: 190-400 nm
    range step: 4.00 nm
    threshold: 1.00 mAU
    peakwidth: 0.005 min (0.1 s)
    slit: 4 nm
injection 0.5 μL
flow 1.400 mL/min
column temperature 45° C.
gradient 0.00-1.00 min 15%→100% B
    1.00-1.13 min 100% B
Method D
HPLC Agilent 1200 Series
MS Agilent 6130 Quadropole LC/MS
column Waters, Xbridge™ C18, 2.5 μm, 2.1×30 mm
solvent A: 20 mM $NH_4HCO_3/NH_3$ in water; pH 9.3
    B: acetonitrile (HPLC grade)
detection MS:
    polarity: positive+negative
    ionization: MM-ES
    mass range: 150-750 m/z
    fragmentor values:

| mass | fragmentor |
|---|---|
| 150 | 70 |
| 750 | 110 | gain EMV: 1.00
    threshold: 150
    stepsize: 0.2
    UV:
    254 nm: reference off
    214 nm: reference off
    range: 190-400 nm
    range step: 2.00 nm
    threshold: 1.00 mAU
    peakwidth: 0.0025 min (0.05 s)
    slit: 4 nm
injection 0.5 μL
flow 1.400 mL/min
column temperature 45° C.
gradient 0.00-1.00 min 15→95% B
    1.00-1.30 min 95% B
Method E
HPLC Agilent 1200 Series:
MS Agilent 6130 Quadropole LC/MS
column Waters, Xbridge™ C18, 2.5 μm, 2.1×30 mm Column XP; Part. No. 186006028
solvent A: 20 mM $NH_4HCO_3/NH_3$ in water; pH 9.3
    B: acetonitrile (HPLC grade)
detection MS:
    polarity: positive+negative
    ionizator: API-ES
    mass range: 150-750 m/z fragmentor values:

| mass | fragmentor |
|------|------------|
| 150  | 70         |
| 750  | 110        | gain EMV: 1.00  
threshold: 150  
stepsize: 0.2  
UV:  
254 nm: reference off  
214 nm: reference off  
range: 190-400 nm  
range step: 2.00 nm  
threshold: 1.00 mAU  
peakwidth: 0.0025 min (0.05 s)  
slit: 4 nm  
injection 0.5 μL  
flow 1.400 mL/min  
column temperature 45° C.  
gradient 0.00-1.00 min 15%→95% B  
    1.00-1.30 min 95% B  
Method F  
HPLC Agilent 1200 Series  
MS Agilent 6130 Quadropole LC/MS  
column YMC, Triart C18, 3.0 μm, 2.0×30 mm, 12 nm  
solvent A: water+0.1% HCOOH  
    B: acetonitrile+0.1% HCOOH (HPLC grade)  
detection MS:  
    polarity: positive+negative  
    mass range: 150-750 m/z  
    fragmentor values:

| mass | fragmentor |
|------|------------|
| 150  | 70         |
| 750  | 110        | gain EMV: 1.00  
threshold: 150  
stepsize: 0.20  
UV:  
254 nm: reference off  
214 nm: reference off  
range: 190-400 nm  
range step: 4.00 nm  
threshold: 1.00 mAU  
peakwidth: 0.0063 min (0.13 s)  
slit: 4 nm  
injection 0.5 μL  
flow 1.400 mL/min  
column temperature 45° C.  
gradient 0.00-1.00 min 15%→100% B  
    1.00-1.13 min 100% B  
Method G  
HPLC Agilent 1200 Series  
MS Agilent 6130 Quadropole LC/MS  
column YMC, Triart C18, 3.0 μm, 2.0×30 mm, 12 nm  
solvent A: water+0.1% HCOOH  
    B: acetonitrile+0.1% HCOOH (HPLC grade)  
detection MS:  
    polarity: positive+negative  
    mass range: 150-750 m/z  
    fragmentor values:

| Mass | Fragmentor |
|------|------------|
| 150  | 70         |
| 750  | 110        | gain EMV: 1.00  
threshold: 150  
stepsize: 0.20  
UV:  
254 nm: reference off  
230 nm: reference off  
214 nm: reference off  
range: 190-400 nm  
range step: 4.00 nm  
threshold: 1.00 mAU  
peakwidth: 0.005 min (0.1 s)  
slit: 4 nm  
injection 0.5 μL  
flow 1.400 mL/min  
column temperature 45° C.  
gradient 0.00-1.00 min 15%→100% B  
    1.00-1.13 min 100% B  
Method H  
HPLC Agilent 1200 Series  
MS Agilent 6130 Quadropole LC/MS  
column YMC, Triart C18, 3.0 μm, 2.0×30 mm, 12 nm  
solvent A: water+0.1% HCOOH  
    B: acetonitrile+0.1% HCOOH (HPLC grade)  
detection MS:  
    polarity: positive+negative  
    mass range: 200-800 m/z  
    fragmentor: 70  
    gain: 1.00  
    threshold: 150  
    stepsize: 0.20  
UV:  
254 nm: reference off  
230 nm: reference off  
range: 190-400 nm  
range step: 2.00 nm  
peakwidth: >0.01 min (0.2 s)  
slit: 4 nm  
injection 1.0 μL  
flow 1.000 mL/min  
column temperature 45° C.  
gradient 0.00-0.10 min 5% B  
    0.10-1.85 min 5% B→95.0% B  
    1.85-1.90 min 95% B  
    1.95-1.92 min 95% B→5.0% B  
Method I  
HPLC Agilent 1200 Series  
MS Agilent 6130 Quadropole LC/MS  
column YMC, Triart C18, 3.0 μm, 2.0×30 mm, 12 nm  
solvent A: water+0.1% HCOOH  
    B: acetonitrile+0.1% HCOOH (HPLC grade)  
detection MS:  
    polarity: positive+negative  
    mass range: 200-800 m/z  
    fragmentor: 70  
    gain: 1.00  
    threshold: 150  
    stepsize: 0.20  
UV:  
254 nm: reference off  
230 nm: reference off  
range: 190-400 nm range step: 2.00 nm
peakwidth: >0.01 min (0.2 s)
slit: 4 nm
injection 1.0 µL
flow 1.000 mL/min
column temperature 45° C.
gradient 0.00-0.10 min 15% B
   0.10-1.55 min 15% B→95.0% B
   1.55-1.90 min 95% B
   1.95-1.92 min 95% B→15.0% B The compounds according to the invention are prepared by the methods of synthesis described hereinafter in which the substituents of the general formulae have the meanings given hereinbefore. These methods are intended as an illustration of the invention without restricting its subject matter and the scope of the compounds claimed to these examples. Where the preparation of starting compounds is not described, they are commercially obtainable or may be prepared analogously to known prior art compounds or methods described herein. Substances described in the literature are prepared according to the published methods of synthesis.

General Reaction Scheme and Summary of the Synthesis Route

Scheme 1

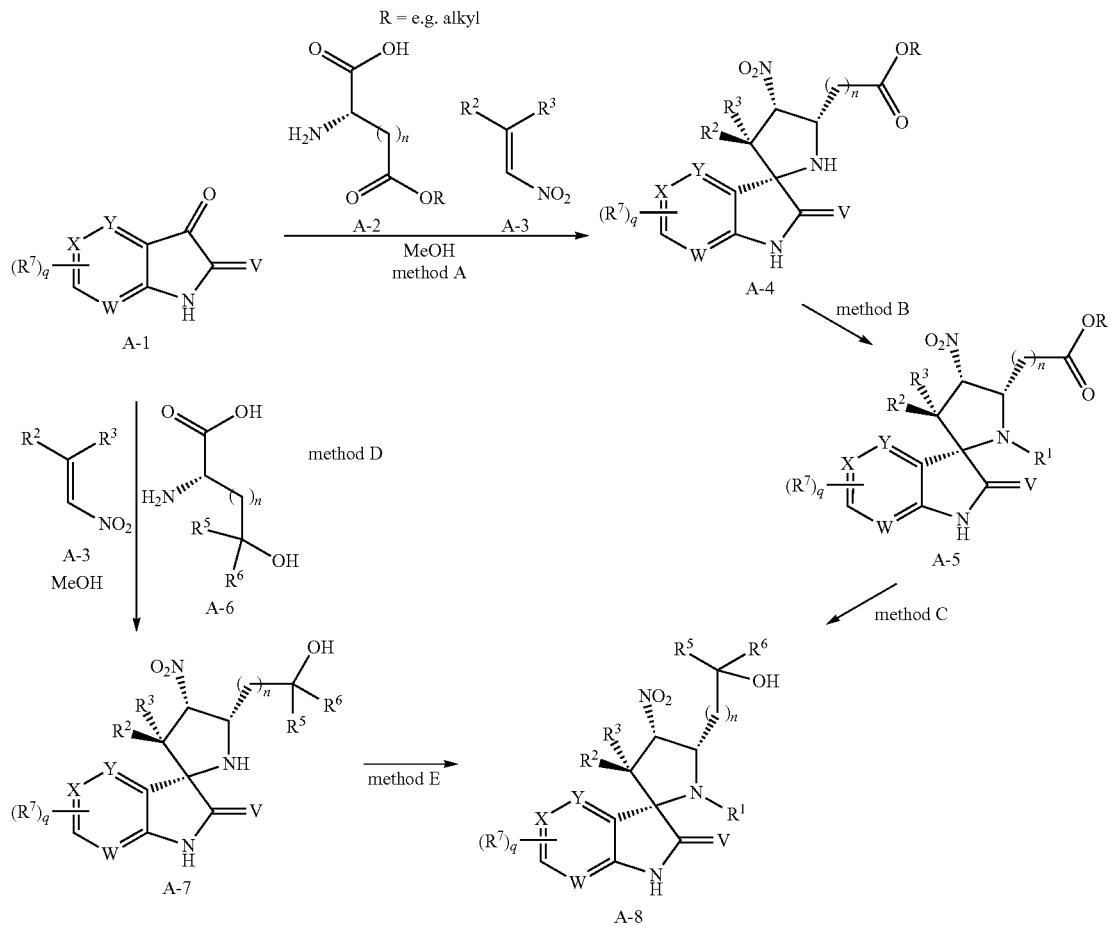

Scheme 2

-continued

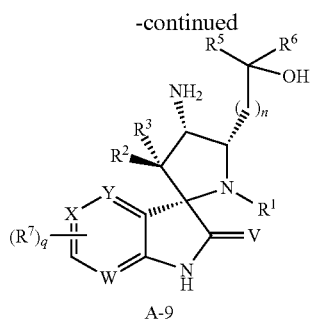
A-9

Scheme 3

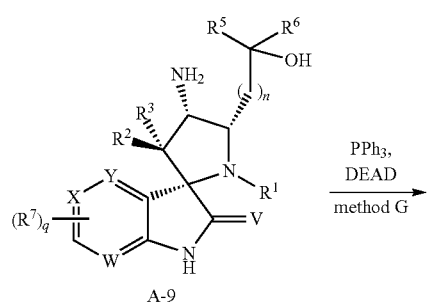

A-9 →(PPh₃, DEAD, method G)

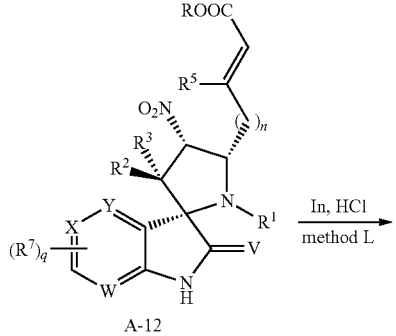

A-12 →(In, HCl, method L)

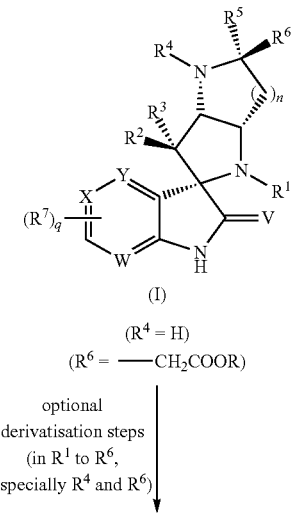

(I)
(R⁴ = H)
(R⁶ = —CH₂COOR)

optional derivatisation steps (in R¹ to R⁶, especially R⁴ and R⁶)

(I) (R⁴ = H) → optional derivatisation steps (in R¹ to R⁶, especially R⁴ and R⁶)

Scheme 4

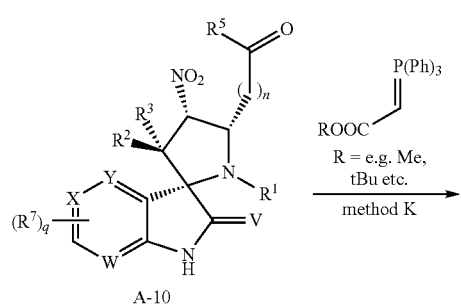

A-10

R = e.g. Me, tBu etc.
method K

Novel compounds of structure (I) can be prepared stepwise starting with a synthesis route depicted in scheme 1 from compounds A-1 via a decarboxylative 1,3 dipolar cycloaddition with an amino acid A-2 (method A) or A-6 (method D) and a nitro ethene A-3 to build up spiro systems A-4 and A-7 as a racemic mixture potentially along with other regio- and/or diastereoisomers of A-4 and A-7. The enantiomers of A-4 and A-7 can be separated at this stage by chiral SFC or alternatively the racemic mixture can be separated at any later stage of the synthesis. Also all other means known for separation of enantiomers can be applied here or after any later synthetic step herein described, e.g. crystallisation, chiral resolution, chiral HPLC etc. (see also *Enantiomers, racemates, and resolutions*, Jean Jacques, André Collet, Samuel H Wilen John Wiley and Sons, NY, 1981).

A-4 and A-7 can be reacted with aldehydes or ketones in a reductive amination reaction to give A-5 (method B) and A-8 (method E). Alternatively, an alkylation or addition reaction can be performed with A-4 and A-7 to obtain intermediates A-5 and A-8.

Intermediate A-5 can be reduced with DIBAL or another reducing reagent and will than also yield intermediates A-8 (method C). Alternatively, intermediate A-5 can be reacted with metallorganic reagents like GRIGNARD reagents etc. to yield intermediates A-8.

The nitro group in intermediate A-8 (scheme 2) can be reduced to the primary amine by reduction with indium metal and hydrochloric acid or an alternative reduction method like hydrogenation under RANEY nickel catalysis or others, to get to intermediates with the structure A-9. Alternatively, intermediates A-9 can also be obtained by oxidation of the hydoxy group in A-8, e.g. with IBX or an alternative oxidizing reagent, to the corresponding carbonyl compound A-10 which can be further reacted with nucleophiles, especially organometallic reagents like GRIGNARD or organo-zinc reagents to intermediate A-11. Intermediate A-11 can be reacted/reduced to A-9 analogous to the transformation from A-8 to A-9.

Intermediate A-9 (scheme 3) can undergo intramolecular cyclization to compounds (I) according to the invention with $R^4$=hydrogen by a MITSUNOBU reaction with triphenylposphine and DEAD or alternative methods.

Intermediate A-10 (scheme 4), alternatively, can be subjected to a WITTIG reaction or other olefination reactions to prepare intermediate A-12 which can be transformed to compounds (I) according to the invention with $R^4$=hydrogen and $R^6$=—$CH_2CO_2H$ by a cascade reaction which is started by the reduction of the nitro group to the primary amine by reaction with indium metal and hydrochloric acid followed by a ring closing Aza-MICHAEL reaction and hydrolysis of the ester to the carboxylic acid if necessary.

Compounds (I) which are obtained from A-9 or A-12 after intramolecular cyclization can be derivatized in optional derivatization steps not explicitly depicted in the schemes in all residues, especially in $R^4$ and $R^6$, if they carry functional groups, that can be further modified such as e.g. halogen atoms, amino and hydroxy groups (including cyclic amines), carboxylic acid or ester functions, nitrils etc. to further compounds (I) by well established organic chemical transformations such as metal-catalyzed cross coupling reactions, acylation, amidation, addition, reduction or (reductive) alkylation or cleavage of protecting groups. These additional steps are not depicted in the general schemes. Likewise, it is also possible to include these additional steps in the synthetic routes depicted in the general schemes, i.e. to carry out derivatization reactions with intermediate compounds. In addition, it may also be possible that building blocks bearing protecting groups are used, i.e. further steps for deprotection are necessary.

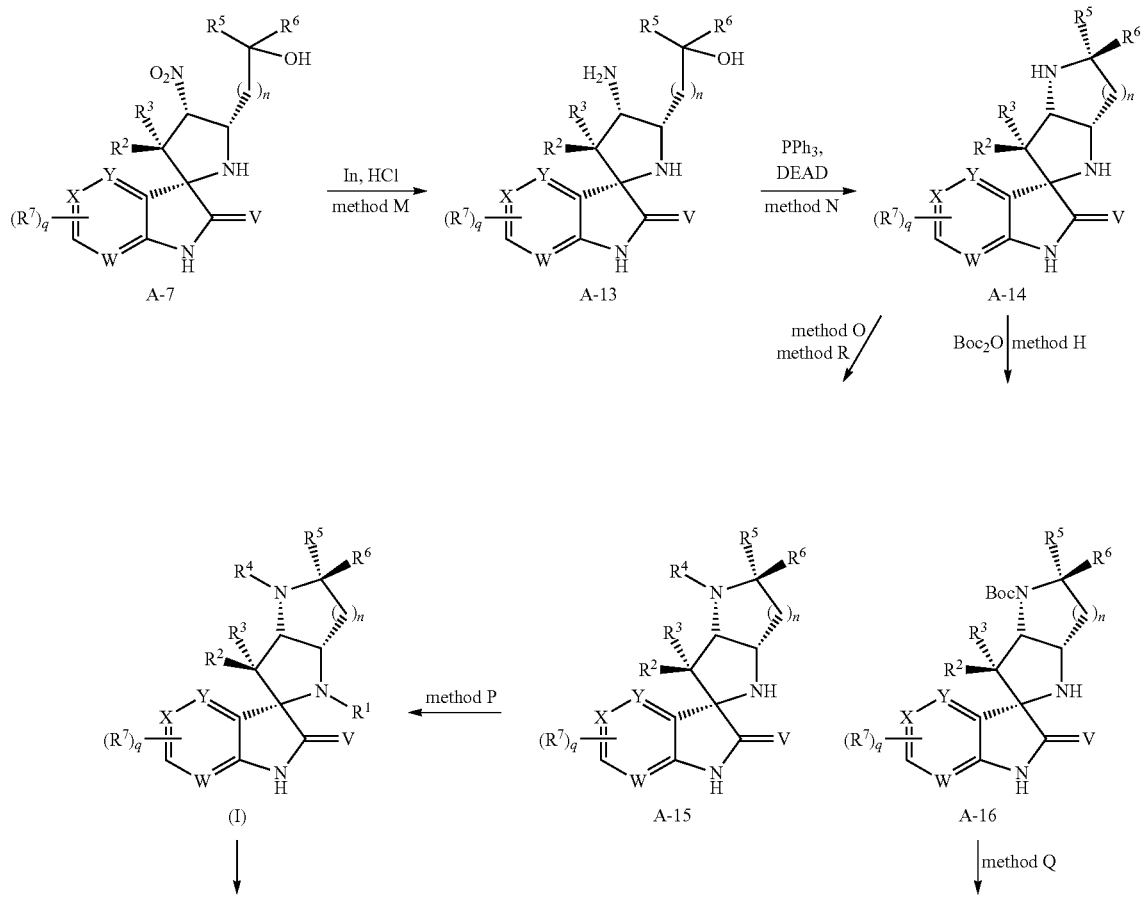

Scheme 5

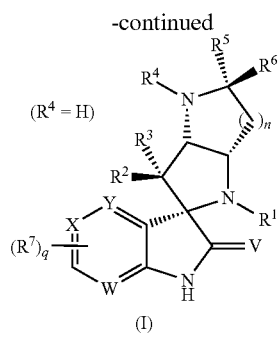 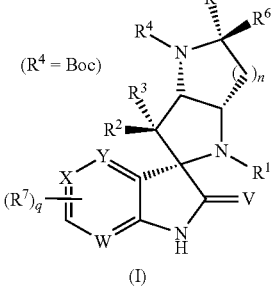

In a further approach the nitro group of intermediate A-7 can be reduced analogous to the transformation from A-8 to A-9 to generate intermediate A-13 which can be subjected to an intramolecular MITSUNOBU reaction to generate cyclic diamine intermediate A-14.

Intermediate A-14 can be Boc-protected to give intermediate A-16 which can be reacted with aldehydes in a reductive amination reaction to give Boc-protected compounds (I). Alternatively, A-16 can undergo an alkylation or addition reaction to obtain Boc-protected (I). The Boc-protecting group can be removed by TFA or another method to the free amine compounds (I) with $R^1$=hydrogen.

Alternatively, intermediate A-14 can be reacted with aldehydes in a reductive amination reaction or other reagents to achieve selective alkylation, addition, acylation or sulfonylation reactions to generate intermediate A-15 which can be further modified by an additional reaction like a reductive amination, alkylation, addition, acylation or sulfonylation to get to compounds (I) according to the invention. The sequence from intermediate A-14 via intermediate A-15 to compounds (I) may also be done in a sequential one-pot procedure.

Here once again compounds (I) which are obtained from A-15 or A-16 can be derivatized in optional derivatization steps not explicitly depicted in the schemes in all residues, especially in $R^4$ and $R^6$, if they carry functional groups, that can be further modified such as e.g. halogen atoms, amino and hydroxy groups (including cyclic amines), carboxylic acid or ester functions, nitrils etc. to further compounds (I) by well established organic chemical transformations such as metal-catalyzed cross coupling reactions, acylation, amidation, addition, reduction or (reductive) alkylation or cleavage of protecting groups. Likewise, it is also possible to include these additional steps in the synthetic routes, i.e. to carry out derivatization reactions with intermediate compounds. In addition, it may also be possible that building blocks bearing protecting groups are used, i.e. further steps for deprotection are necessary.

Compounds (I) have been tested for their activity to affect MDM2-p53 interaction in their racemic form or alternatively as the enantiopure form. Each of the two enantiomers of a racemic mixture may have activity against MDM2 although with a different binding mode. Enantiopure compounds are marked with the label "Chiral". Compounds listed in any table below that are labled "Chiral" (both intermediates and compounds according to the invention) are separated by SFC chromatography from their enantiomer or are synthesized from enantiopure starting material which is separated by SFC.

Example

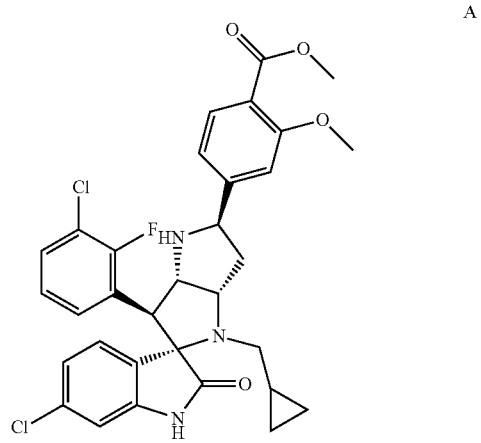

A

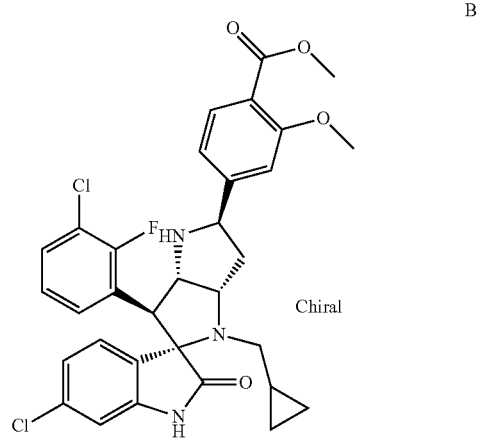

B

Chiral

-continued

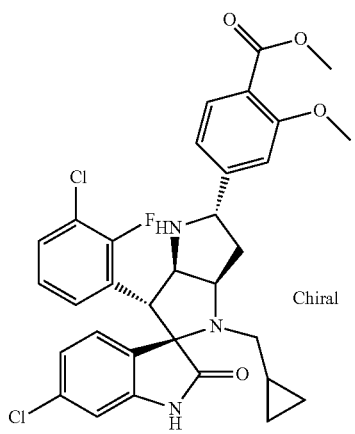

C

Structure A defines the racemic mixture of compounds with structure B and C, i.e. structure A encompasses two structures (compounds B and C), whereas structures B and C, respectively, are enantiopure and only define one specific compound. Thus, formulae (I) and (Ia)

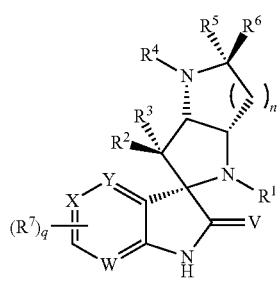

(I)

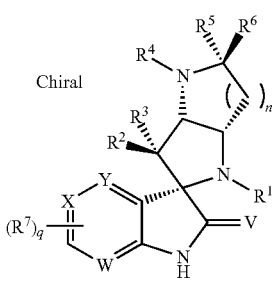

(Ia)

with a set of specific definitions for groups $R^1$ to $R^7$, V, W, X, Y, n and q represent the racemic mixture of two enantiomers (→(I); structure A above is one specific example of such a racemic mixture) or a single enantiomer (→(Ia); structure B above is one specific enantiomer). The same definition applies to synthetic intermediates.

Synthesis of Intermediate A-4 (Method A)
Experimental Procedure for the Synthesis of A-4a

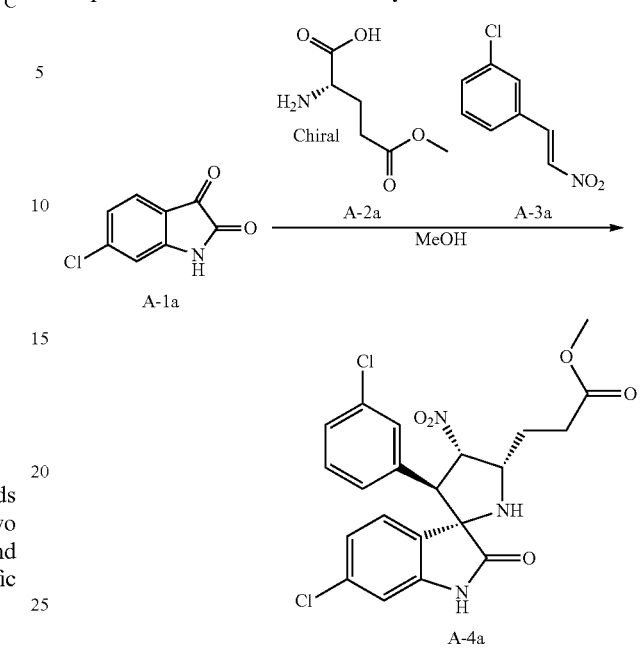

6-Chloroisatin A-1a (1.50 g, 8.3 mmol), 1-(3-chlorophenyl)-2-nitroethene (1.52 g, 8.3 mmol) and L-glutamic acid-5-methylester (1.33 g, 8.3 mmol) are refluxed in MeOH for 60 min. The reaction mixture is concentrated in vacuo and purified by chromatography if necessary.

The following intermediates A-4 (table 1) are available in an analogous manner starting from different annulated 1H-pyrrole-2,3-diones A-1, amino acids A-2 and nitroethenes A-3.

TABLE 1

| # | structure | $t_{ret}$ [min] | $[M + H]^+$ | HPLC method |
|---|---|---|---|---|
| A-4a | 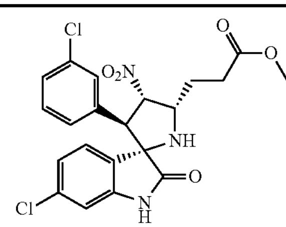 | 1.35 | 464 | A |
| A-4b | 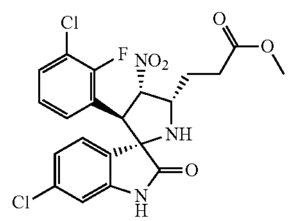 [SMILES: COC(=O)CC[C@@H]1N[C@@]2(C(=O)Nc3cc(Cl)ccc32)[C@@H](c2cccc(Cl)c2F)[C@@H]1[N+](=O)[O-]] | 1.42 | 482 | A |
| A-4c | 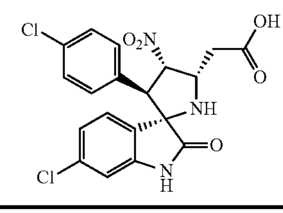 | 0.93 | 436 | A |

Synthesis of Intermediate A-5 (Method B)
Experimental Procedure for the Synthesis of A-5a

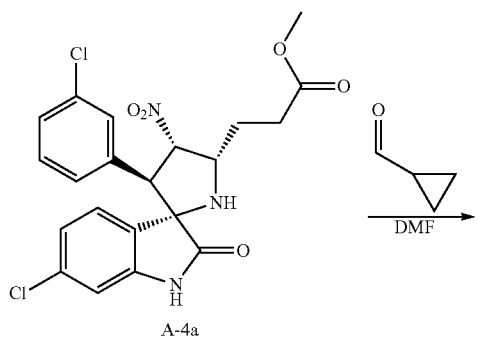

A-4a

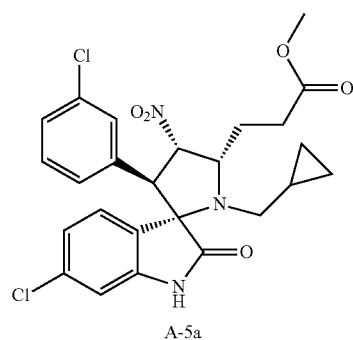

A-5a

To a solution of cyclopropanecarbaldehyde (0.48 g, 6.5 mmol) in DMF is added intermediate A-4a (1.50 g, 3.2 mmol) and AcOH (0.37 mL) and the reaction mixture is stirred at rt for 45 min. Sodium triacetoxyborohydride (2.74 g, 12.9 mmol) is added and the reaction mixture is stirred at rt overnight. Water is added to the reaction mixture and it is extracted with EtOAc. The combined organic layer is dried (MgSO$_4$), filtered, concentrated in vacuo and the crude product is purified by chromatography if necessary.

The following intermediates A-5 (Table 2) are available in an analogous manner starting from different intermediates A-4.

TABLE 2

| # | structure | $t_{ret}$ [min] | [M + H]$^+$ | HPLC method |
|---|---|---|---|---|
| A-5a | 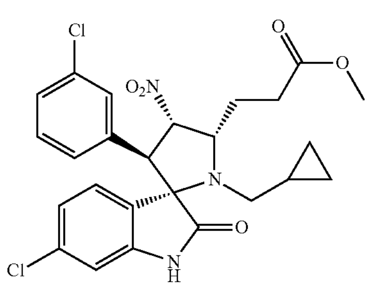 [SMILES: COC(=O)CC[C@H]1[C@@H]([N+](=O)[O-])[C@H](c2cccc(Cl)c2)[C@]2(C(=O)Nc3cc(Cl)ccc32)N1CC1CC1] | 0.88 | 518 | B |
| A-5b | | 0.94 | 536 | F |

Synthesis of Intermediate A-8 (Method C)
Experimental Procedure for the Synthesis of A-8a

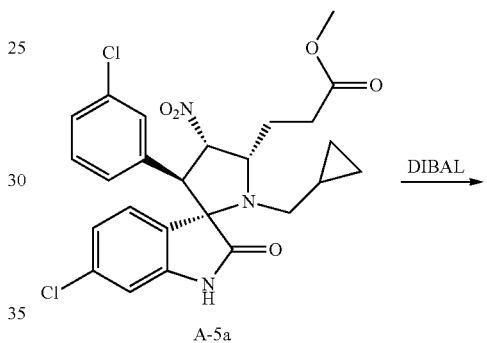

A-5a

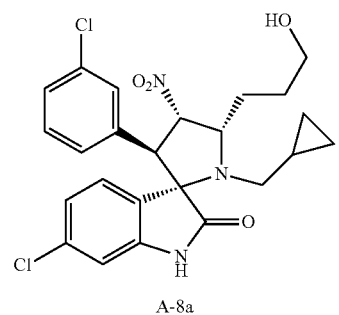

A-8a

To a solution of A-5a (0.23 g, 0.44 mmol) in DCM is added DIBAL (1.77 mL, 1.78 mmol, 1.0 M in DCM) slowly at 0° C. and the reaction mixture is stirred for 1 h. To the reaction mixture is added water and saturated aqueous potassium sodium tartrat solution and the mixture is stirred overnight at rt. The phases are separated and the aqueous phase is extracted with DCM. The combined organic layer is dried (MgSO$_4$), filtered, concentrated in vacuo and used without further purification in the next step.

The following intermediates A-8 (Table 3) are available in an analogous manner starting from different intermediates A-5.

TABLE 3

| # | structure | $t_{ret}$ [min] | [M+H]$^+$ | HPLC method |
|---|---|---|---|---|
| A-8a | 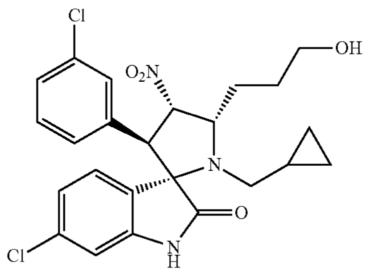 [SMILES: O=C1Nc2cc(Cl)ccc2[C@@]12[C@@H](c1cccc(Cl)c1)[C@H]([N+](=O)[O-])[C@H](CCCO)N2CC1CC1] | 0.77 | 490 | B |
| A-8b | 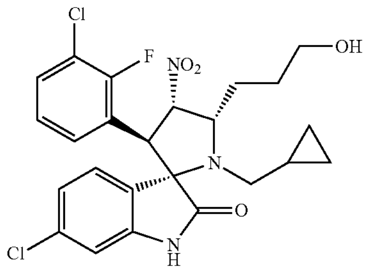 [SMILES: O=C1Nc2cc(Cl)ccc2[C@@]12[C@@H](c1cccc(Cl)c1F)[C@H]([N+](=O)[O-])[C@H](CCCO)N2CC1CC1] | 1.52 | 508 | A |

Synthesis of Intermediate A-7 (Method D)

Experimental Procedure for the Synthesis of A-7a

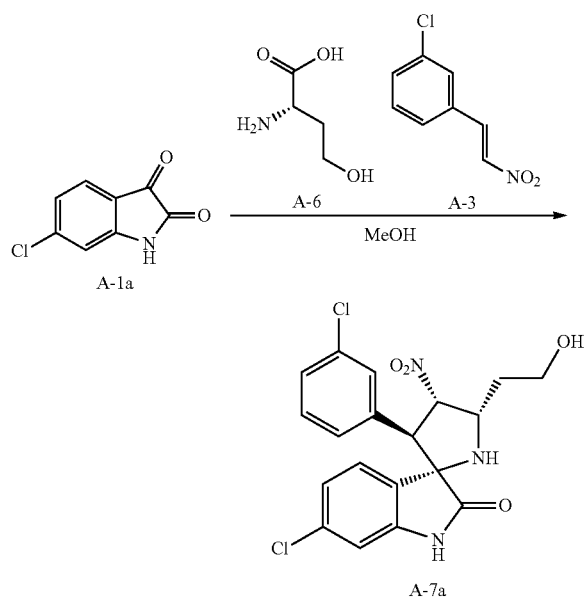

6-Chloroisatin A-1a (1.00 g, 5.4 mmol), 1-(3-chlorophenyl)-2-nitroethene (0.99 g, 5.4 mmol) and L-homoserine (0.64 g, 5.4 mmol) are refluxed in MeOH for 40 min. The reaction mixture is concentrated in vacuo and purified by chromatography if necessary.

The following intermediates A-7 (table 4) are available in an analogous manner starting from different annulated 1H-pyrrole-2,3-diones A-1, amino acids A-6 and nitroethenes A-3.

TABLE 4

| # | structure | $t_{ret}$ [min] | [M+H]$^+$ | HPLC method |
|---|---|---|---|---|
| A-7a | 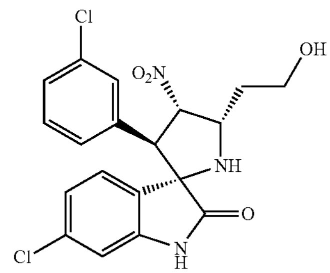 [SMILES: O=C1Nc2cc(Cl)ccc2[C@]12N[C@@H](CCO)[C@@H]([N+](=O)[O-])[C@@H]2c1cccc(Cl)c1] | 1.17 | 422 | A |
| A-7b | 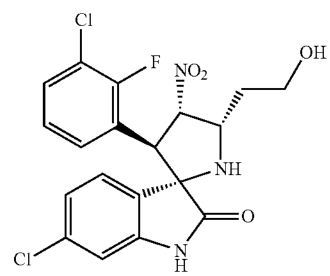 | 1.21 | 440 | A |
| A-7c | 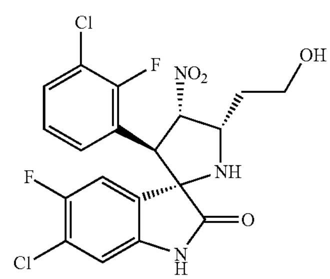 [SMILES: O=C1Nc2cc(Cl)c(F)cc2[C@]12N[C@@H](CCO)[C@@H]([N+](=O)[O-])[C@@H]2c1cccc(Cl)c1F] | 1.25 | 458 | A |
| A-7d | 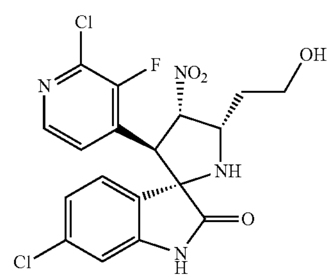 [SMILES: O=C1Nc2cc(Cl)ccc2[C@]12N[C@@H](CCO)[C@@H]([N+](=O)[O-])[C@@H]2c1ccnc(Cl)c1F] | 0.55 | 441 | C |
| A-7e | 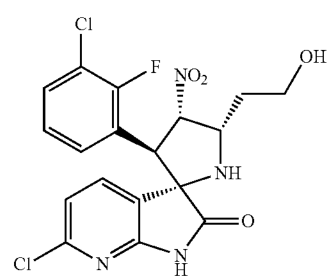 [SMILES: O=C1Nc2nc(Cl)ccc2[C@]12N[C@@H](CCO)[C@@H]([N+](=O)[O-])[C@@H]2c1cccc(Cl)c1F] | 1.13 | 441 | A |

TABLE 4-continued

| # | structure | $t_{ret}$ [min] | [M + H]$^+$ | HPLC method |
|---|---|---|---|---|
| A-7f | (Chiral structure shown) | 1.21 | 440 | A |

Synthesis of Intermediate A-8 (Method E)
Experimental Procedure for the Synthesis of A-8c

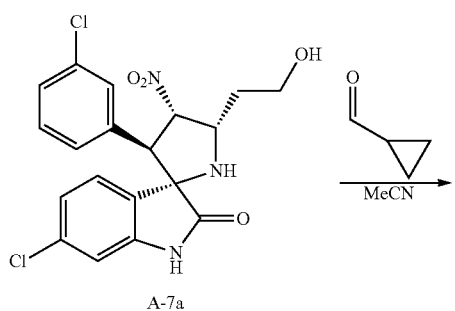

A-7a

To a solution of cyclopropanecarbaldehyde (0.22 g, 3.2 mmol) in acetonitrile is added intermediate A-7a (1.60 g, 3.8 mmol) and AcOH (1.5 mL) and the reaction mixture is stirred for 15 min. Sodium triacetoxyborohydride (1.34 g, 6.3 mmol) is added and the reaction mixture is stirred overnight. Water is added to the reaction mixture and it is extracted with DCM. The combined organic layer is dried (MgSO$_4$), filtered, concentrated in vacuo and the crude product is purified by chromatography if necessary.

The following intermediates A-8 (table 5) are available in an analogous manner starting from different intermediates A-7 and aldehydes.

TABLE 5

| # | structure | $t_{ret}$ [min] | [M + H]$^+$ | HPLC method |
|---|---|---|---|---|
| A-8c | (structure shown) | 1.37 | 476 | A |
| A-8d | (structure shown) | 1.38 | 494 | A |

TABLE 5-continued
| # | structure | $t_{ret}$ [min] | $[M + H]^+$ | HPLC method |
|---|---|---|---|---|
| A-8e | 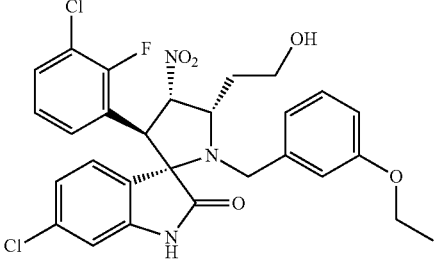 [SMILES: CCOc1cccc(CN2[C@@H](CCO)[C@@H]([N+](=O)[O-])[C@H](c3cccc(Cl)c3F)[C@]23C(=O)Nc2cc(Cl)ccc23)c1] | 1.47 | 574 | A |
| A-8f | 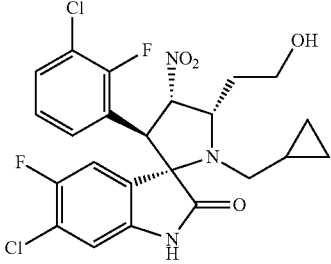 [SMILES: O=C1Nc2cc(Cl)c(F)cc2[C@@]12[C@@H](c1cccc(Cl)c1F)[C@H]([N+](=O)[O-])[C@H](CCO)N2CC1CC1] | 1.38 | 512 | A |
| A-8g | 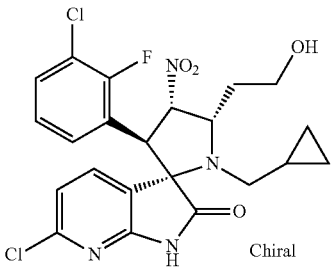 | 1.29 | 495 | A |
| A-8h | 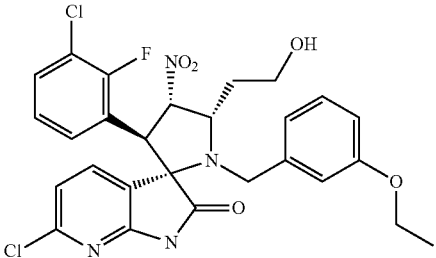 [SMILES: CCOc1cccc(CN2[C@@H](CCO)[C@@H]([N+](=O)[O-])[C@H](c3cccc(Cl)c3F)[C@]23C(=O)Nc2nc(Cl)ccc23)c1] | 0.80 | 575 | E |
| A-8i | 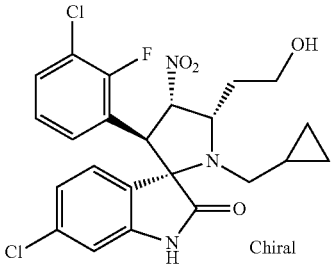 | 1.38 | 494 | A |

Synthesis of Intermediate A-9 (Method F)
Experimental Procedure, for the Synthesis of A-9a

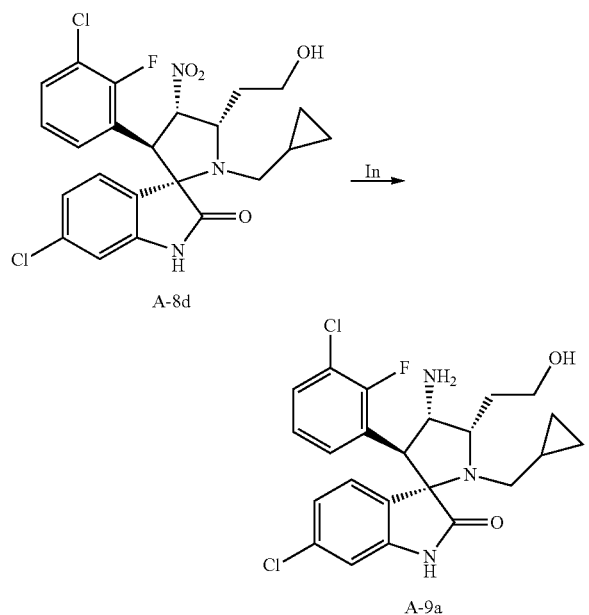

To a solution of A-8d (100 mg, 0.20 mmol) in a mixture of water and THF is added indium powder (93 mg, 0.81 mmol) and conc. HCl (120 mg, 1.21 mmol) and the reaction mixture is stirred for 2 h at rt. Water is added to the reaction mixture and it is extracted with ethyl acetate. The combined organic layer is dried (MgSO$_4$), filtered, concentrated in vacuo and the crude product is purified by chromatography if necessary.

The following intermediates A-9 (table 6) are available in an analogous manner starting from different intermediates A-8.

TABLE 6

| # | structure | $t_{ret}$ [min] | [M + H]$^+$ | HPLC method |
|---|---|---|---|---|
| A-9a | 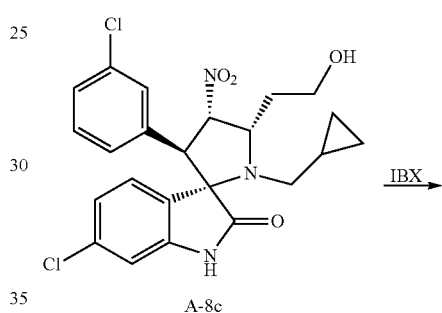 | 0.66 | 464 | D |
| A-9b | Chiral | 0.66 | 464 | D |

TABLE 6-continued

| # | structure | $t_{ret}$ [min] | [M + H]$^+$ | HPLC method |
|---|---|---|---|---|
| A-9c | 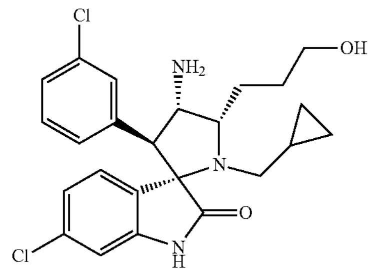 [SMILES: N[C@@H]1[C@H](CCCO)N(CC2CC2)[C@@]2(C(=O)Nc3cc(Cl)ccc32)[C@H]1c1cccc(Cl)c1] | 0.65 | 460 | B |

Synthesis of Intermediate A-10 (Method H)
Experimental Procedure for the Synthesis of A-10a

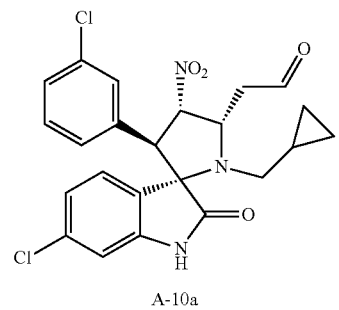

To a solution of A-8c (100 mg, 0.21 mmol) in a MeCN is added IBX (76 mg, 0.27 mmol) and the reaction mixture is stirred for 30 min at 75° C. The reaction mixture is cooled to rt, filtered through Celite® and concentrated in vacuo. The product is used without further purification for the next step.

The following intermediates A-10 (table 7) are available in an analogous manner starting from different intermediates A-8.

TABLE 7

| # | structure | t_ret [min] | [M + H]+ | HPLC method |
|---|---|---|---|---|
| A-10a | 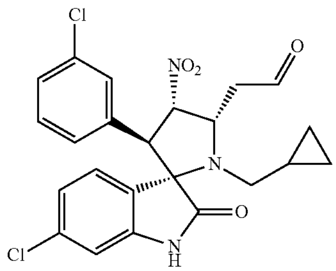 [SMILES: O=CC[C@H]1[C@@H]([N+](=O)[O-])[C@H](c2cccc(Cl)c2)[C@]2(C(=O)Nc3cc(Cl)ccc32)N1CC1CC1] | 1.46 | 474 | A |
| A-10b | 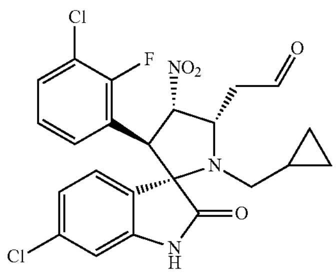 | 1.47 | 492 | A |
| A-10c | 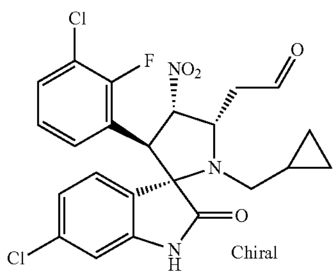 | 0.85 | 492 | B |
| A-10d | 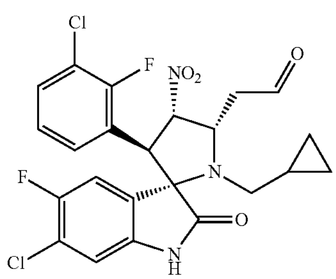 [SMILES: O=CC[C@H]1[C@@H]([N+](=O)[O-])[C@H](c2cccc(Cl)c2F)[C@]2(C(=O)Nc3cc(Cl)c(F)cc32)N1CC1CC1] | 0.84 | 510 | B |
| A-10e | 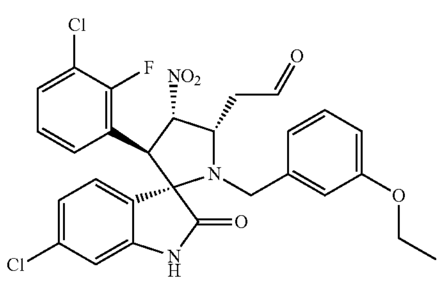 [SMILES: CCOc1cccc(CN2[C@@H](CC=O)[C@@H]([N+](=O)[O-])[C@H](c3cccc(Cl)c3F)[C@]23C(=O)Nc2cc(Cl)ccc23)c1] | 0.91 | 572 | B |

TABLE 7-continued
| # | structure | $t_{ret}$ [min] | $[M + H]^+$ | HPLC method |
|---|---|---|---|---|
| A-10f | 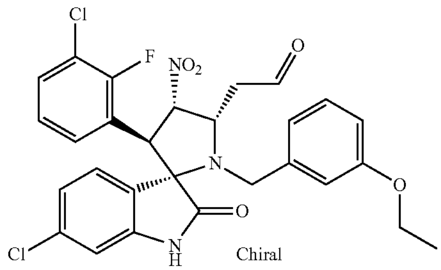 | 0.88 | 572 | C |
| A-10g | 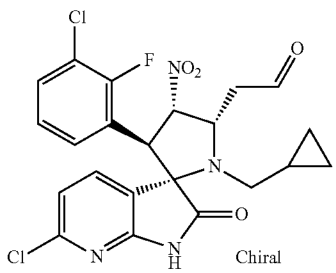 | | | |
| A-10h | 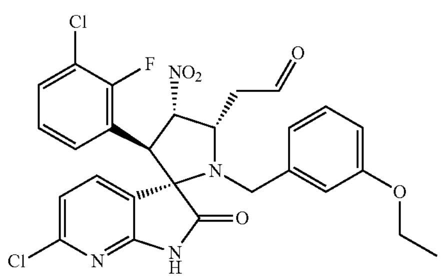 [SMILES: CCOc1cccc(CN2[C@@H](CC=O)[C@@H]([N+](=O)[O-])[C@H](c3cccc(Cl)c3F)[C@]23C(=O)Nc2nc(Cl)ccc23)c1] | | | |
Synthesis of Spiroindolinone A-11 (Method I)
Experimental Procedure for the Synthesis of A-11a and A-11b
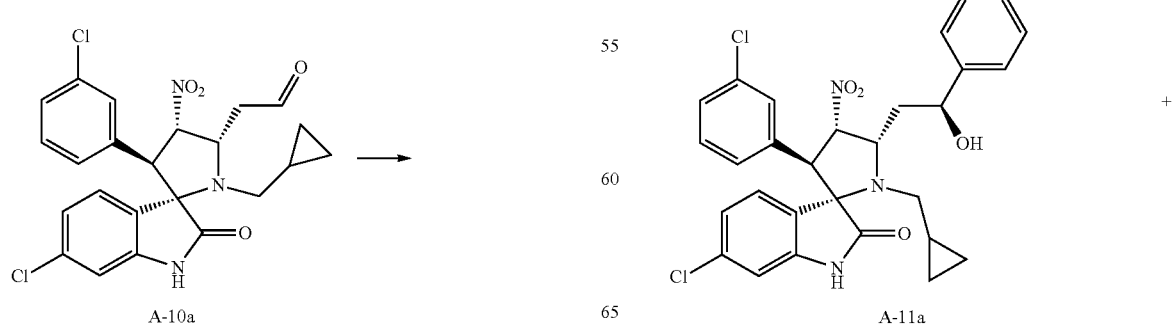

-continued

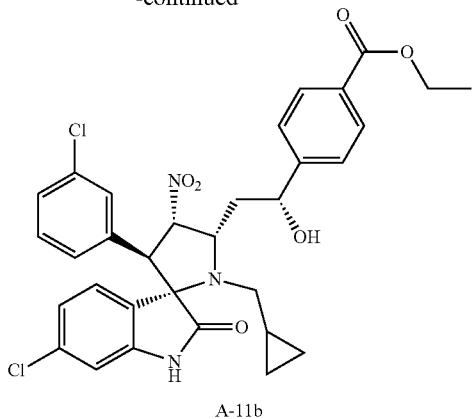

A-11b

To a solution of ethyl 4-iodobenzoate (0.21 mL, 1.25 mmol) in dry THF under argon atmosphere at −40° C. is added isopropylmagnesium chloride lithium chloride complex (0.9625 mL, 1.25 mmol, 1.3 M in THF) dropwise and the reaction mixture is stirred for 1 h. A solution of aldehyde A-10a (198 mg, 0.417 mmol) in THF is added slowly at −40° C. and the reaction mixture is stirred for 1.5 h. Water and Et$_2$O is added to the reaction mixture and the phases are separated. The aqueous phase is extracted with Et$_2$O and the combined organic layer is dried (MgSO$_4$), filtered, concentrated in vacuo. The crude product is purified by chromatography.

The following intermediates A-11 (table 8) are available in an analogous manner starting from different intermediates A-10 and different iodo compounds.

TABLE 8

| # | structure | $t_{ret}$ [min] | [M + H]$^+$ | HPLC method |
|---|-----------|-----------------|-------------|-------------|
| A-11a | 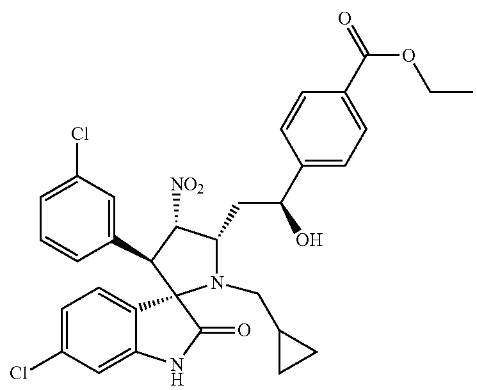 [SMILES: CCOC(=O)c1ccc([C@@H](O)C[C@H]2[C@@H]([N+](=O)[O-])[C@H](c3cccc(Cl)c3)[C@]3(C(=O)Nc4cc(Cl)ccc43)N2CC2CC2)cc1] | 1.60 | 624 | A |
| A-11b | 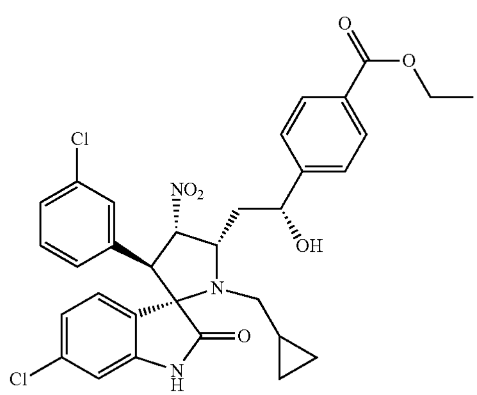 [SMILES: CCOC(=O)c1ccc([C@H](O)C[C@H]2[C@@H]([N+](=O)[O-])[C@H](c3cccc(Cl)c3)[C@]3(C(=O)Nc4cc(Cl)ccc43)N2CC2CC2)cc1] | 1.64 | 624 | A |

TABLE 8-continued

| # | structure | t_ret [min] | [M + H]+ | HPLC method |
|---|---|---|---|---|
| A-11c | 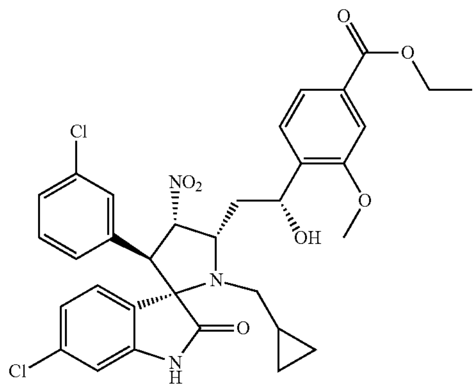 [SMILES: CCOC(=O)c1ccc([C@H](O)C[C@H]2[C@@H]([N+](=O)[O-])[C@H](c3cccc(Cl)c3)[C@]3(C(=O)Nc4cc(Cl)ccc43)N2CC2CC2)c(OC)c1] | 1.66 | 603 | A |
| A-11d | 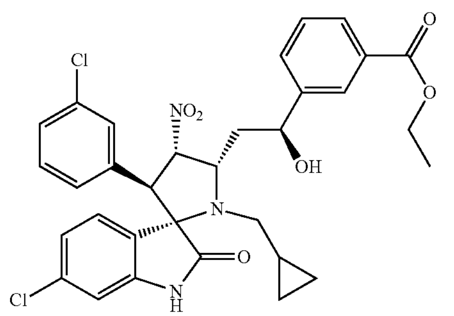 [SMILES: CCOC(=O)c1cccc([C@@H](O)C[C@H]2[C@@H]([N+](=O)[O-])[C@H](c3cccc(Cl)c3)[C@]3(C(=O)Nc4cc(Cl)ccc43)N2CC2CC2)c1] | 1.60 | 624 | A |
| A-11e | 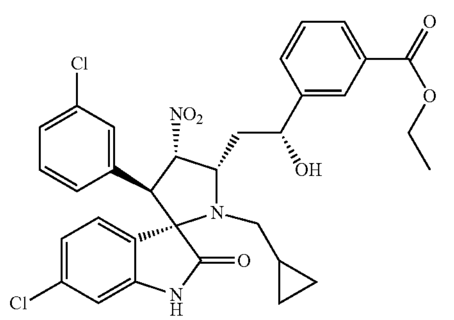 [SMILES: CCOC(=O)c1cccc([C@H](O)C[C@H]2[C@@H]([N+](=O)[O-])[C@H](c3cccc(Cl)c3)[C@]3(C(=O)Nc4cc(Cl)ccc43)N2CC2CC2)c1] | 1.65 | 624 | A |
| A-11f | 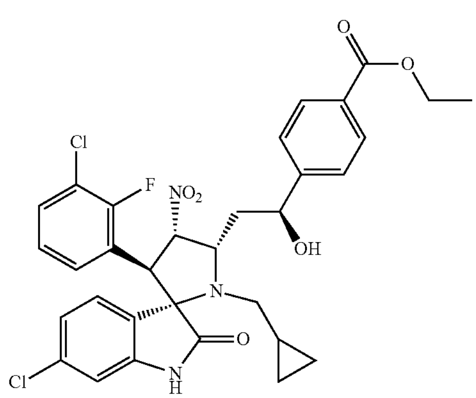 [SMILES: CCOC(=O)c1ccc([C@@H](O)C[C@H]2[C@@H]([N+](=O)[O-])[C@H](c3cccc(Cl)c3F)[C@]3(C(=O)Nc4cc(Cl)ccc43)N2CC2CC2)cc1] | 1.60 | 642 | A |

TABLE 8-continued

| # | structure | $t_{ret}$ [min] | $[M + H]^+$ | HPLC method |
|---|---|---|---|---|
| A-11g | 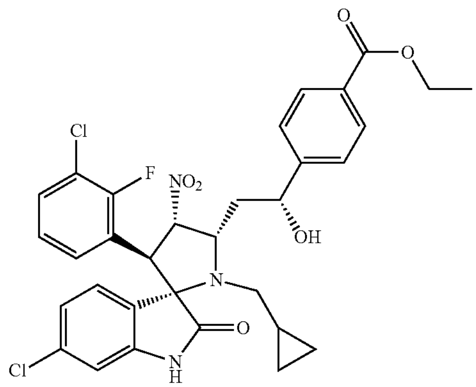 [SMILES: CCOC(=O)c1ccc([C@H](O)C[C@H]2[C@@H]([N+](=O)[O-])[C@H](c3cccc(Cl)c3F)[C@]3(C(=O)Nc4cc(Cl)ccc43)N2CC2CC2)cc1] | 642 | 1.65 | A |
| A-11h | 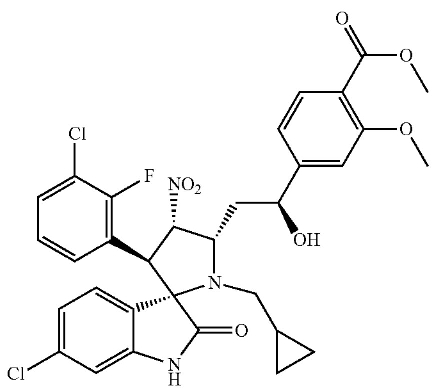 [SMILES: COC(=O)c1ccc([C@@H](O)C[C@H]2[C@@H]([N+](=O)[O-])[C@H](c3cccc(Cl)c3F)[C@]3(C(=O)Nc4cc(Cl)ccc43)N2CC2CC2)cc1OC] | 658 | 1.62 | A |
| A-11i | 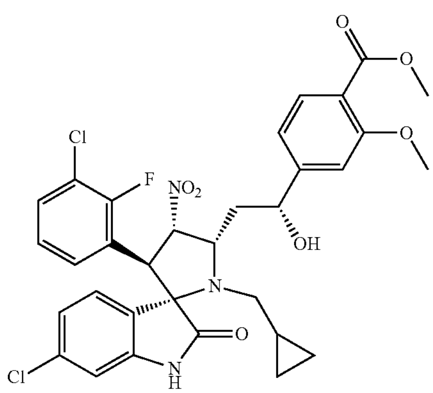 [SMILES: COC(=O)c1ccc([C@H](O)C[C@H]2[C@@H]([N+](=O)[O-])[C@H](c3cccc(Cl)c3F)[C@]3(C(=O)Nc4cc(Cl)ccc43)N2CC2CC2)cc1OC] | 658 | 1.67 | A |
| A-11j | (Chiral) | 1.60 | 642 | A |

TABLE 8-continued
| # | structure | $t_{ret}$ [min] | $[M + H]^+$ | HPLC method |
|---|---|---|---|---|
| A-11k | 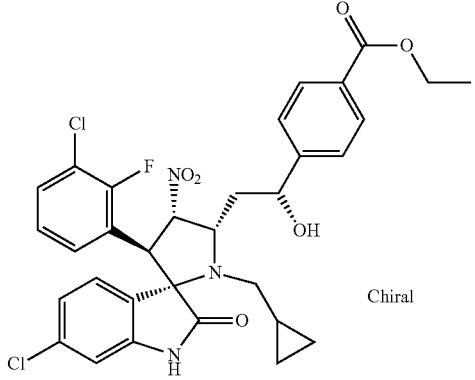 Chiral | 1.65 | 642 | A |
| A-11l | 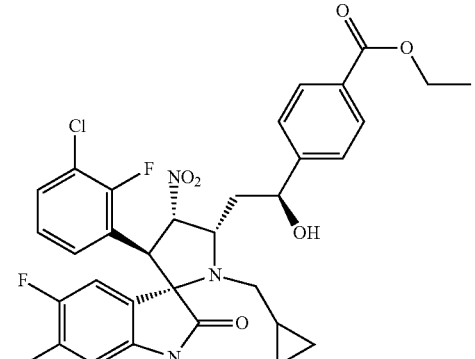 | 0.92 | 660 | B |
| A-11m | 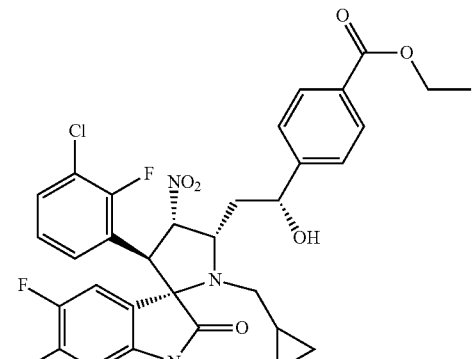 | 0.96 | 660 | B |
| A-11n | 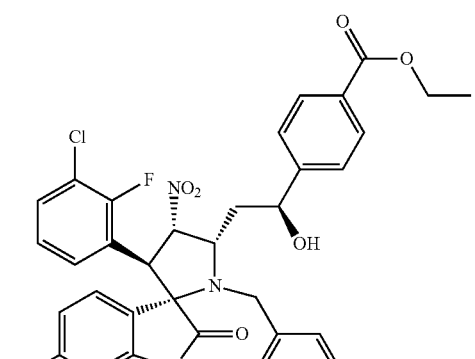 | 1.70 | 722 | A |

TABLE 8-continued
| # | structure | $t_{ret}$ [min] | $[M + H]^+$ | HPLC method |
|---|---|---|---|---|
| A-11o | 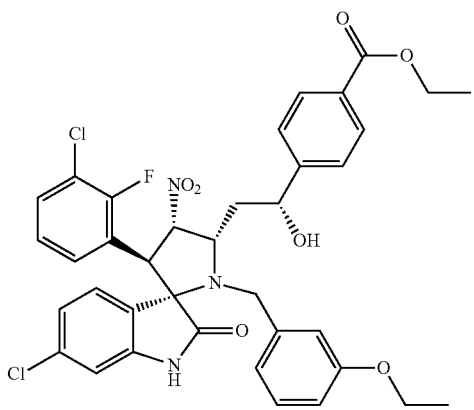 [SMILES: CCOC(=O)c1ccc([C@H](O)C[C@H]2[C@@H]([N+](=O)[O-])[C@H](c3cccc(Cl)c3F)[C@]3(C(=O)Nc4cc(Cl)ccc43)N2Cc2cccc(OCC)c2)cc1] | 1.73 | 722 | A |
| A-11p | 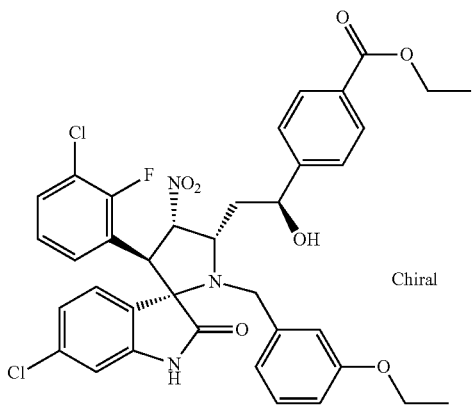 [SMILES: CCOC(=O)c1ccc([C@@H](O)C[C@H]2[C@@H]([N+](=O)[O-])[C@H](c3cccc(Cl)c3F)[C@]3(C(=O)Nc4cc(Cl)ccc43)N2Cc2cccc(OCC)c2)cc1] Chiral | 1.77 | 722 | A |
| A-11q | 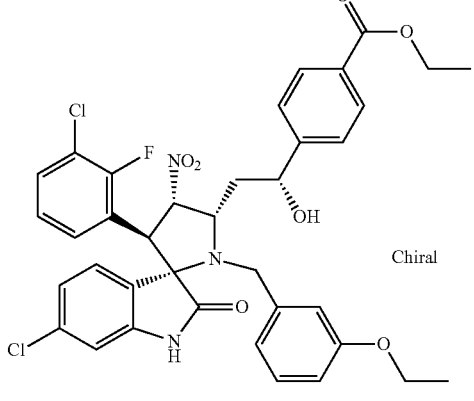 Chiral | 1.80 | 722 | A |

TABLE 8-continued
| # | structure | $t_{ret}$ [min] | $[M + H]^+$ | HPLC method |
|---|---|---|---|---|
| A-11r | 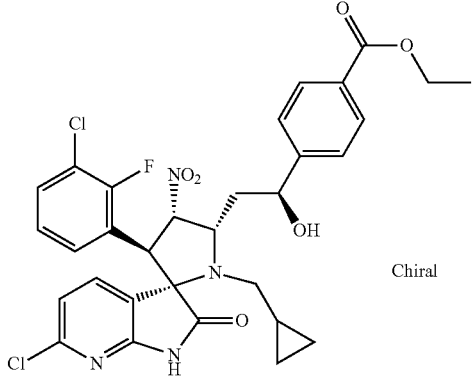 [SMILES: CCOC(=O)c1ccc([C@@H](O)C[C@H]2[C@@H]([N+](=O)[O-])[C@H](c3cccc(Cl)c3F)[C@]3(C(=O)Nc4nc(Cl)ccc43)N2CC2CC2)cc1] Chiral | | | |
| A-11s | 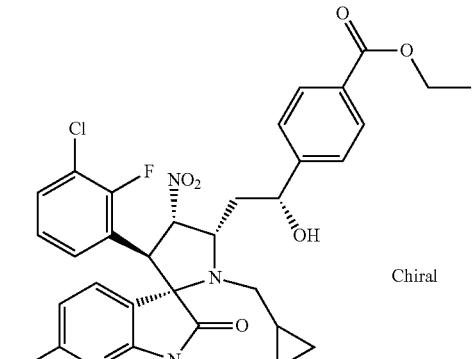 Chiral | | | |
| A-11t | 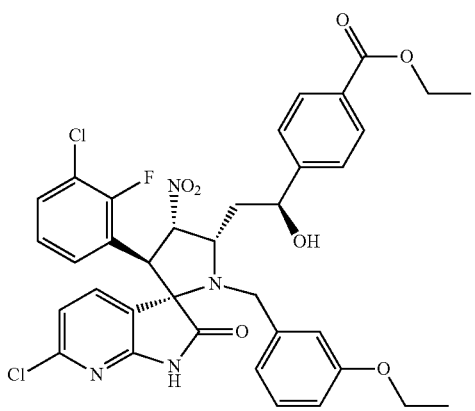 [SMILES: CCOC(=O)c1ccc([C@@H](O)C[C@H]2[C@@H]([N+](=O)[O-])[C@H](c3cccc(Cl)c3F)[C@]3(C(=O)Nc4nc(Cl)ccc43)N2Cc2cccc(OCC)c2)cc1] | | | |
| A-11u | 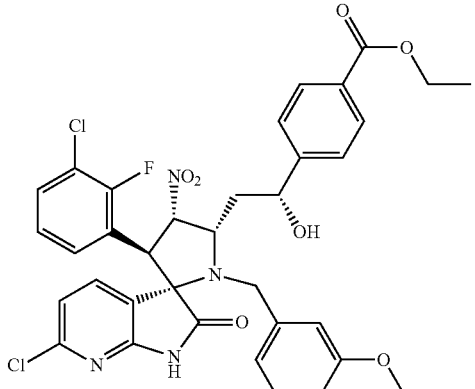 | | | |

TABLE 8-continued

| # | structure | $t_{ret}$ [min] | $[M + H]^+$ | HPLC method |
|---|---|---|---|---|
| A-11v | 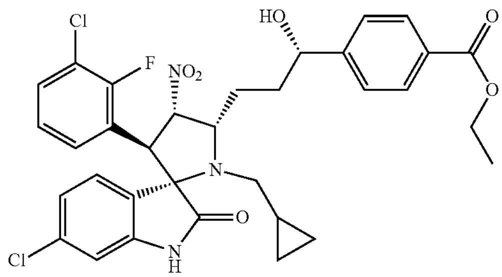 [SMILES: CCOC(=O)c1ccc([C@@H](O)CC[C@H]2[C@@H]([N+](=O)[O-])[C@H](c3cccc(Cl)c3F)[C@]3(C(=O)Nc4cc(Cl)ccc43)N2CC2CC2)cc1] | 1.69 | 656 | A |
| A-11w | 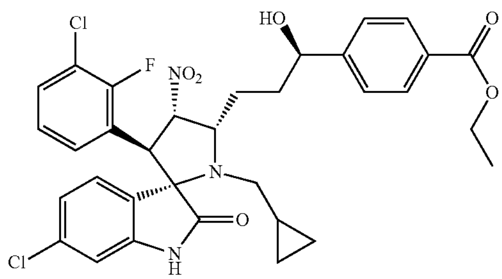 [SMILES: CCOC(=O)c1ccc([C@H](O)CC[C@H]2[C@@H]([N+](=O)[O-])[C@H](c3cccc(Cl)c3F)[C@]3(C(=O)Nc4cc(Cl)ccc43)N2CC2CC2)cc1] | 1.69 | 656 | A |

Synthesis of Intermediate A-9 (Method J)
Experimental Procedure for the Synthesis of A-9c

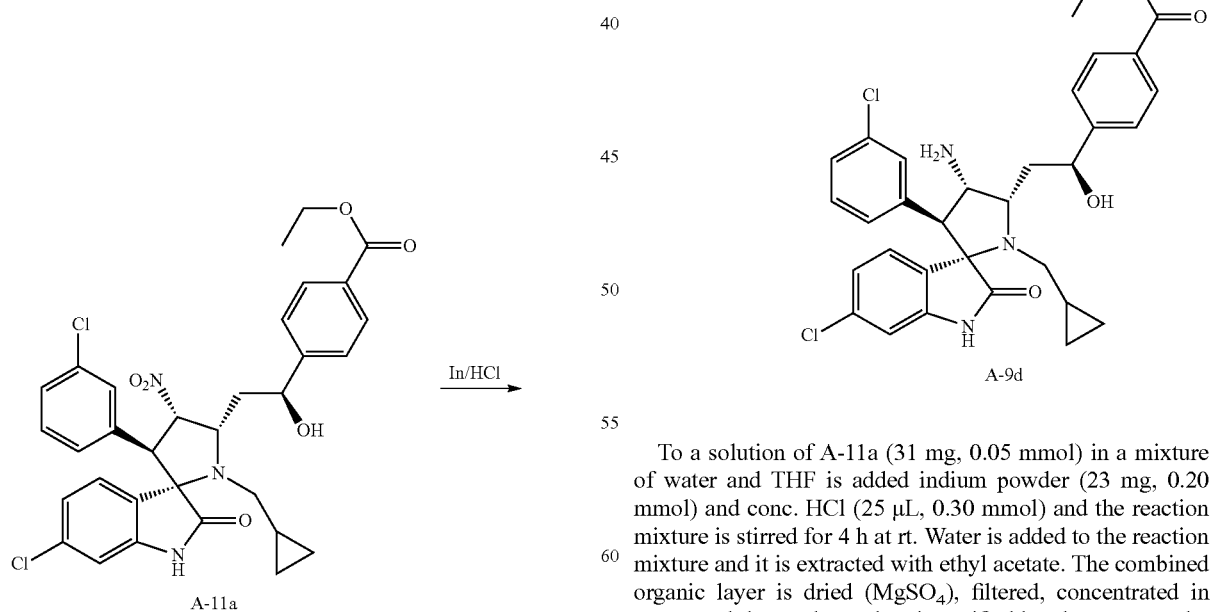

To a solution of A-11a (31 mg, 0.05 mmol) in a mixture of water and THF is added indium powder (23 mg, 0.20 mmol) and conc. HCl (25 μL, 0.30 mmol) and the reaction mixture is stirred for 4 h at rt. Water is added to the reaction mixture and it is extracted with ethyl acetate. The combined organic layer is dried (MgSO$_4$), filtered, concentrated in vacuo and the crude product is purified by chromatography if necessary.

The following intermediates A-9 (table 9) are available in an analogous manner starting from different intermediates A-11.

TABLE 9

| # | structure | $t_{ret}$ [min] | $[M + H]^+$ | HPLC method |
|---|---|---|---|---|
| A-9d | 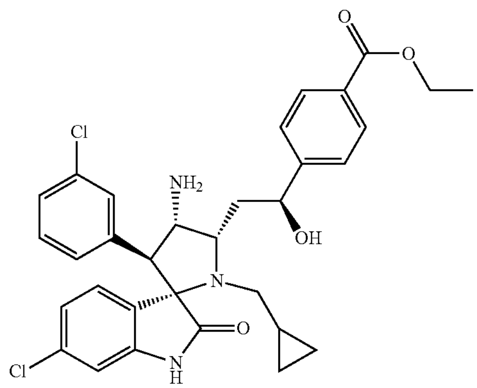 | 0.89 | 594 | B |
| A-9e | 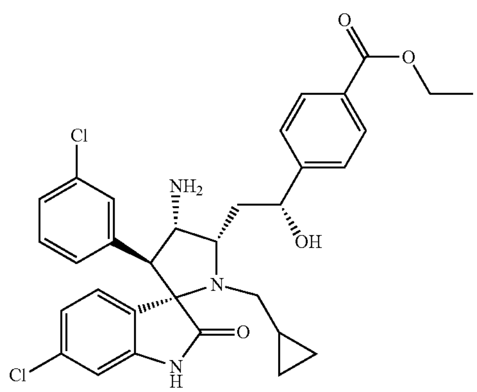 | 0.86 | 594 | B |
| A-9f | 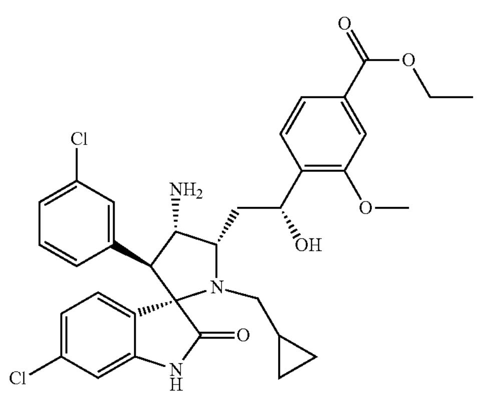 [SMILES: CCOC(=O)c1ccc([C@H](O)C[C@H]2[C@@H](N)[C@H](c3cccc(Cl)c3)[C@]3(C(=O)Nc4cc(Cl)ccc43)N2CC2CC2)c(OC)c1] | 1.52 | 624 | A |
| A-9g | 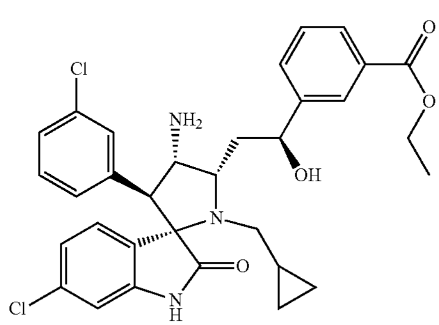 | 0.89 | 594 | B |

TABLE 9-continued

| # | structure | $t_{ret}$ [min] | $[M + H]^+$ | HPLC method |
|---|---|---|---|---|
| A-9h | 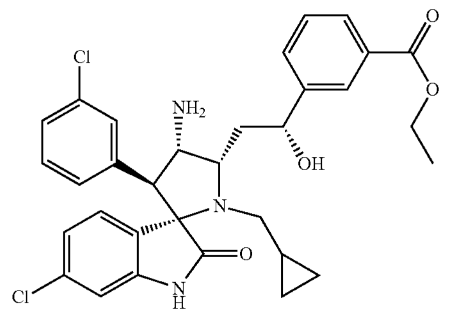 | 0.87 | 594 | B |
| A-9i | 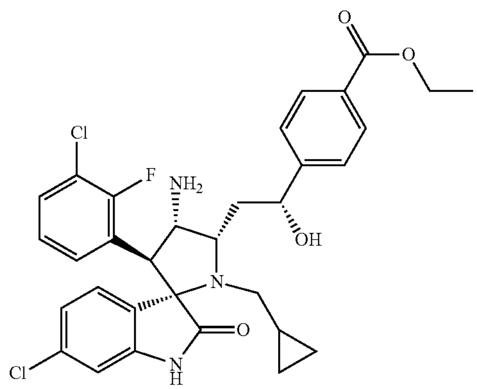 | 0.89 | 612 | B |
| A-9j | 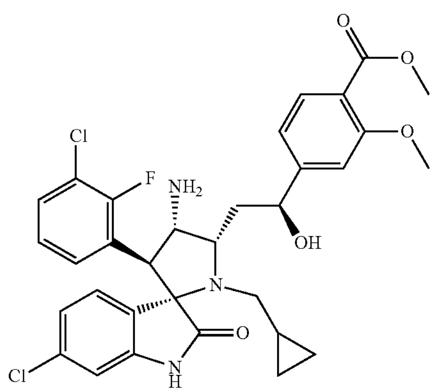 | 0.81 | 628 | B |
| A-9k | (Chiral) | 1.54 | 612 | A |

TABLE 9-continued
| # | structure | $t_{ret}$ [min] | $[M + H]^+$ | HPLC method |
|---|---|---|---|---|
| A-9l | 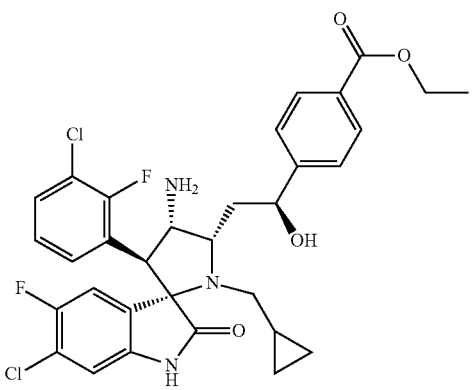 | 1.54 | 630 | A |
| A-9m | 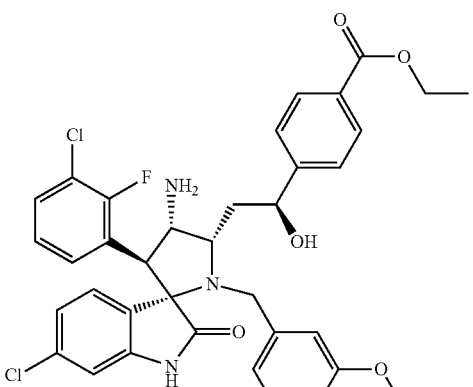 | 0.93 | 692 | B |
| A-9n | 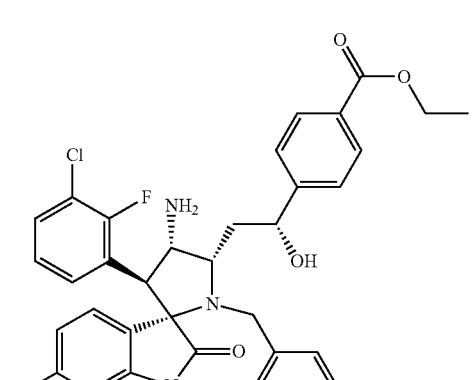 | 0.90 | 692 | B |

TABLE 9-continued
| # | structure | $t_{ret}$ [min] | $[M + H]^+$ | HPLC method |
|---|---|---|---|---|
| A-9o | 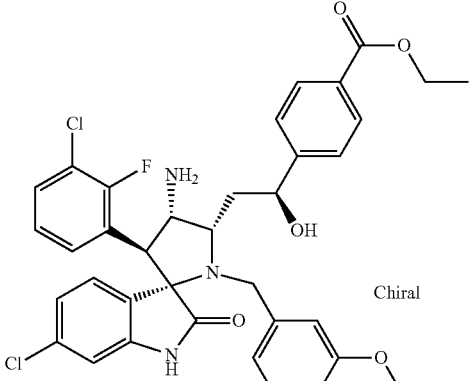 Chiral | 0.93 | 692 | B |
| A-9p | 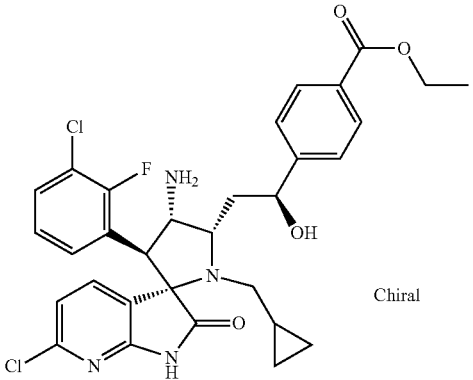 [SMILES: CCOC(=O)c1ccc([C@@H](O)C[C@H]2[C@@H](N)[C@H](c3cccc(Cl)c3F)[C@]3(C(=O)Nc4nc(Cl)ccc43)N2CC2CC2)cc1] Chiral | | | |
| A-9q | 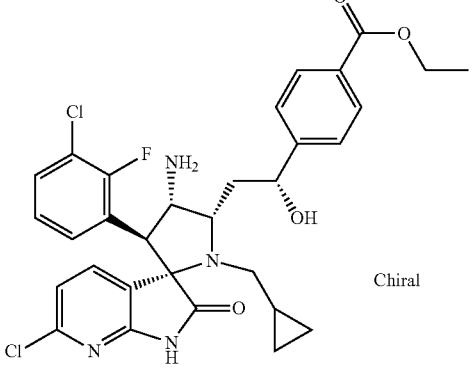 Chiral | | | |
| A-9r | 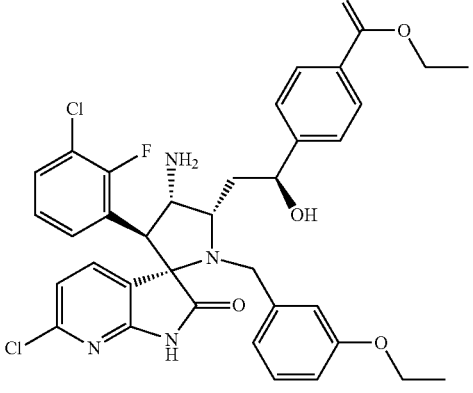 | | | |

TABLE 9-continued

| # | structure | $t_{ret}$ [min] | $[M + H]^+$ | HPLC method |
|---|---|---|---|---|
| A-9s | 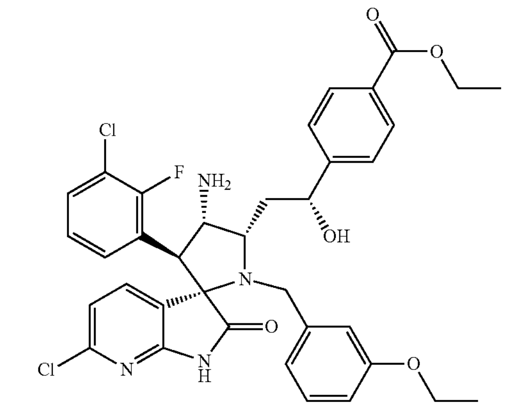 | | | |
| A-9t | 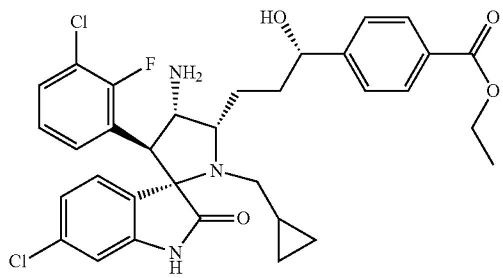 [SMILES: CCOC(=O)c1ccc([C@@H](O)CC[C@H]2[C@@H](N)[C@H](c3cccc(Cl)c3F)[C@]3(C(=O)Nc4cc(Cl)ccc43)N2CC2CC2)cc1] | 1.46 | 626 | A |
| A-9u | 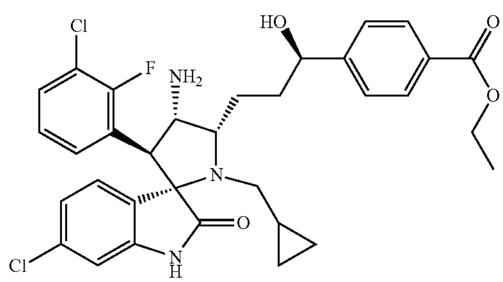 | 1.46 | 626 | A |

Synthesis of Compounds (I) According to the Invention (Method G)

Experimental Procedure for the Synthesis of Compound I-1

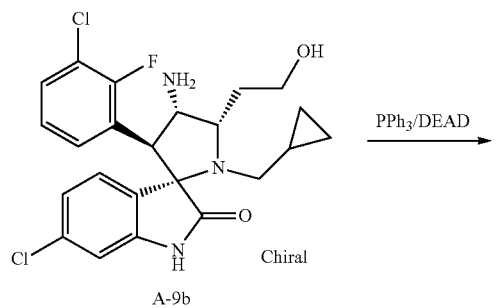

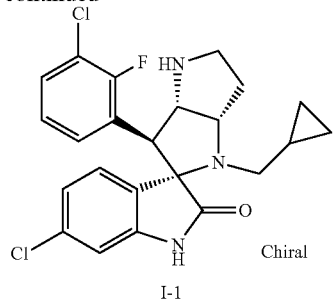

To a solution of A-9a (89 mg, 0.19 mmol) in DCM is added triphenylphosphine (60 mg, 0.23 mmol) and DEAD (100 mg, 0.23 mmol, 40% in toluene) and the reaction mixture is stirred for 1 h at rt. Some drops of saturated aqueous NaHCO₃ solution are added to the reaction mixture before it is concentrated in vacuo and purified by preparative HPLC.

The following compounds (I) (table 10) are available in an analogous manner starting from different intermediates A-9.
TABLE 10
| # | structure | $t_{ret}$ [min] | $[M + H]^+$ | HPLC method |
|---|---|---|---|---|
| I-1 | 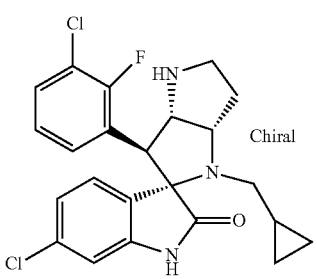 [SMILES: O=C1Nc2cc(Cl)ccc2[C@@]12[C@@H](c1cccc(Cl)c1F)[C@@H]1NCC[C@@H]1N2CC1CC1] | 1.37 | 464 | A |
| I-2 | 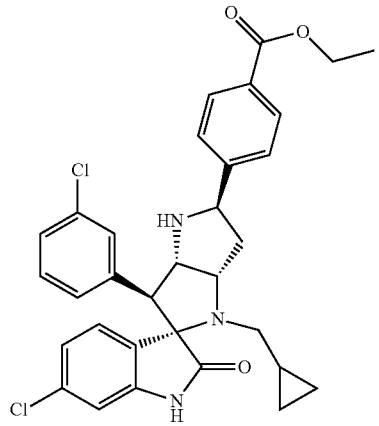 [SMILES: CCOC(=O)c1ccc([C@H]2C[C@H]3[C@@H](N2)[C@H](c2cccc(Cl)c2)[C@]2(C(=O)Nc4cc(Cl)ccc42)N3CC2CC2)cc1] | 0.97 | 576 | B |
| I-3 | 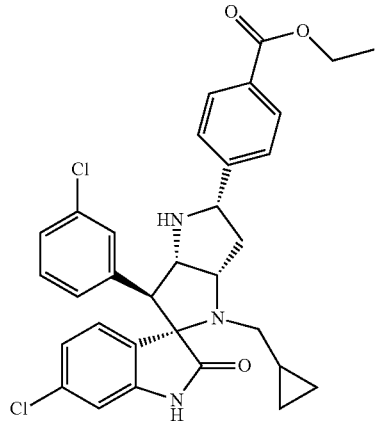 [SMILES: CCOC(=O)c1ccc([C@@H]2C[C@H]3[C@@H](N2)[C@H](c2cccc(Cl)c2)[C@]2(C(=O)Nc4cc(Cl)ccc42)N3CC2CC2)cc1] | 0.99 | 576 | B |

TABLE 10-continued

| # | structure | $t_{ret}$ [min] | $[M + H]^+$ | HPLC method |
|---|---|---|---|---|
| I-4 | 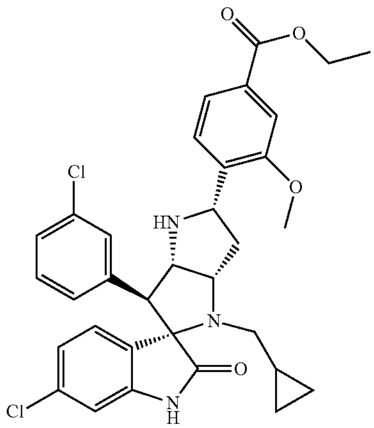 [SMILES: CCOC(=O)c1ccc([C@@H]2C[C@H]3[C@@H](N2)[C@H](c2cccc(Cl)c2)[C@]2(C(=O)Nc4cc(Cl)ccc42)N3CC2CC2)c(OC)c1] | 1.01 | 606 | B |
| I-5 | 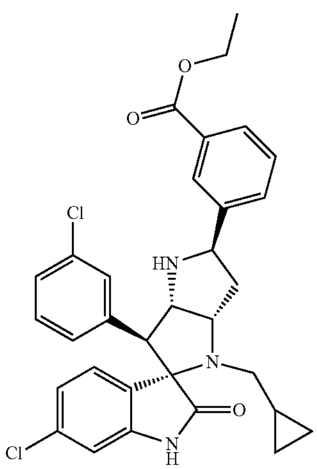 [SMILES: CCOC(=O)c1cccc([C@H]2C[C@H]3[C@@H](N2)[C@H](c2cccc(Cl)c2)[C@]2(C(=O)Nc4cc(Cl)ccc42)N3CC2CC2)c1] | 0.97 | 576 | B |
| I-6 | 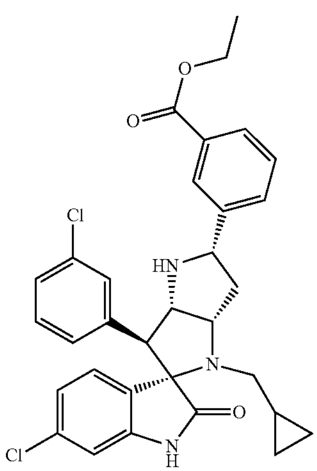 [SMILES: CCOC(=O)c1cccc([C@@H]2C[C@H]3[C@@H](N2)[C@H](c2cccc(Cl)c2)[C@]2(C(=O)Nc4cc(Cl)ccc42)N3CC2CC2)c1] | 1.00 | 576 | B |

TABLE 10-continued

| # | structure | $t_{ret}$ [min] | $[M + H]^+$ | HPLC method |
|---|---|---|---|---|
| I-7 | 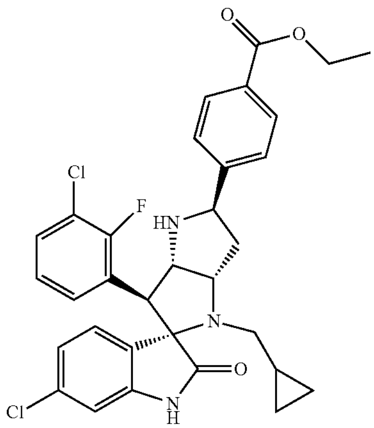 [SMILES: CCOC(=O)c1ccc([C@H]2C[C@H]3[C@@H](N2)[C@H](c2cccc(Cl)c2F)[C@]2(C(=O)Nc4cc(Cl)ccc42)N3CC2CC2)cc1] | 0.68 | 594 | G |
| I-8 | 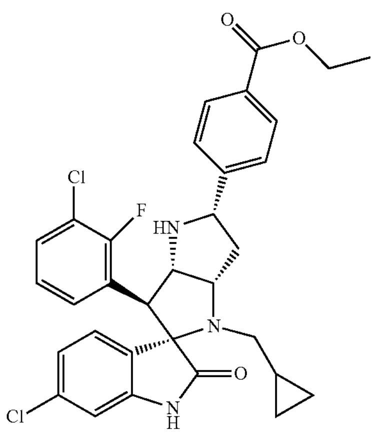 [SMILES: CCOC(=O)c1ccc([C@@H]2C[C@H]3[C@@H](N2)[C@H](c2cccc(Cl)c2F)[C@]2(C(=O)Nc4cc(Cl)ccc42)N3CC2CC2)cc1] | 0.66 | 594 | G |
| I-9 | 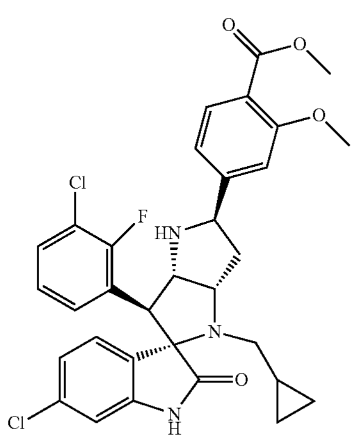 [SMILES: COC(=O)c1ccc([C@H]2C[C@H]3[C@@H](N2)[C@H](c2cccc(Cl)c2F)[C@]2(C(=O)Nc4cc(Cl)ccc42)N3CC2CC2)cc1OC] | 0.89 | 610 | B |

TABLE 10-continued
| # | structure | t_ret [min] | [M + H]+ | HPLC method |
|---|---|---|---|---|
| I-10 | 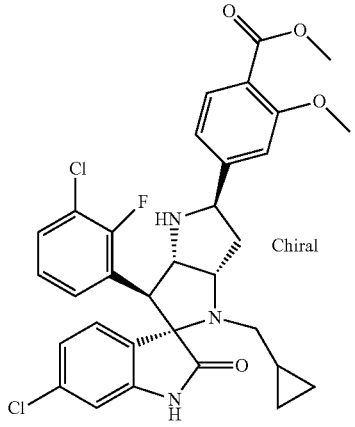 [SMILES: COC(=O)c1ccc([C@H]2C[C@H]3[C@@H](N2)[C@H](c2cccc(Cl)c2F)[C@]2(C(=O)Nc4cc(Cl)ccc42)N3CC2CC2)cc1OC] | 1.54 | 610 | A |
| I-11 | 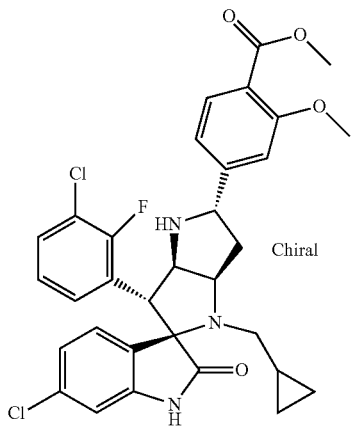 [SMILES: COC(=O)c1ccc([C@@H]2C[C@@H]3[C@H](N2)[C@@H](c2cccc(Cl)c2F)[C@@]2(C(=O)Nc4cc(Cl)ccc42)N3CC2CC2)cc1OC] | 1.54 | 610 | A |
| I-12 | 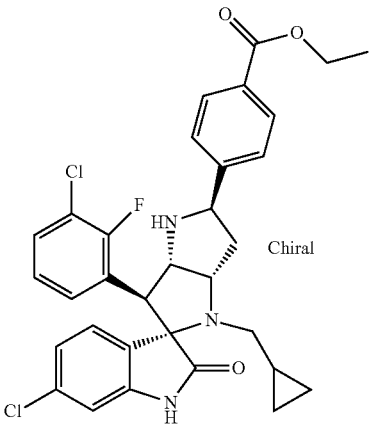 [SMILES: CCOC(=O)c1ccc([C@H]2C[C@H]3[C@@H](N2)[C@H](c2cccc(Cl)c2F)[C@]2(C(=O)Nc4cc(Cl)ccc42)N3CC2CC2)cc1] | 1.69 | 592 | A |

TABLE 10-continued

| # | structure | t$_{ret}$ [min] | [M + H]$^+$ | HPLC method |
|---|---|---|---|---|
| I-13 | 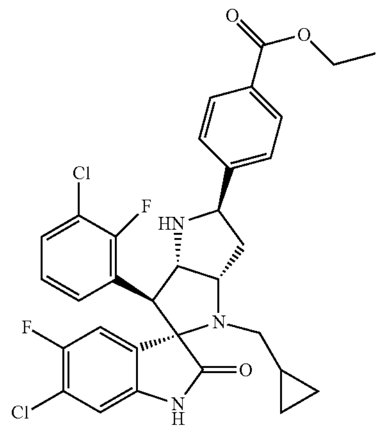 [SMILES: CCOC(=O)c1ccc([C@H]2C[C@H]3[C@@H](N2)[C@H](c2cccc(Cl)c2F)[C@]2(C(=O)Nc4cc(Cl)c(F)cc42)N3CC2CC2)cc1] | 1.65 | 612 | A |
| I-14 | 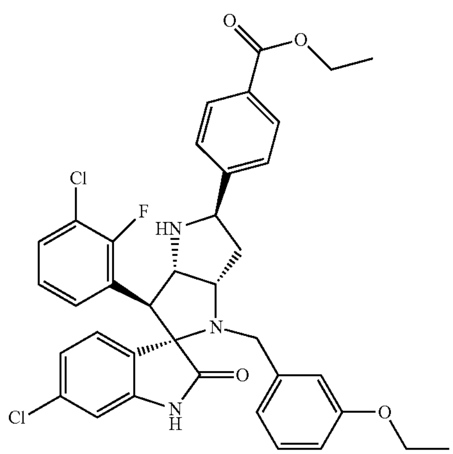 [SMILES: CCOC(=O)c1ccc([C@H]2C[C@H]3[C@@H](N2)[C@H](c2cccc(Cl)c2F)[C@]2(C(=O)Nc4cc(Cl)ccc42)N3Cc2cccc(OCC)c2)cc1] | 1.00 | 674 | B |
| I-15 | 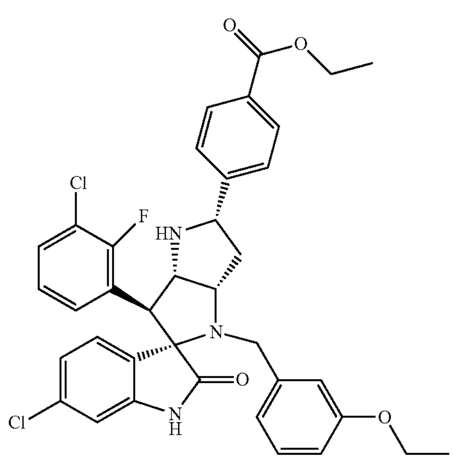 [SMILES: CCOC(=O)c1ccc([C@@H]2C[C@H]3[C@@H](N2)[C@H](c2cccc(Cl)c2F)[C@]2(C(=O)Nc4cc(Cl)ccc42)N3Cc2cccc(OCC)c2)cc1] | 1.02 | 674 | B |

TABLE 10-continued
| # | structure | $t_{ret}$ [min] | $[M + H]^+$ | HPLC method |
|---|---|---|---|---|
| I-16 | 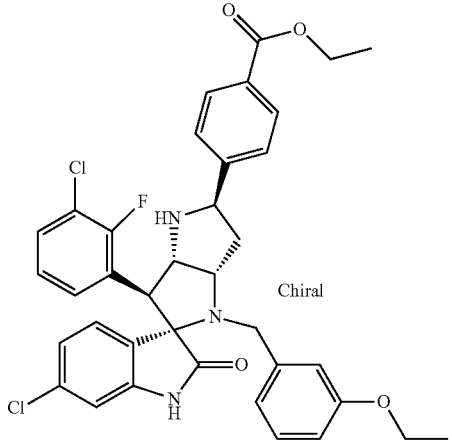 [SMILES: CCOC(=O)c1ccc([C@H]2C[C@H]3[C@@H](N2)[C@H](c2cccc(Cl)c2F)[C@]2(C(=O)Nc4cc(Cl)ccc42)N3Cc2cccc(OCC)c2)cc1] | 1.01 | 674 | B |
| I-17 | 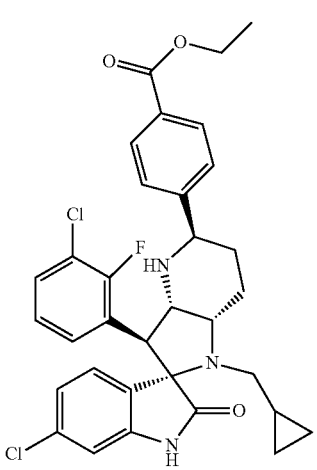 [SMILES: CCOC(=O)c1ccc([C@H]2CC[C@H]3[C@@H](N2)[C@H](c2cccc(Cl)c2F)[C@]2(C(=O)Nc4cc(Cl)ccc42)N3CC2CC2)cc1] | 1.76 | 608 | A |
| I-18 | 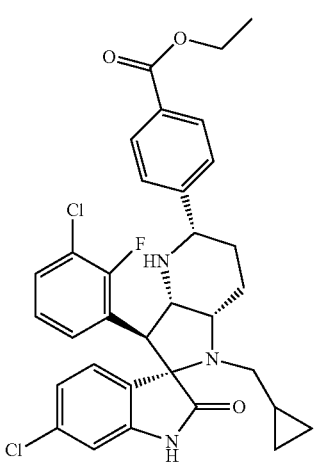 [SMILES: CCOC(=O)c1ccc([C@@H]2CC[C@H]3[C@@H](N2)[C@H](c2cccc(Cl)c2F)[C@]2(C(=O)Nc4cc(Cl)ccc42)N3CC2CC2)cc1] | 1.72 | 608 | A |

TABLE 10-continued
| # | structure | $t_{ret}$ [min] | $[M + H]^+$ | HPLC method |
|---|---|---|---|---|
| I-19 | 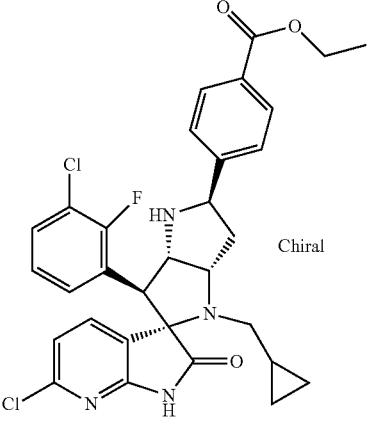 [SMILES: CCOC(=O)c1ccc([C@H]2C[C@H]3[C@@H](N2)[C@H](c2cccc(Cl)c2F)[C@]2(C(=O)Nc4nc(Cl)ccc42)N3CC2CC2)cc1] | | | |
| I-20 | 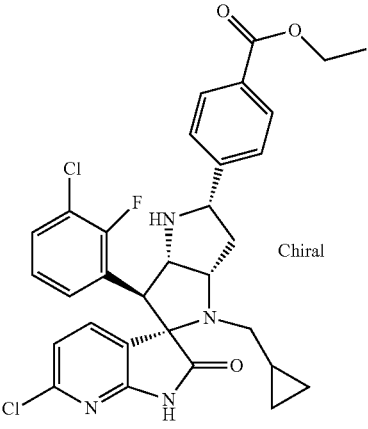 [SMILES: CCOC(=O)c1ccc([C@@H]2C[C@H]3[C@@H](N2)[C@H](c2cccc(Cl)c2F)[C@]2(C(=O)Nc4nc(Cl)ccc42)N3CC2CC2)cc1] | | | |
| I-21 | 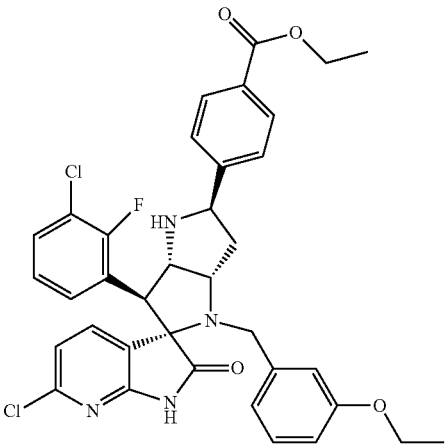 [SMILES: CCOC(=O)c1ccc([C@H]2C[C@H]3[C@@H](N2)[C@H](c2cccc(Cl)c2F)[C@]2(C(=O)Nc4nc(Cl)ccc42)N3Cc2cccc(OCC)c2)cc1] | | | |

TABLE 10-continued

| # | structure | $t_{ret}$ [min] | $[M + H]^+$ | HPLC method |
|---|---|---|---|---|
| I-22 | 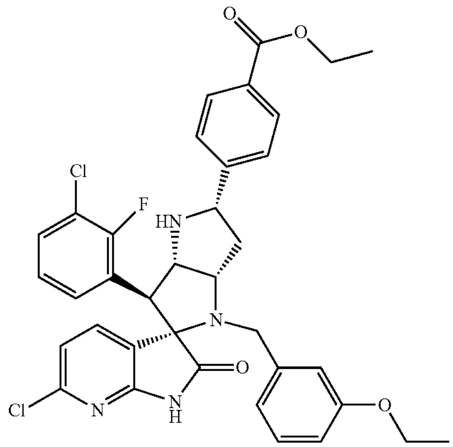 [SMILES: CCOC(=O)c1ccc([C@@H]2C[C@H]3[C@@H](N2)[C@H](c2cccc(Cl)c2F)[C@]2(C(=O)Nc4nc(Cl)ccc42)N3Cc2cccc(OCC)c2)cc1] | | | |
| I-23 | 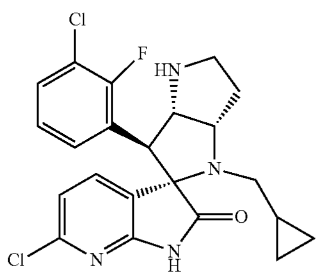 [SMILES: O=C1Nc2nc(Cl)ccc2[C@@]12[C@@H](c1cccc(Cl)c1F)[C@@H]1NCC[C@@H]1N2CC1CC1] | 1.28 | 447 | A |

Synthesis of Further Compounds (I) by Ester Saponification of Initially Obtained Compounds (I)

Experimental Procedure for the Synthesis of I-24

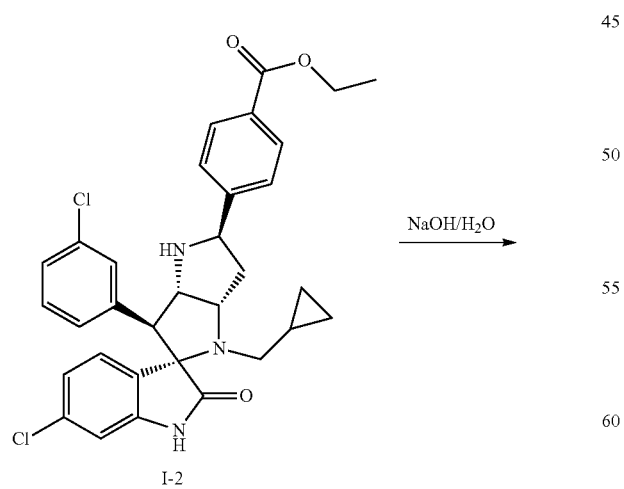

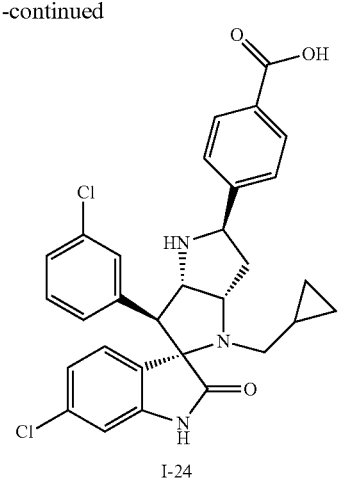

To a solution of compound I-2 (11 mg, 0.015 mmol) in THF is added NaOH (38 µL, 8 M in H₂O) and the reaction mixture is stirred at 60° C. over night. The reaction mixture is concentrated in vacuo and purified by preparative HPLC.

The following compounds (I) (Table 11) are available in an analogous manner starting from initially obtained compounds (I).

TABLE 11
| * | structure | $t_{ret}$ [min] | $[M + H]^+$ | HPLC method |
|---|---|---|---|---|
| I-24 | 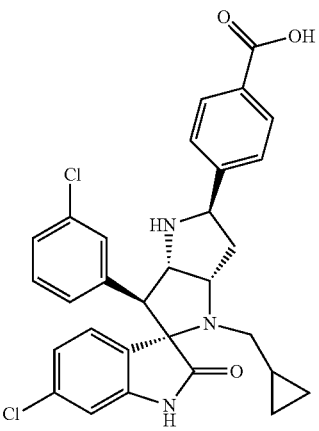 [SMILES: O=C(O)c1ccc([C@H]2C[C@H]3[C@@H](N2)[C@H](c2cccc(Cl)c2)[C@]2(C(=O)Nc4cc(Cl)ccc42)N3CC2CC2)cc1] | 1.06 | 548 | A |
| I-25 | 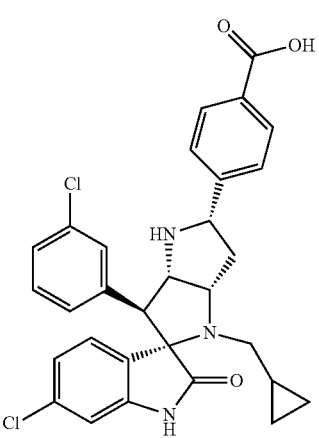 [SMILES: O=C(O)c1ccc([C@@H]2C[C@H]3[C@@H](N2)[C@H](c2cccc(Cl)c2)[C@]2(C(=O)Nc4cc(Cl)ccc42)N3CC2CC2)cc1] | 1.04 | 548 | A |
| I-26 | 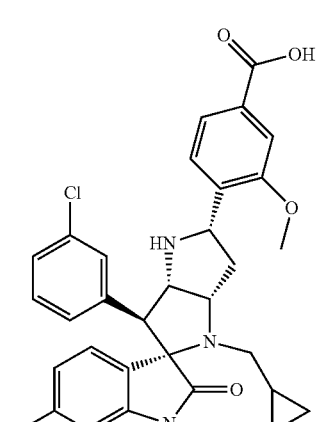 | 1.05 | 578 | A |

TABLE 11-continued

| * | structure | $t_{ret}$ [min] | $[M + H]^+$ | HPLC method |
|---|---|---|---|---|
| I-27 | 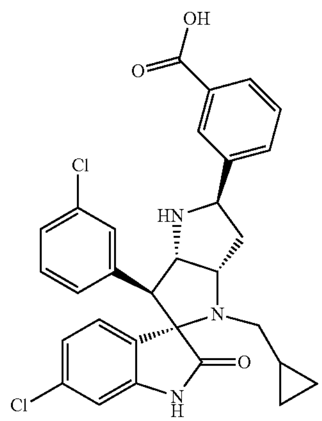 [SMILES: O=C(O)c1cccc([C@H]2C[C@H]3[C@@H](N2)[C@H](c2cccc(Cl)c2)[C@]2(C(=O)Nc4cc(Cl)ccc42)N3CC2CC2)c1] | 1.08 | 548 | A |
| I-28 | 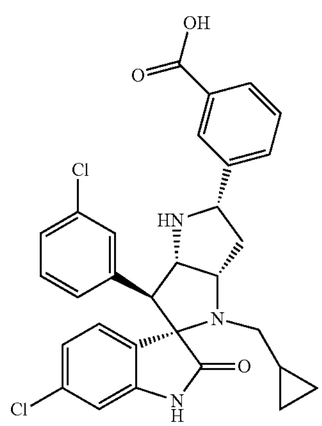 [SMILES: O=C(O)c1cccc([C@@H]2C[C@H]3[C@@H](N2)[C@H](c2cccc(Cl)c2)[C@]2(C(=O)Nc4cc(Cl)ccc42)N3CC2CC2)c1] | 1.06 | 548 | A |
| I-29 | 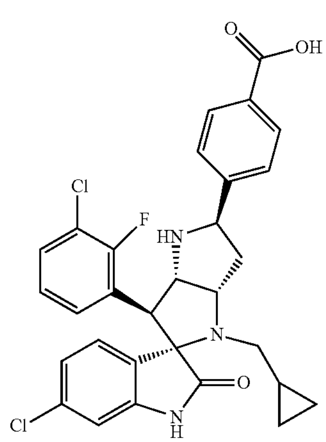 [SMILES: O=C(O)c1ccc([C@H]2C[C@H]3[C@@H](N2)[C@H](c2cccc(Cl)c2F)[C@]2(C(=O)Nc4cc(Cl)ccc42)N3CC2CC2)cc1] | 1.06 | 566 | A |

TABLE 11-continued

| * | structure | $t_{ret}$ [min] | $[M + H]^+$ | HPLC method |
|---|---|---|---|---|
| I-30 | 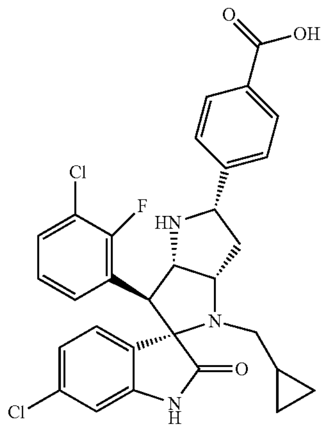 [SMILES: O=C(O)c1ccc([C@@H]2C[C@H]3[C@@H](N2)[C@H](c2cccc(Cl)c2F)[C@]2(C(=O)Nc4cc(Cl)ccc42)N3CC2CC2)cc1] | 1.03 | 566 | A |
| I-31 | 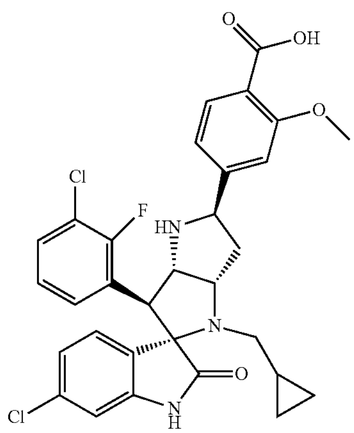 [SMILES: COc1cc([C@H]2C[C@H]3[C@@H](N2)[C@H](c2cccc(Cl)c2F)[C@]2(C(=O)Nc4cc(Cl)ccc42)N3CC2CC2)ccc1C(=O)O] | 1.05 | 596 | A |
| I-32 | 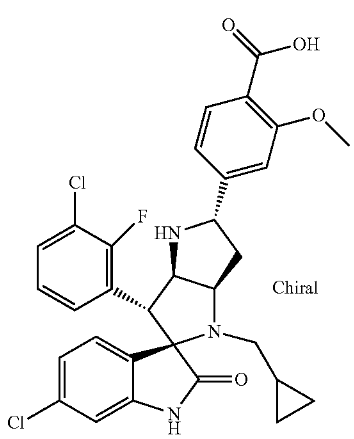 [SMILES: COc1cc([C@@H]2C[C@@H]3[C@H](N2)[C@@H](c2cccc(Cl)c2F)[C@@]2(C(=O)Nc4cc(Cl)ccc42)N3CC2CC2)ccc1C(=O)O] | 1.08 | 596 | A |

TABLE 11-continued
| * | structure | t_ret [min] | [M + H]+ | HPLC method |
|---|---|---|---|---|
| I-33 | 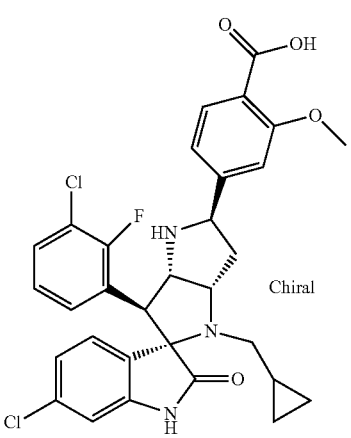 [SMILES: COc1cc([C@H]2C[C@H]3[C@@H](N2)[C@H](c2cccc(Cl)c2F)[C@]2(C(=O)Nc4cc(Cl)ccc42)N3CC2CC2)ccc1C(=O)O] Chiral | 1.08 | 596 | A |
| I-34 | 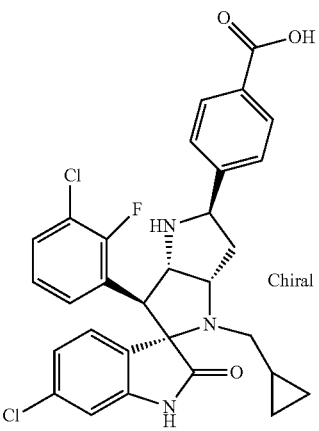 [SMILES: O=C(O)c1ccc([C@H]2C[C@H]3[C@@H](N2)[C@H](c2cccc(Cl)c2F)[C@]2(C(=O)Nc4cc(Cl)ccc42)N3CC2CC2)cc1] Chiral | 1.20 | 566 | A |
| I-35 | 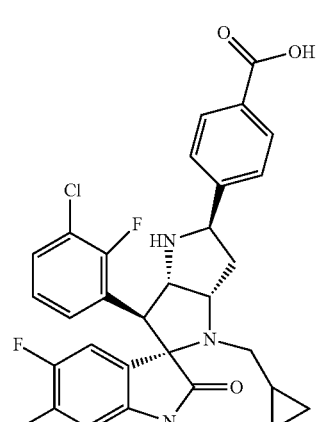 | 1.08 | 584 | A |

TABLE 11-continued

| * | structure | $t_{ret}$ [min] | $[M + H]^+$ | HPLC method |
|---|---|---|---|---|
| I-36 | 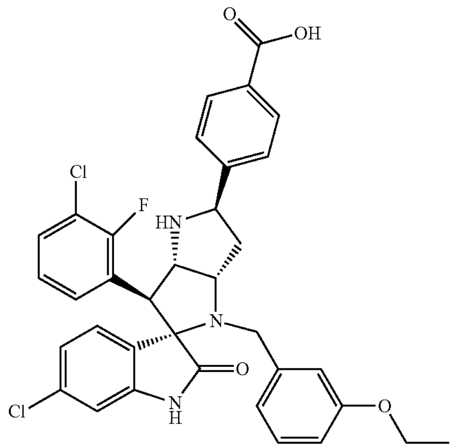 [SMILES: CCOc1cccc(CN2[C@H]3C[C@H](c4ccc(C(=O)O)cc4)N[C@H]3[C@H](c3cccc(Cl)c3F)[C@]23C(=O)Nc2cc(Cl)ccc23)c1] | 1.13 | 646 | A |
| I-37 | 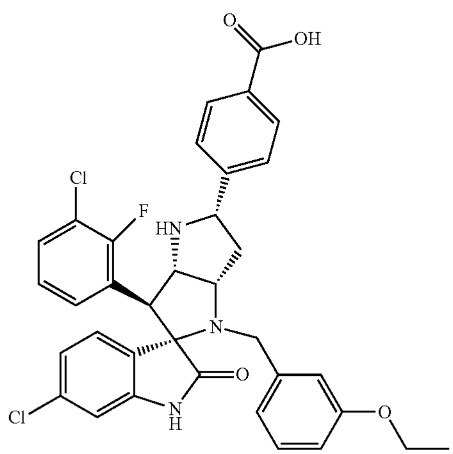 [SMILES: CCOc1cccc(CN2[C@H]3C[C@@H](c4ccc(C(=O)O)cc4)N[C@H]3[C@H](c3cccc(Cl)c3F)[C@]23C(=O)Nc2cc(Cl)ccc23)c1] | 1.12 | 646 | A |
| I-38 | 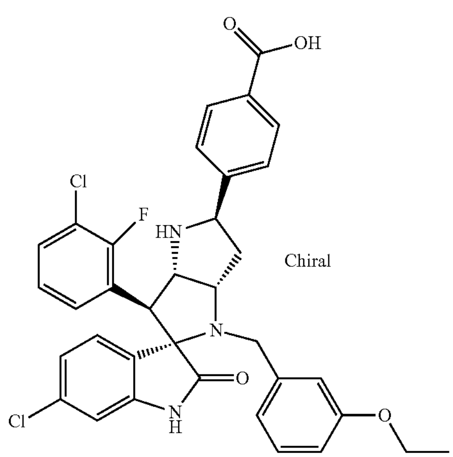 [SMILES: CCOc1cccc(CN2[C@H]3C[C@H](c4ccc(C(=O)O)cc4)N[C@H]3[C@H](c3cccc(Cl)c3F)[C@]23C(=O)Nc2cc(Cl)ccc23)c1] | 1.07 | 646 | A |

TABLE 11-continued

| * | structure | $t_{ret}$ [min] | $[M+H]^+$ | HPLC method |
|---|---|---|---|---|
| I-39 | 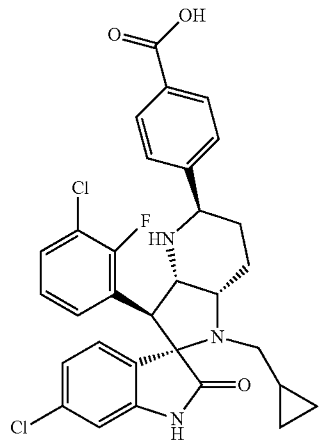 [SMILES: O=C(O)c1ccc([C@H]2CC[C@H]3[C@@H](N2)[C@H](c2cccc(Cl)c2F)[C@]2(C(=O)Nc4cc(Cl)ccc42)N3CC2CC2)cc1] | 1.09 | 580 | A |
| I-40 | 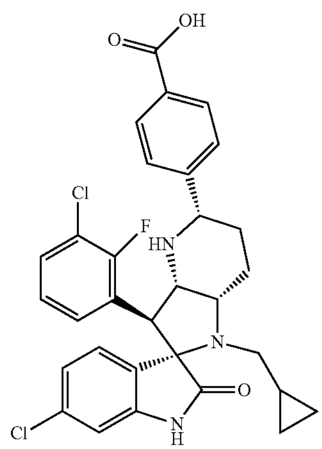 [SMILES: O=C(O)c1ccc([C@@H]2CC[C@H]3[C@@H](N2)[C@H](c2cccc(Cl)c2F)[C@]2(C(=O)Nc4cc(Cl)ccc42)N3CC2CC2)cc1] | 1.14 | 580 | A |
| I-41 | 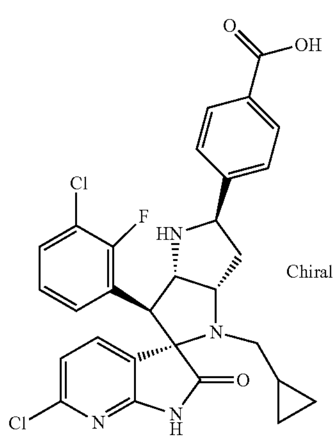 [SMILES: O=C(O)c1ccc([C@H]2C[C@H]3[C@@H](N2)[C@H](c2cccc(Cl)c2F)[C@]2(C(=O)Nc4nc(Cl)ccc42)N3CC2CC2)cc1] | | | |

TABLE 11-continued
| * | structure | $t_{ret}$ [min] | $[M + H]^+$ | HPLC method |
|---|---|---|---|---|
| I-42 | 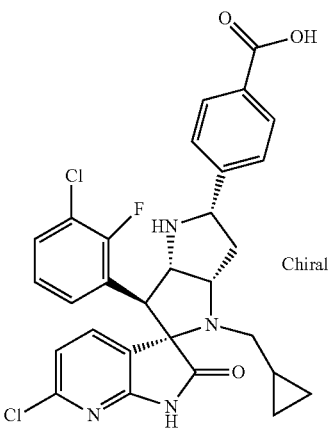 [SMILES: O=C(O)c1ccc([C@@H]2C[C@H]3[C@@H](N2)[C@H](c2cccc(Cl)c2F)[C@]2(C(=O)Nc4nc(Cl)ccc42)N3CC2CC2)cc1] | | | |
| I-43 | 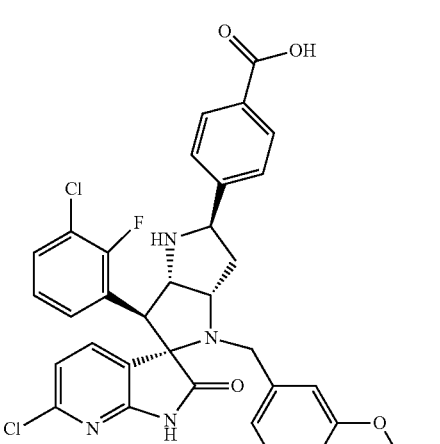 | | | |
| I-44 | 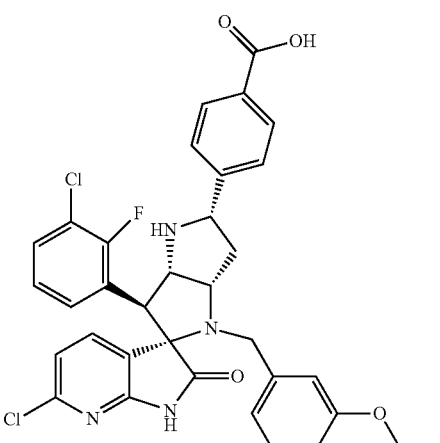 | | | |

Synthesis of Intermediate A-12 (Method K)
Experimental Procedure for the Preparation of Intermediate A-12a.

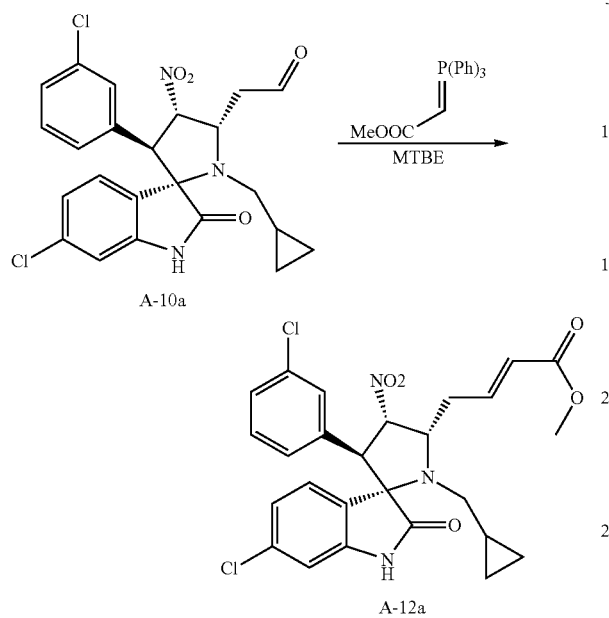

A-10a

A-12a

To a solution of compound A-10a (98 mg, 0.21 eq) in MTBE is added methyl (triphenylphosphoranylidene)acetate (103 mg, 0.31 mmol) and the reaction mixture is stirred at rt for 30 min. The reaction mixture is concentrated in vacuo and purified by prep. HPLC to give product A-12a (Table 12).

TABLE 12

| # | structure | $t_{ret}$ [min] | $[M + H]^+$ | HPLC method |
|---|---|---|---|---|
| A-12a | 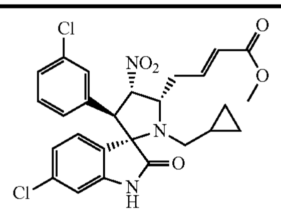 | 1.53 | 530 | A |

Synthesis of Compounds (I) According to the Invention (Method L)
Experimental Procedure for the Synthesis of I-45

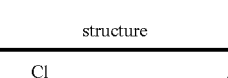

A-12a

I-45

-continued

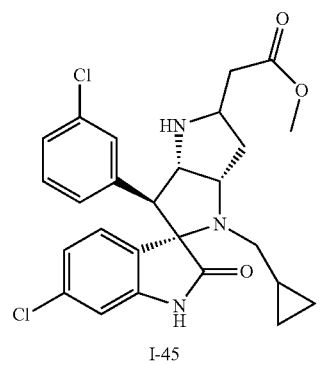

I-45

To a solution of A-12a (80 mg, 0.15 mmol) in a mixture of water and THF is added indium powder (138 mg, 1.2 mmol) and conc. HCl (225 µL, 2.7 mmol) portionwise and the reaction mixture is stirred over night. To the reaction mixture is added NaOH (2 M in H₂O) and the solids are filtered off. The mixture is extracted with EtOAc and the combined organic layer is dried (MgSO₄), filtered, concentrated in vacuo and the crude product is purified by HPLC to obtain I-45 as a racemic mixture of two diastereomers (table 13).

TABLE 13

| # | structure | $t_{ret}$ [min] | $[M + H]^+$ | HPLC method |
|---|---|---|---|---|
| I-45 | 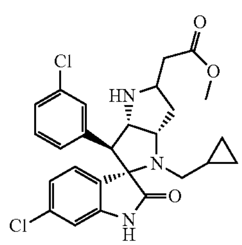 | 1.39 | 500 | A |

Synthesis of Further Compounds (I) by Ester Saponification of Initially Obtained Compounds (I)
Experimental Procedure for the Synthesis of Compounds I-46 and I-47

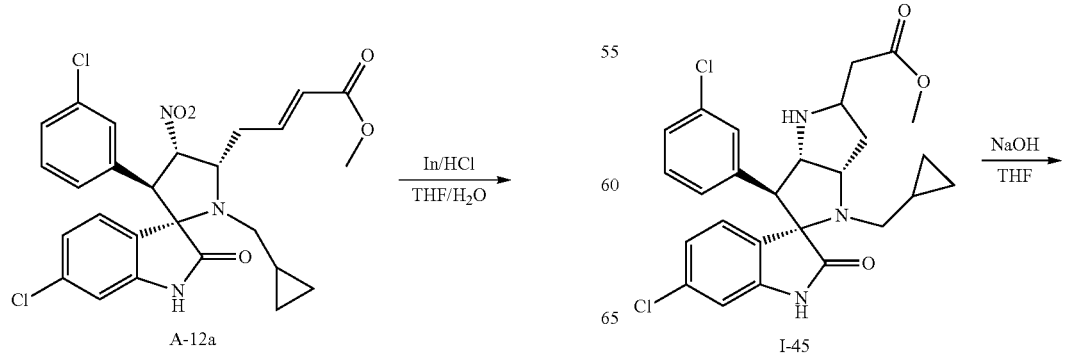

Synthesis of Intermediates A-13 (Method M)

Experimental Procedure for the Synthesis of Intermediate A-13a

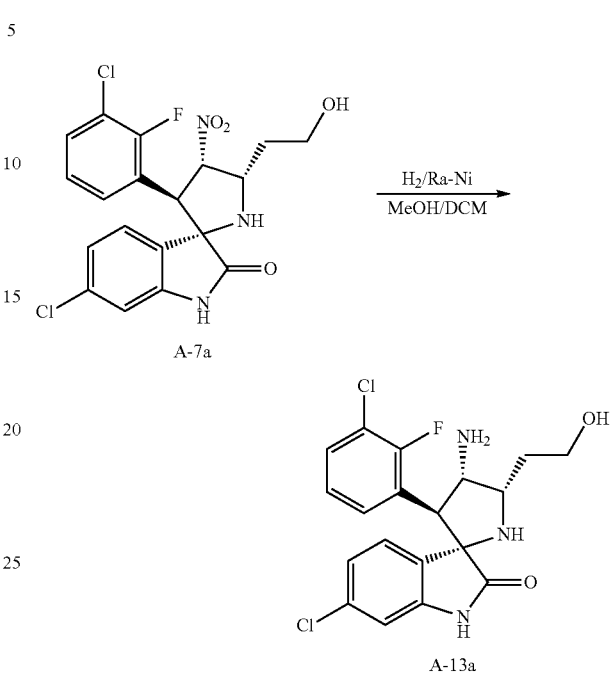

To a solution of compound I-45 (76 mg, 0.01 mmol) in THF is added NaOH (247 μL, 8 M in H$_2$O) and the reaction mixture is stirred at 60° C. for 2 h. The reaction mixture is concentrated in vacuo and purified by prep. HPLC to give products I-46 and I-47 (table 14).

To a solution of A-7a (500 mg, 1.18 mmol) in a mixture of MeOH and DCM in a *BUCHI* autoclave is added Raney nickel (125 mg, 2.13 mmol) and the reaction mixture is stirred at a H$_2$ pressure of 8 bar over night. The reaction mixture is filtered and concentrated in vacuo. The obtained crude product is used without further purification.

The following intermediates A-13 (table 15) are available in an analogous manner starting from different intermediates A-7.

TABLE 14

| # | structure | t$_{ret}$ [min] | [M + H]$^+$ | HPLC method |
|---|---|---|---|---|
| I-46 | 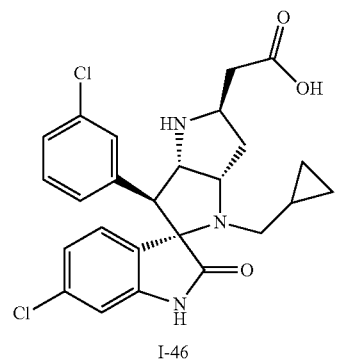 | 0.96 | 486 | A |
| I-47 | 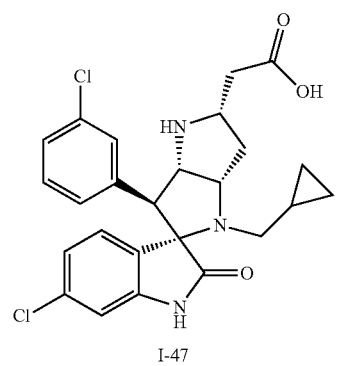 | 0.98 | 486 | A |

TABLE 15

| # | structure | t$_{ret}$ [min] | [M + H]$^+$ | HPLC method |
|---|---|---|---|---|
| A-13a | 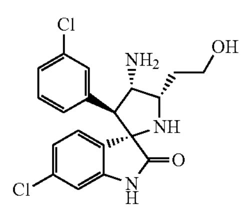 [SMILES: N[C@@H]1[C@H](CCO)N[C@@]2(C(=O)Nc3cc(Cl)ccc32)[C@H]1c1cccc(Cl)c1] | 0.71 | 392 | I |
| A-13b | 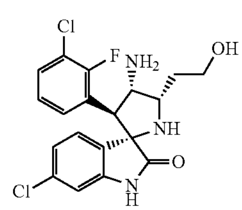 [SMILES: N[C@@H]1[C@H](CCO)N[C@@]2(C(=O)Nc3cc(Cl)ccc32)[C@H]1c1cccc(Cl)c1F] | 0.41 | 410 | C |

TABLE 15-continued

| # | structure | t_ret [min] | [M + H]+ | HPLC method |
|---|---|---|---|---|
| A-13c | 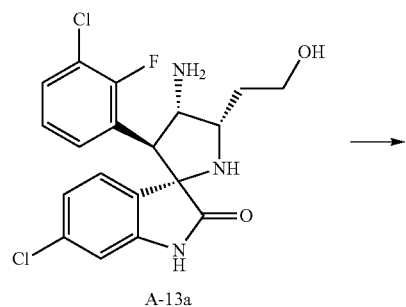 | 0.88 | 411 | A |

Synthesis of Intermediates A-14 (Method N)

Experimental Procedure for the Synthesis of Intermediate A-14a

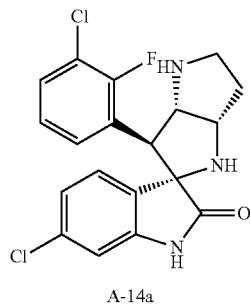

A-13a

↓

A-14a

The following intermediates A-14 (table 16) are available in an analogous manner as described for conversion of compound A-9b to I-1 (method G) starting from different intermediates A-13.

TABLE 16

| # | structure | t_ret [min] | [M + H]+ | HPLC method |
|---|---|---|---|---|
| A-14a | 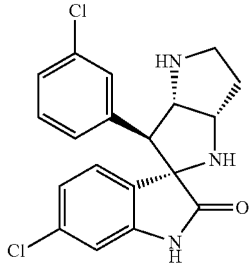 [SMILES: O=C1Nc2cc(Cl)ccc2[C@]12N[C@H]1CCN[C@H]1[C@@H]2c1cccc(Cl)c1] | 1.04 | 374 | A |
| A-14b | 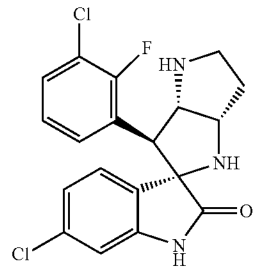 [SMILES: O=C1Nc2cc(Cl)ccc2[C@]12N[C@H]1CCN[C@H]1[C@@H]2c1cccc(Cl)c1F] | 1.07 | 392 | A |
| A-14c | Chiral | 1.05 | 392 | A |
| A-14d | 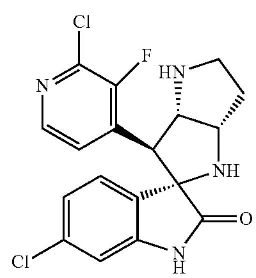 [SMILES: O=C1Nc2cc(Cl)ccc2[C@]12N[C@H]1CCN[C@H]1[C@@H]2c1ccnc(Cl)c1F] | 0.96 | 393 | A |

Synthesis of Intermediates A-15 by Amination/Alkylation (Method O)

Experimental Procedure for the Synthesis of Intermediate A-15a

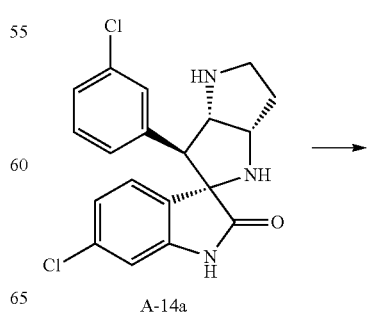

A-14a

→

-continued

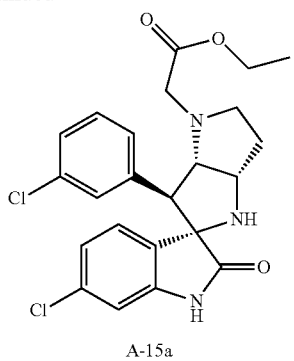

A-15a

To a solution of glyoxylic acid ethyl ester (0.61 mg, 0.30 mmol, 50% in toluene) in acetonitrile is added intermediate A-14a (160 mg, 0.30 mmol) and acetic acid (150 μL) and the reaction mixture is stirred for 15 min. Sodium triacetoxyborohydride (127 mg, 0.603 mmol) is added and the reaction mixture is stirred overnight. To the reaction mixture is added water and it is extracted with DCM. The combined organic layer is dried (MgSO$_4$), filtered, concentrated in vacuo and the crude product is used without further purification.

The following intermediates A-15 (table 17) are available in an analogous manner starting from different intermediates A-14.

TABLE 17

| # | structure | t$_{ret}$ [min] | [M + H] | HPLC method |
|---|---|---|---|---|
| A-15a | 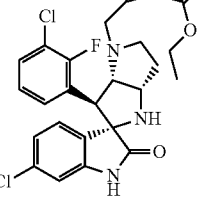 | 1.24 | 460 | A |
| A-15b | 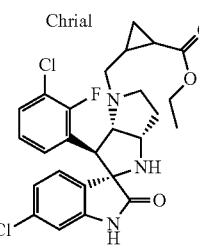 | 0.57 | 478 | C |
| A-15c | Chiral 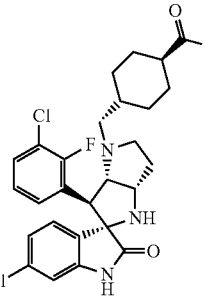 | 0.69 | 478 | B |

TABLE 17-continued

| # | structure | t$_{ret}$ [min] | [M + H] | HPLC method |
|---|---|---|---|---|
| A-15d | 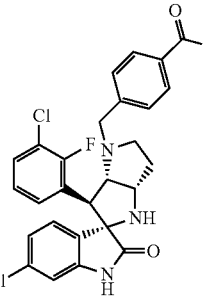 | 0.75 | 518 | B |
| A-15e | Chrial 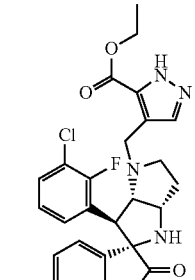 | 0.74 | 518 | D |
| A-15f | 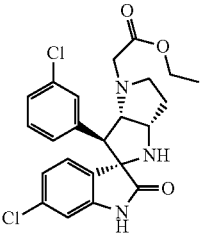 [SMILES: CCOC(=O)CN1CC[C@@H]2N[C@@]3(C(=O)Nc4cc(Cl)ccc43)[C@@H](c3cccc(Cl)c3)[C@@H]21] | 0.84 | 546 | D |
| A-15g | 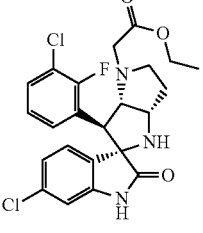 | 0.63 | 540 | C |
| A-15h | 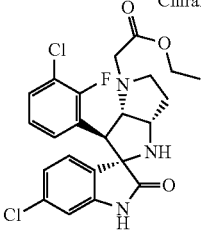 [SMILES: CCOC(=O)CN1CC[C@@H]2N[C@@]3(C(=O)Nc4cc(Cl)ccc43)[C@@H](c3cccc(Cl)c3F)[C@@H]21] | 1.30 | 544 | A |

125

Synthesis of Compounds (1) According to the Invention (Method P)

Experimental Procedure for the Synthesis of Compound I-48

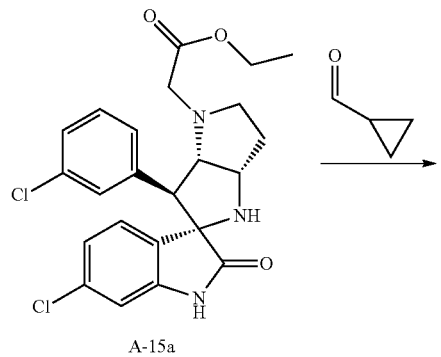

A-15a

I-48

To a solution of cyclopropanecarbaldehyde (61 mg, 0.87 mmol) in acetonitrile is added intermediate A-15a (100 mg, 0.22 mmol) and AcOH (100 µL) and the reaction mixture is stirred for 15 min. Sodium triacetoxyborohydride (92 mg, 0.44 mmol) is added and the reaction mixture is stirred for 1 h. To the reaction mixture is added saturated $NaHCO_3$ solution and it is extracted with DCM. The combined organic layer is dried ($MgSO_4$), filtered, concentrated in vacuo and the crude product is purified by chromatography if necessary.

The following compounds (I) (table 18) are available in an analogous manner starting from different intermediates A-15.

TABLE 18

| # | Structure | $t_{ret}$ [min] | $[M + H]^+$ | HPLC method |
|---|---|---|---|---|
| I-48 | 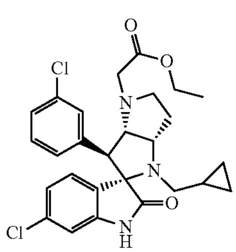 [SMILES: CCOC(=O)CN1CC[C@H]2[C@@H]1[C@H](c1cccc(Cl)c1)[C@]1(C(=O)Nc3cc(Cl)ccc31)N2CC1CC1] | 1.53 | 514 | A |

TABLE 18-continued

| # | Structure | $t_{ret}$ [min] | $[M + H]^+$ | HPLC method |
|---|---|---|---|---|
| I-49 | 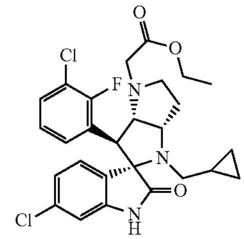 [SMILES: CCOC(=O)CN1CC[C@H]2[C@@H]1[C@H](c1cccc(Cl)c1F)[C@]1(C(=O)Nc3cc(Cl)ccc31)N2CC1CC1] | 0.83 | 532 | C |
| I-50 | 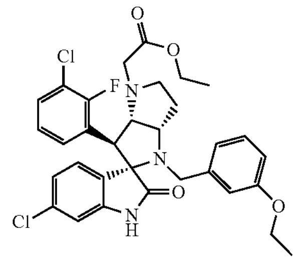 [SMILES: CCOC(=O)CN1CC[C@H]2[C@@H]1[C@H](c1cccc(Cl)c1F)[C@]1(C(=O)Nc3cc(Cl)ccc31)N2Cc1cccc(OCC)c1] | 1.56 | 612 | H |
| I-51 | Chiral | 0.94 | 612 | B |
| I-52 | 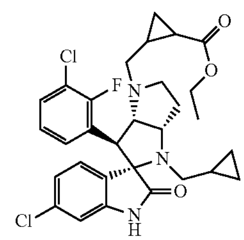 [SMILES: CCOC(=O)C1CC1CN1CC[C@H]2[C@@H]1[C@H](c1cccc(Cl)c1F)[C@]1(C(=O)Nc3cc(Cl)ccc31)N2CC1CC1] | 0.79 | 572 | C |
| I-53 | 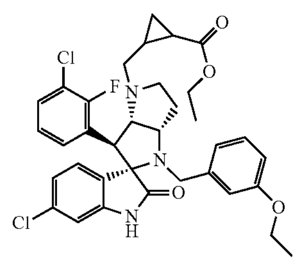 [SMILES: CCOC(=O)C1CC1CN1CC[C@H]2[C@@H]1[C@H](c1cccc(Cl)c1F)[C@]1(C(=O)Nc3cc(Cl)ccc31)N2Cc1cccc(OCC)c1] | 1.00 | 652 | B |
| I-54 | Chrial | 0.68 | 352 | C |

TABLE 18-continued

| # | Structure | $t_{ret}$ [min] | [M + H]⁺ | HPLC method |
|---|---|---|---|---|
| I-55 | 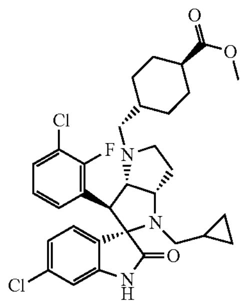 | 1.07 | 600 | D |
| I-56 | 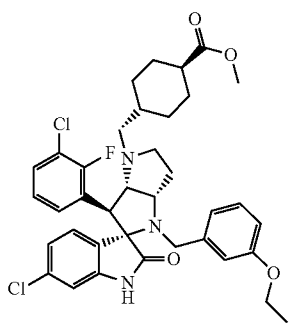 | 1.11 | 680 | D |
| I-57 | 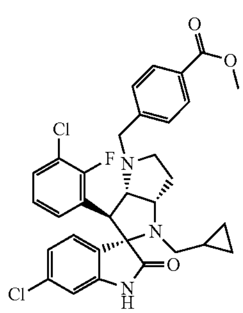 [SMILES: COC(=O)c1ccc(CN2CC[C@H]3[C@@H]2[C@H](c2cccc(Cl)c2F)[C@]2(C(=O)Nc4cc(Cl)ccc42)N3CC2CC2)cc1] | 0.82 | 594 | C |
| I-58 | 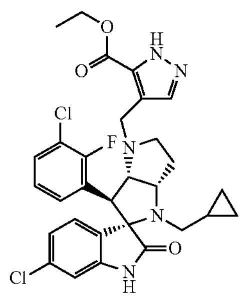 [SMILES: CCOC(=O)c1[nH]ncc1CN1CC[C@H]2[C@@H]1[C@H](c1cccc(Cl)c1F)[C@]1(C(=O)Nc3cc(Cl)ccc31)N2CC1CC1] | 1.59 | 598 | A |
| I-59 | | 1.64 | 678 | A |

Synthesis of Further Compounds (I) by Ester Saponification of Initially Obtained Compounds (I)

Experimental Procedure for the Synthesis of I-60

To a solution of compound I-48 (45 mg, 0.087 mmol) in THF is added NaOH (150 μL, 2 M in H₂O) and the reaction mixture is stirred at 75° C. for 2 h. The reaction mixture is concentrated in vacuo and purified by preparative HPLC.

The following compounds (I) (Table 19) are available in an analogous manner starting from initially obtained compounds (I).

TABLE 19

| # | structure | $t_{ret}$ [min] | [M + H]$^+$ | HPLC method |
|---|---|---|---|---|
| I-60 | 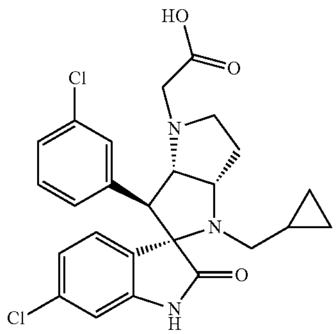 [SMILES: O=C(O)CN1CC[C@H]2[C@@H]1[C@H](c1cccc(Cl)c1)[C@]1(C(=O)Nc3cc(Cl)ccc31)N2CC1CC1] | 1.00 | 486 | A |
| I-61 | 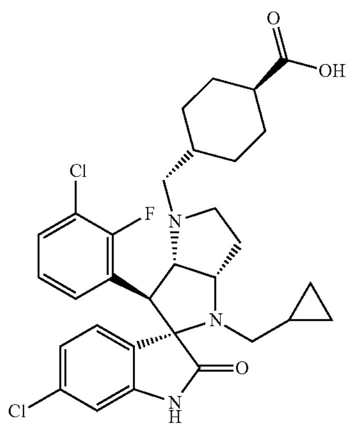 | 1.23 | 586 | A |
| I-62 | 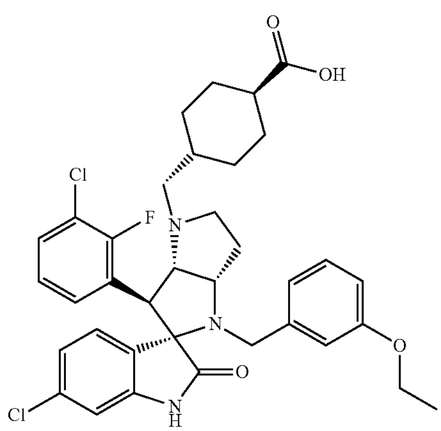 | 1.30 | 666 | A |
| I-63 | 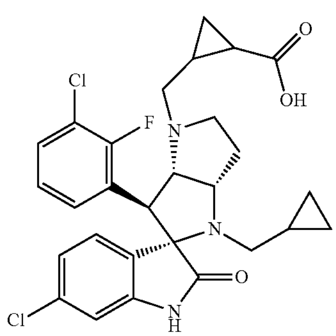 [SMILES: O=C(O)C1CC1CN1CC[C@H]2[C@@H]1[C@H](c1cccc(Cl)c1F)[C@]1(C(=O)Nc3cc(Cl)ccc31)N2CC1CC1] | 1.05 | 544 | A |

TABLE 19-continued

| # | structure | t_ret [min] | [M + H]+ | HPLC method |
|---|---|---|---|---|
| I-64 | 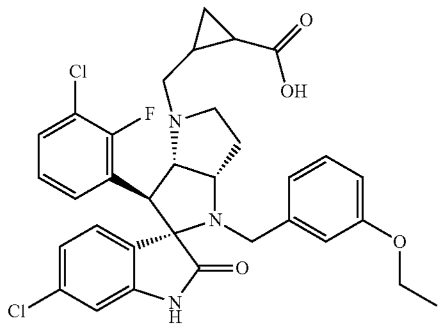 [SMILES: CCOc1cccc(CN2[C@H]3CCN(CC4CC4C(=O)O)[C@H]3[C@H](c3cccc(Cl)c3F)[C@]23C(=O)Nc2cc(Cl)ccc23)c1] | 1.13 | 624 | A |
| I-65 | Chiral | 1.14 | 624 | A |
| I-66 | Chiral | 1.14 | 624 | A |
| I-67 | 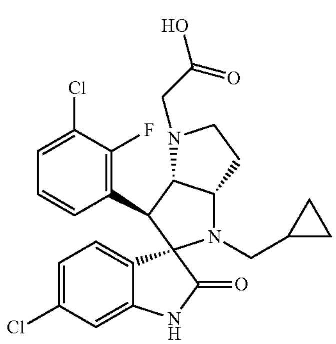 [SMILES: O=C(O)CN1CC[C@H]2[C@@H]1[C@H](c1cccc(Cl)c1F)[C@]1(C(=O)Nc3cc(Cl)ccc31)N2CC1CC1] | 1.02 | 504 | A |

TABLE 19-continued

| # | structure | $t_{ret}$ [min] | [M + H]⁺ | HPLC method |
|---|---|---|---|---|
| I-68 | 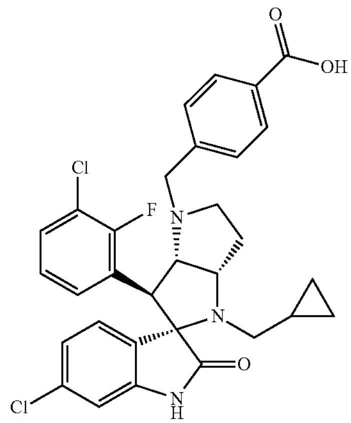 [SMILES: O=C(O)c1ccc(CN2CC[C@H]3[C@@H]2[C@H](c2cccc(Cl)c2F)[C@]2(C(=O)Nc4cc(Cl)ccc42)N3CC2CC2)cc1] | 1.15 | 580 | A |
| I-69 | 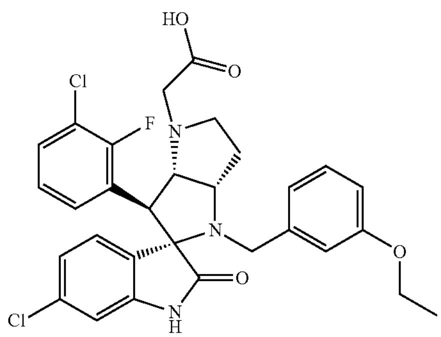 [SMILES: CCOc1cccc(CN2[C@H]3CCN(CC(=O)O)[C@H]3[C@H](c3cccc(Cl)c3F)[C@]23C(=O)Nc2cc(Cl)ccc23)c1] | 1.12 | 584 | A |
| I-70 | (Chiral) | 1.12 | 584 | A |
| I-71 | (Chiral) | 1.12 | 584 | A |

TABLE 19-continued

| # | structure | $t_{ret}$ [min] | $[M + H]^+$ | HPLC method |
|---|---|---|---|---|
| I-72 | 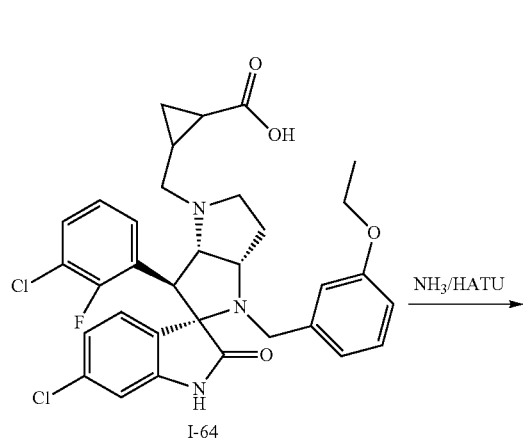 | 1.20 | 570 | A |
| I-73 | 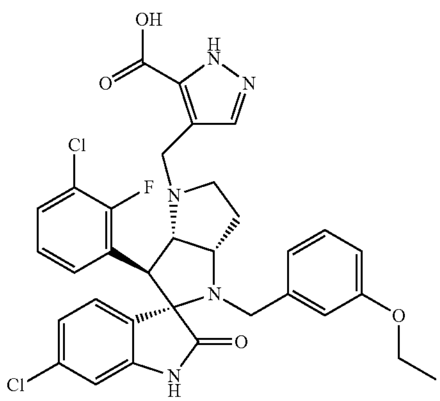 [SMILES: CCOc1cccc(CN2[C@H]3CCN(Cc4cn[nH]c4C(=O)O)[C@H]3[C@H](c3cccc(Cl)c3F)[C@]23C(=O)Nc2cc(Cl)ccc23)c1] | 1.31 | 650 | A |

Synthesis of Further Compounds (I) by Amidation of Initially Obtained Compounds (1)

Experimental Procedure for the Synthesis of I-74

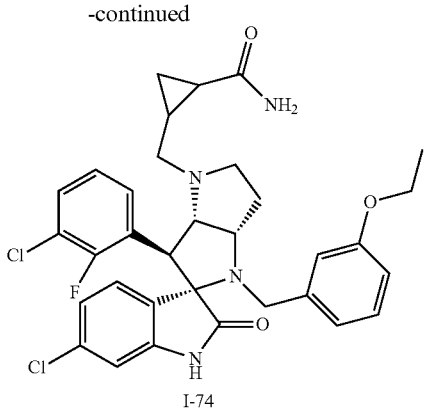

To a solution of I-65 (9 mg, 0.014 mmol) in DMF is added HATU (6 mg, 0.016 mmol), DIPEA (7.4 µL, 0.043 mmol) and the reaction mixture is stirred at rt for 15 min. Ammonia (2.2 µL, 0.03 mmol, 25% in $H_2O$) is added to the reaction mixture and stirred for 30 min. The reaction mixture is purified by prep. HPLC after filtration to give compound I-74.

The following compounds (1) (Table 20) are available in an analogous manner starting from initially obtained compounds (I).

TABLE 20

| # | Structure | $t_{ret}$ [min] | $[M + H]^+$ | HPLC method |
|---|---|---|---|---|
| I-74 | 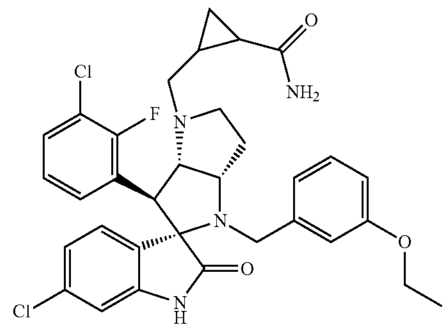 [SMILES: CCOc1cccc(CN2[C@H]3CCN(CC4CC4C(N)=O)[C@H]3[C@H](c3cccc(Cl)c3F)[C@]23C(=O)Nc2cc(Cl)ccc23)c1] | 1.38 | 623 | A |
| I-75 | 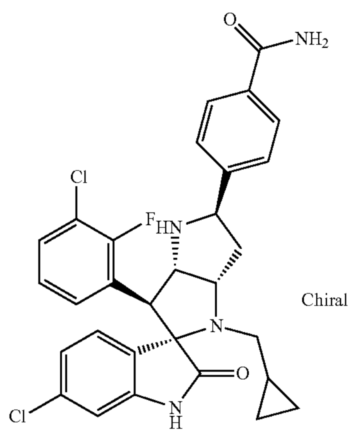 [SMILES: NC(=O)c1ccc([C@H]2C[C@H]3[C@@H](N2)[C@H](c2cccc(Cl)c2F)[C@]2(C(=O)Nc4cc(Cl)ccc42)N3CC2CC2)cc1] | 1.30 | 565 | A |

Synthesis of Intermediates A-15 by Acylation (Method R)

Experimental Procedure for the Synthesis of A-15i

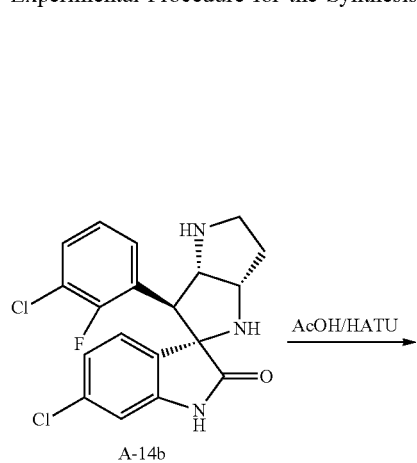

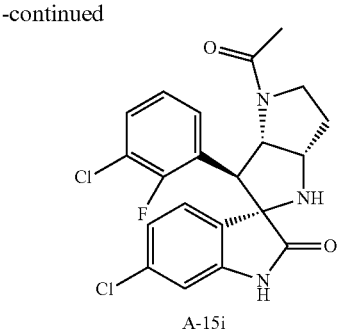

To a solution of AcOH (25 mg, 0.41 mmol) in DMF is added HATU (171 mg, 0.45 mmol) and DIPEA (263 μL, 1.63 mmol) and the reaction mixture is stirred for 5 min at rt. A-14b (160 mg, 0.41 mmol) is added to the reaction mixture and stirring is continued for 20 min. The reaction mixture is purified by prep. HPLC after filtration to give compound A-15i.

The following compounds A-15 (table 21) are available in an analogous manner starting from different intermediates A-14.

TABLE 21

| # | structure | $t_{ret}$ [min] | [M + H]+ | HPLC method |
|---|---|---|---|---|
| A-15i | 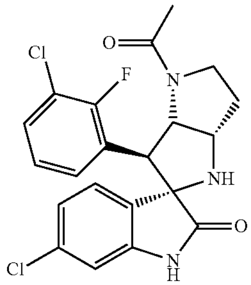 | 1.08 | 434 | A |
| A-15j | 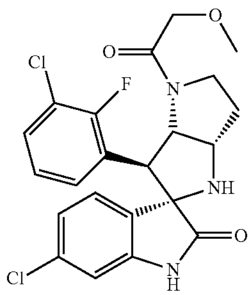 | 0.56 | 464 | C |
| A-15k | 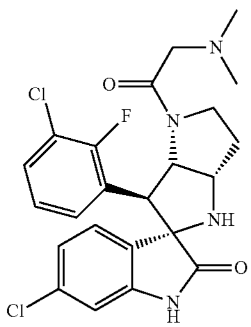 | 0.48 | 477 | C |
| A-15l | 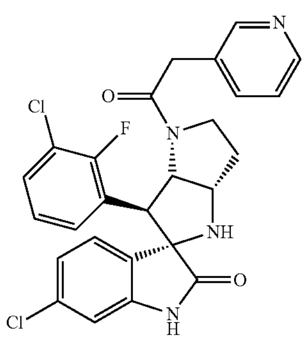 | 0.47 | 511 | C |
| A-15m | 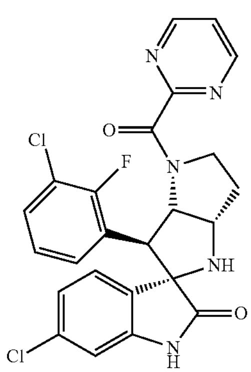 | 0.50 | 498 | C |

TABLE 21-continued

| # | structure | $t_{ret}$ [min] | [M + H]$^+$ | HPLC method |
|---|---|---|---|---|
| A-15n | 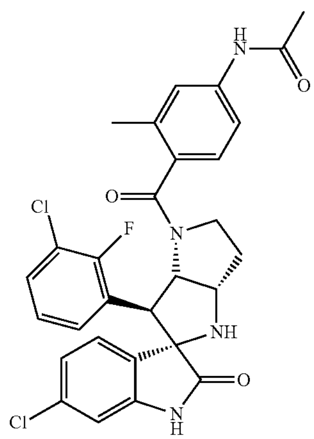 | 0.55 | 567 | C |
| A-15o | 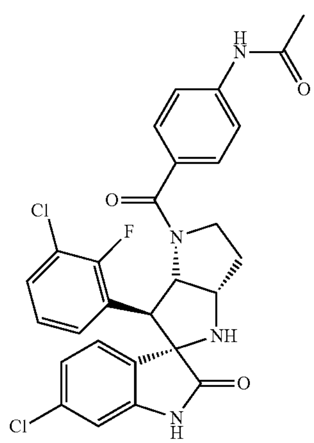 | 0.54 | 553 | C |
| A-15p | 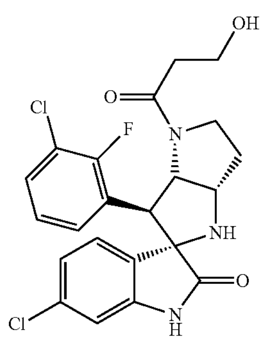 | 0.49 | 464 | C |
| A-15q | 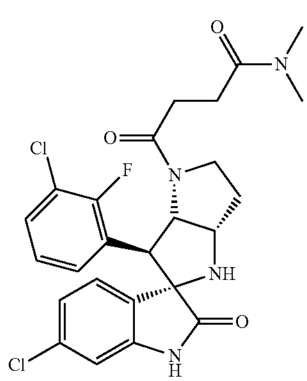 | 0.53 | 519 | C |

TABLE 21-continued
| # | structure | $t_{ret}$ [min] | [M + H]$^+$ | HPLC method |
|---|---|---|---|---|
| A-15r | 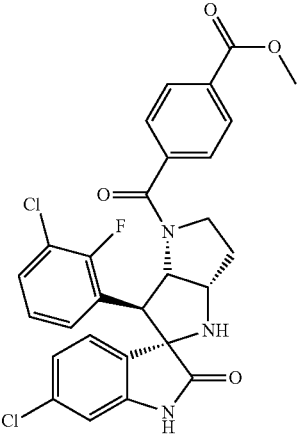 | 0.63 | 554 | C |
| A-15s | 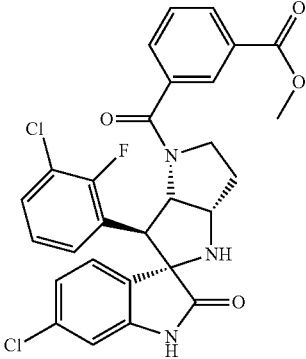 | 0.63 | 554 | C |
| A-15t | 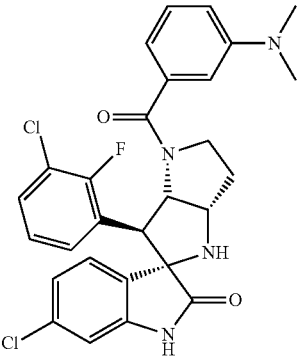 | 0.66 | 539 | C |
| A-15u | 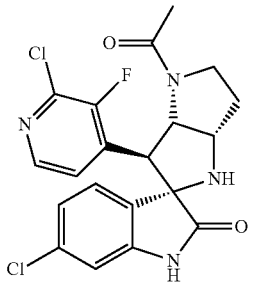 | 0.53 | 435 | C |

Synthesis of Compounds (I) According to the Invention

Experimental Procedure for the Synthesis of Compound I-76

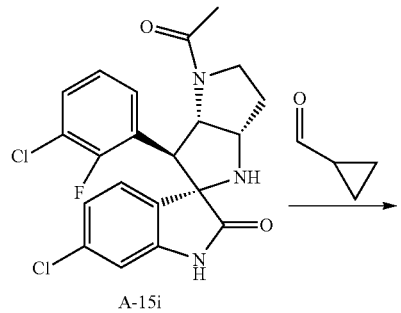

A-15i

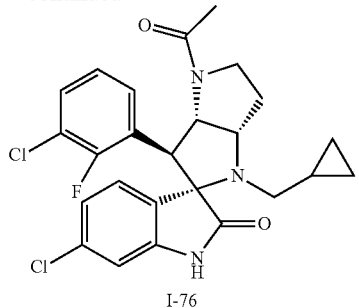

I-76

To a solution of cyclopropanecarbaldehyde (19 mg, 0.28 mmol) in acetonitrile is added intermediate A-15i (30 mg, 0.07 mmol) and acetic acid (150 µL) and the reaction mixture is stirred for 30 min. Sodium triacetoxyborohydride (19 mg, 0.28 mmol) is added and the reaction mixture is stirred for 2 h. To the reaction mixture is added water and saturated aqueous NaHCO$_3$ solution and it is extracted with DCM. The combined organic layer is dried (MgSO$_4$), filtered, concentrated in vacuo and the crude product is purified by prep. HPLC to give compound I-76

The following compounds (I) (table 22) are available in an analogous manner starting from different intermediates A-15.

TABLE 22

| # | structure | t$_{ret}$ [min] | [M + H]$^+$ | HPLC method |
|---|-----------|-----------------|-------------|-------------|
| I-76 | 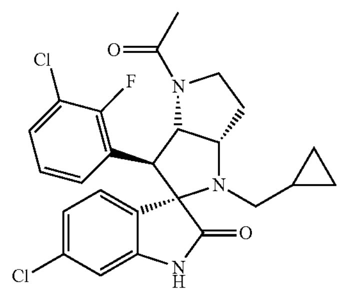 | 1.36 | 488 | A |
| I-77 | 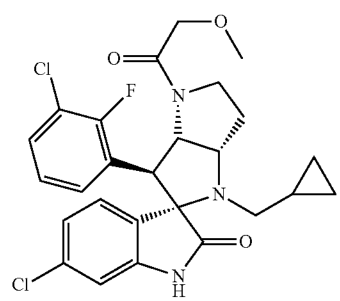 | 1.37 | 518 | A |
| I-78 | 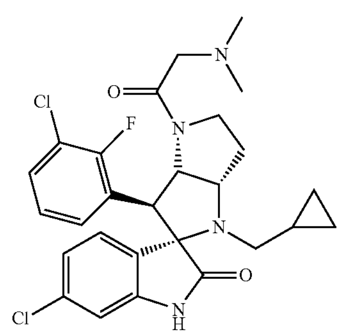 | 1.41 | 531 | A |

TABLE 22-continued

| # | structure | t_ret [min] | [M + H]+ | HPLC method |
|---|---|---|---|---|
| I-79 | 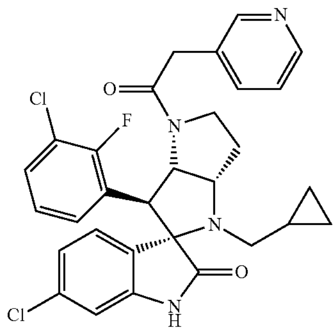 | 1.35 | 565 | A |
| I-80 | 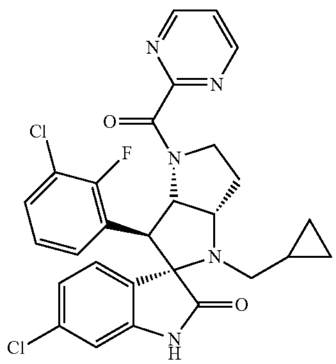 | 1.30 | 552 | A |
| I-81 | 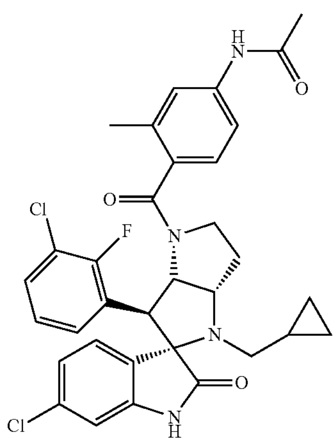 | 1.34 | 621 | A |
| I-82 | 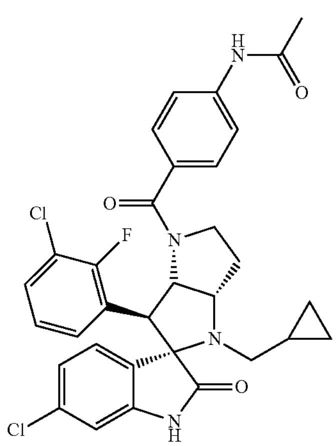 | 1.32 | 607 | A |

TABLE 22-continued

| # | structure | $t_{ret}$ [min] | [M + H]$^+$ | HPLC method |
|---|---|---|---|---|
| I-83 | 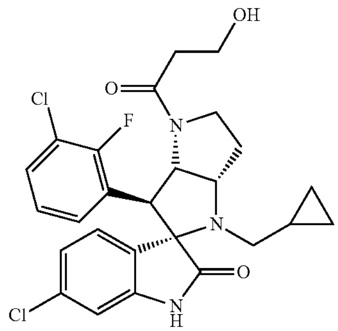 | 1.28 | 518 | A |
| I-84 | 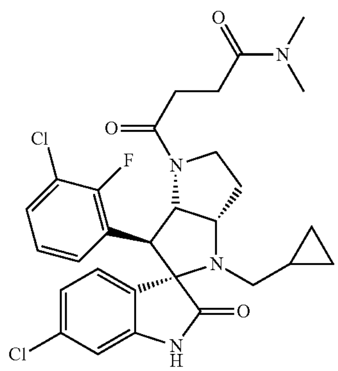 | 1.32 | 573 | A |
| I-85 | 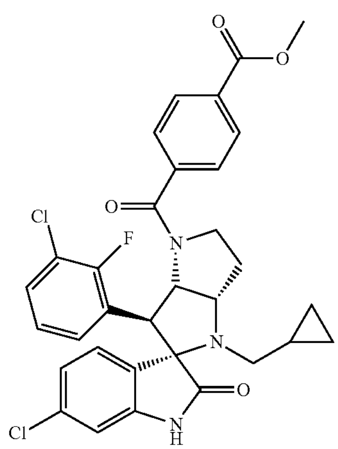 | 0.79 | 608 | C |
| I-86 | 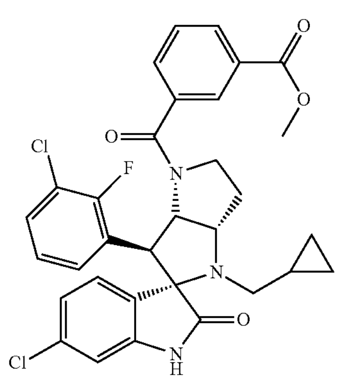 | 0.78 | 608 | C |

TABLE 22-continued

| # | structure | $t_{ret}$ [min] | [M + H]⁺ | HPLC method |
|---|---|---|---|---|
| I-87 | 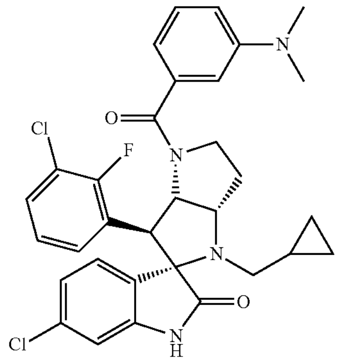 | 1.53 | 593 | A |
| I-88 | 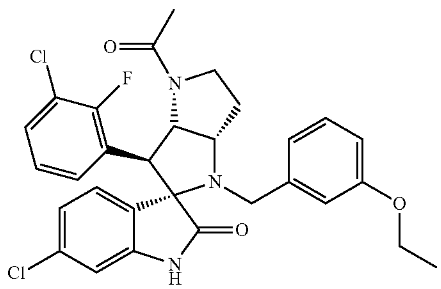 | 1.44 | 568 | A |
| I-89 | 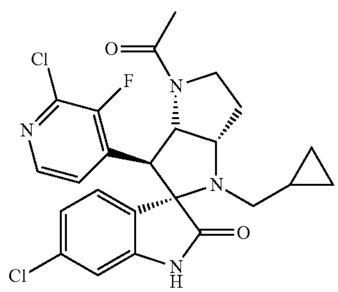 | 1.30 | 489 | A |
| I-90 | 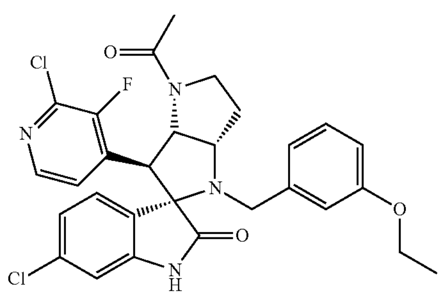 | 1.39 | 569 | A |
| I-91 | 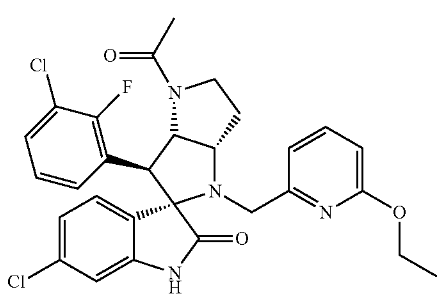 | 1.40 | 569 | A |

Synthesis of Further Compounds (I) by Ester Saponification of Initially Obtained Compounds (I)

Experimental Procedure for the Synthesis of I-92

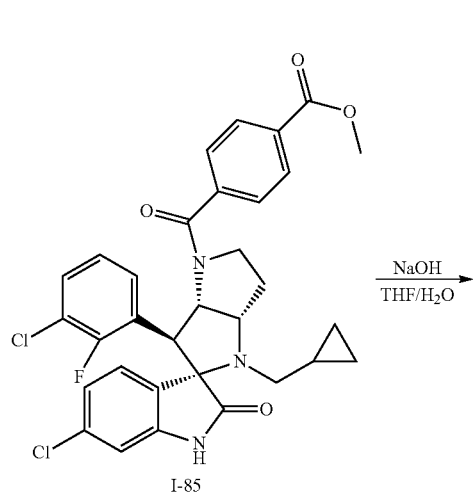

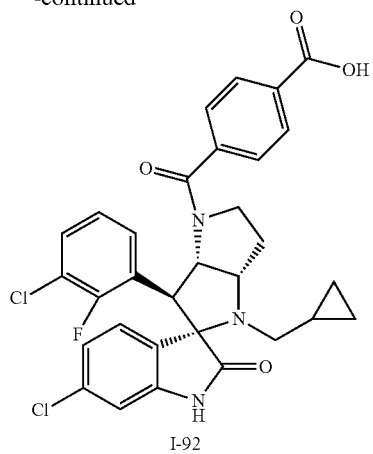

To a solution of compound I-85 (40 mg, 0.066 mmol) in THF is added NaOH (90 μL, 2 M in H$_2$O) and the reaction mixture is stirred at 75° C. for 1 h. The reaction mixture is concentrated in vacuo and purified by prep. HPLC to obtain compound I-92.

The following compounds (I) (table 23) are available in an analogous manner starting from different compounds (I).

TABLE 23

| # | structure | t$_{ret}$ [min] | [M + H]$^+$ | HPLC method |
|---|---|---|---|---|
| I-92 | 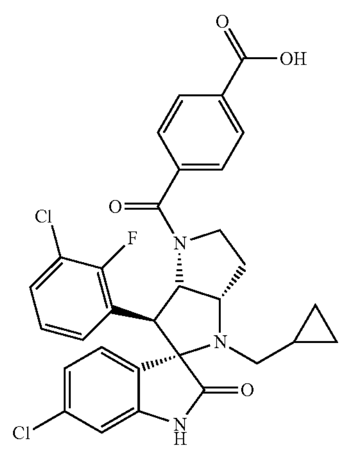 | 1.05 | 594 | A |
| I-93 | 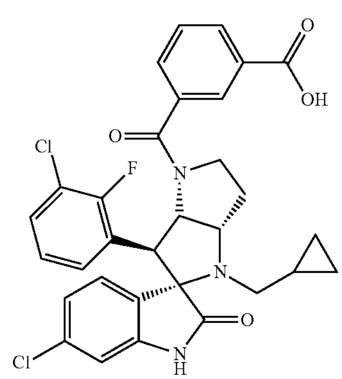 | 1.07 | 594 | A |

The following Examples describe the biological activity of the compounds according to the invention, without restricting the invention to these Examples.

Compounds of formulae (I), (Ia) and (Ib) are characterised by their many possible applications in the therapeutic field. Particular mention should be made of those applications in which the inhibiting effect on the proliferation of cultivated human tumour cells but also on the proliferation of other cells such as endothelial cells, for example, are involved.

Mdm2-p53 Inhibition AlphaScreen

This assay is used to determine whether the compounds inhibit the p53-MDM2 interaction and thus restore p53 function.

15 µL of compound in 20% DMSO (serial pre-dilutions of compound are done in 100% DMSO) is pipetted to the wells of a white OptiPlate-96 (PerkinElmer). A mix consisting of 20 nM GST-MDM2 protein (aa 23-117) and 20 nM biotinylated p53 wt peptide (encompassing aa 16-27 of wt human p53, amino acid sequence QETFSDLWKLLP-Ttds-Lys-Biotin, molecular weight 2132.56 g/mol) is prepared in assay buffer (50 mM Tris/HCl pH 7.2; 120 mM NaCl; 0.1% bovine serum albumin (BSA); 5 mM dithiothreitol (DTT); 1 mM ethylenediaminetetraacetic acid (EDTA); 0.01% Tween 20). 30 µL of the mix is added to the compound dilutions and incubated for 15 min at rt while gently shaking the plate at 300 rounds per minute (rpm). Subsequently, 15 µL of premixed AlphaLISA Glutathione Acceptor Beads and AlphaScreen Streptavidin Donor Beads from PerkinElmer (in assay buffer at a concentration of 10 µg/mL each) are added and the samples are incubated for 30 min at rt in the dark (shaking 300 rpm). Afterwards, the signal is measured in a PerkinElmer Envision HTS Multilabel Reader using the AlphaScreen protocol from PerkinElmer.

Each plate contains negative controls where biotinylated p53-peptide and GST-MDM2 are left out and replaced by assay buffer. Negative control values are entered as low basis value when using the software GraphPad Prism for calculations. Furthermore, a positive control (5% DMSO instead of test compound; with protein/peptide mix) is pipetted. Determination of $IC_{50}$ values are carried out using GraphPad Prism 3.03 software (or updates thereof).

Table 24 shows the $IC_{50}$ values of example compounds determined using the above assay.

TABLE 24

| # | $IC_{50}$ MDM2 [nM] |
|---|---|
| I-1 | 139 |
| I-13 | 623 |
| I-23 | 871 |
| I-24 | 23 |
| I-25 | 49 |
| I-26 | 173 |
| I-27 | 32 |
| I-28 | 249 |
| I-29 | 5 |
| I-30 | 41 |
| I-31 | 8 |
| I-32 | 373 |
| I-33 | 2 |
| I-34 | 4 |
| I-35 | 9 |
| I-36 | 4 |
| I-37 | 5 |
| I-38 | 2 |
| I-39 | 124 |
| I-40 | 133 |
| I-46 | 280 |
| I-47 | 280 |
| I-60 | 85 |

TABLE 24-continued

| # | $IC_{50}$ MDM2 [nM] |
|---|---|
| I-61 | 274 |
| I-62 | 24 |
| I-63 | 130 |
| I-64 | 6 |
| I-65 | 3 |
| I-66 | 209 |
| I-67 | 40 |
| I-68 | 91 |
| I-69 | 3 |
| I-70 | 2 |
| I-71 | 722 |
| I-72 | 1303 |
| I-73 | 29 |
| I-74 | 21 |
| I-75 | 16 |
| I-76 | 212 |
| I-77 | 119 |
| I-78 | 381 |
| I-79 | 386 |
| I-80 | 596 |
| I-81 | 444 |
| I-82 | 389 |
| I-83 | 102 |
| I-84 | 107 |
| I-87 | 607 |
| I-88 | 28 |
| I-89 | 34 |
| I-90 | 6 |
| I-91 | 180 |
| I-92 | 106 |
| I-93 | 377 |

Cell Proliferation Assays

Cell Titer Glo Assay for e.g. SJSA-1, SKOV-3, RS4-11 and KG-1 Cells:

SJSA-1 cells (Osteosarcoma, wildtype p53, ATCC CRL-2098TM) are seeded in duplicates at day 1 in flat bottom 96 well microtiter plates (white Packard View Plate 96 well Cat. No. 6005181) in 90 µL RPMI medium, 10% fetal calf serum (FCS, from e.g. JRH Biosciences #12103-500M, Lot.: 3N0207) at a density of 2500 cells/well. Any other luminescence compatible plate format is possible.

Similarly, p53 mutant SKOV-3 cells (ovarian adenocarcinoma, ATCC HTB-77™) are seeded in duplicates in flat bottom 96 well microtiter plates in 90 µL McCoy medium, 10% FCS at a density of 3000 cells/well.

At day 2, 5 µL dilutions of the test compounds covering a concentration range between app. 0.6 and 50000 nM are added to the cells. Cells are incubated for three days in a humidified, $CO_2$-controlled incubator at 37° C.

Wildtype p53 RS4-11 Cells (Acute Lymphoblastic Leukemia, ATCC CRL-1873™):

Day 1: RS4-11 cells are seeded in flat bottom 96 well microtiter plates (white Packard View Plate 96 well Cat. No. 6005181) in 90 µL RPMI medium, 10% fetal calf serum (FCS, from e.g. JRH Biosciences #12103-500M, Lot.: 3N0207) at a density of 5000 cells/well. Any other luminescence compatible plate format is possible.

Day 2: 5 µL dilutions of the test compounds covering a concentration range between app. 0.3 and 25000 nM (alternative dilution schemes are possible) are added to the cells. Cells are incubated for three days in a humidified, $CO_2$ controlled incubator at 37° C. The final DMSO-concentration is 0.5%.

p53 Mutant KG-1 Cells (Acute Myelogenous Leukemia, ATCC CCL-246):

Day 1: KG-1 cells harboring a p53 mutation at the exon 6/intron 6 splice donor site are seeded in flat bottom 96 well microtiter plates (white Packard View Plate 96 well Cat. No.

6005181) in 90 μL IMDM medium, 10% FCS (JRH Biosciences #12103-500M, Lot.: 3N0207) at a density of 10000 cells/well. Any other luminescence compatible plate format is possible.

Day 2: 5 μL dilutions of the test compounds covering a concentration range between app. 0.3 and 25000 nM (alternative dilution schemes are possible) are added to the cells. Cells are incubated for three days in a humidified, $CO_2$ controlled incubator at 37° C. The final DMSO-concentration is 0.5%.

Evaluation of all Cell Titer Glo assays is done at day 5 after seeding. At day 5, 95 μL of Cell Titer Glo reagent (Cell titer Glo Luminescent Cat. No. G7571, Promega) are added to each well and incubated for additional 10 min at rt (with agitation). Luminescence is measured on a Wallac Victor using standard luminescence read out. $IC_{50}$ values are calculated using standard Levenburg Marquard algorithms (GraphPad Prism).

In addition, several other cancer cell lines from diverse tissue origins proved to be sensitive to compounds (I), (Ia) and (Ib). Examples include NCI-H460 (lung), Molp-8 (myeloma) and MV4-11 (AML).

On the basis of their biological properties the compounds of formula (I), (Ia) and (Ib) according to the invention, their tautomers, racemates, enantiomers, diastereomers, mixtures thereof and the salts of all the above-mentioned forms are suitable for treating diseases characterised by excessive or abnormal cell proliferation.

Such diseases include for example: viral infections (e.g. HIV and Kaposi's sarcoma); inflammatory and autoimmune diseases (e.g. colitis, arthritis, Alzheimer's disease, glomerulonephritis and wound healing); bacterial, fungal and/or parasitic infections; leukaemias, lymphomas and solid tumours (e.g. carcinomas and sarcomas), skin diseases (e.g. psoriasis); diseases based on hyperplasia which are characterised by an increase in the number of cells (e.g. fibroblasts, hepatocytes, bones and bone marrow cells, cartilage or smooth muscle cells or epithelial cells (e.g. endometrial hyperplasia); bone diseases and cardiovascular diseases (e.g. restenosis and hypertrophy). They are also suitable for protecting proliferating cells (e.g. hair, intestinal, blood and progenitor cells) from DNA damage caused by radiation, UV treatment and/or cytostatic treatment.

For example, the following cancers/proliferative diseases may be treated with compounds according to the invention, without being restricted thereto:
brain tumours such as for example acoustic neurinoma, astrocytomas such as pilocytic astrocytomas, fibrillary astrocytoma, protoplasmic astrocytoma, gemistocytary astrocytoma, anaplastic astrocytoma and glioblastoma, glioma, brain lymphomas, brain metastases, hypophyseal tumour such as prolactinoma, HGH (human growth hormone) producing tumour and ACTH producing tumour (adrenocorticotropic hormone), craniopharyngiomas, medulloblastomas, meningeomas and oligodendrogliomas; nerve tumours (neoplasms) such as for example tumours of the vegetative nervous system such as neuroblastoma sympathicum, ganglioneuroma, paraganglioma (pheochromocytoma, chromaffinoma) and glomus-caroticum tumour, tumours on the peripheral nervous system such as amputation neuroma, neurofibroma, neurinoma (neurilemmoma, Schwannoma) and malignant Schwannoma, as well as tumours of the central nervous system such as brain and bone marrow tumours; intestinal cancer such as for example carcinoma of the rectum, colon carcinoma, colorectal carcinoma, anal carcinoma, carcinoma of the large bowel, tumours of the small intestine and duodenum; eyelid tumours such as basalioma or basal cell carcinoma; pancreatic cancer or carcinoma of the pancreas; bladder cancer or carcinoma of the bladder and other urothelial cancers; lung cancer (bronchial carcinoma) such as for example small-cell bronchial carcinomas (oat cell carcinomas) and non-small cell bronchial carcinomas (NSCLC) such as plate epithelial carcinomas, adenocarcinomas and large-cell bronchial carcinomas; breast cancer such as for example mammary carcinoma such as infiltrating ductal carcinoma, colloid carcinoma, lobular invasive carcinoma, tubular carcinoma, adenocystic carcinoma and papillary carcinoma, hormone receptor positive breast cancer (estrogen receptor positive breast cancer, progesterone receptor positive breast cancer), Her2 positive breast cancer, triple negative breast cancer; non-Hodgkin's lymphomas (NHL) such as for example Burkitt's lymphoma, low-malignancy non-Hodgkin's lymphomas (NHL) and mucosis fungoides; uterine cancer or endometrial carcinoma or corpus carcinoma; CUP syndrome (Cancer of Unknown Primary); ovarian cancer or ovarian carcinoma such as mucinous, endometrial or serous cancer; gall bladder cancer; bile duct cancer such as for example Klatskin tumour; testicular cancer such as for example seminomas and non-seminomas; lymphoma (lymphosarcoma) such as for example malignant lymphoma, Hodgkin's disease, non-Hodgkin's lymphomas (NHL) such as chronic lymphatic leukaemia, leukaemic reticuloendotheliosis, immunocytoma, plasmocytoma (multiple myeloma, MM), immunoblastoma, Burkitt's lymphoma, T-zone mycosis fungoides, large-cell anaplastic lymphoblastoma and lymphoblastoma; laryngeal cancer such as for example tumours of the vocal cords, supraglottal, glottal and subglottal laryngeal tumours; bone cancer such as for example osteochondroma, chondroma, chondroblastoma, chondromyxoid fibroma, osteoma, osteoid osteoma, osteoblastoma, eosinophilic granuloma, giant cell tumour, chondrosarcoma, osteosarcoma, Ewing's sarcoma, reticulo-sarcoma, soft tissue sarcoma, liposarcoma, plasmocytoma, fibrous dysplasia, juvenile bone cysts and aneurysmatic bone cysts; head and neck tumours such as for example tumours of the lips, tongue, floor of the mouth, oral cavity, gums, palate, salivary glands, throat, nasal cavity, paranasal sinuses, larynx and middle ear; liver cancer such as for example liver cell carcinoma or hepatocellular carcinoma (HCC); leukaemias, such as for example acute leukaemias such as acute lymphatic/lymphoblastic leukaemia (ALL), acute myeloid leukaemia (AML); chronic leukaemias such as chronic lymphatic leukaemia (CLL), chronic myeloid leukaemia (CML); stomach cancer or gastric carcinoma such as for example papillary, tubular and mucinous adenocarcinoma, signet ring cell carcinoma, adenosquamous carcinoma, small-cell carcinoma and undifferentiated carcinoma; melanomas such as for example superficially spreading, nodular, lentigo-maligna and acral-lentiginous melanoma; renal cancer such as for example kidney cell carcinoma or hypernephroma or Grawitz's tumour; oesophageal cancer or carcinoma of the oesophagus; penile cancer; prostate cancer (e.g. castration-resistant prostate cancer); throat cancer or carcinomas of the pharynx such as for example nasopharynx carcinomas, oropharynx carcinomas and hypopharynx carcinomas; retinoblastoma, vaginal cancer or vaginal carcinoma, mesothelioma; plate epithelial carcinomas, adenocarcinomas, in situ carcinomas, malignant melanomas and sarcomas; thyroid carcinomas such as for example papillary, follicular and medullary thyroid carcinoma, as well as anaplastic carcinomas; spinalioma, epidormoid carcinoma and plate epithelial carcinoma of the skin; thymomas, cancer of the urethra, cervical cancer, adenoid cystic carcinoma (AdCC), adrenocortical carcinoma and cancer of the vulva.

Preferably, the proliferative diseases/cancers to be treated have p53 wild-type status.

The new compounds may be used for the prevention, short-term or long-term treatment of the above-mentioned diseases, optionally also in combination with radiotherapy or other "state-of-the-art" compounds, such as e.g. cytostatic or cytotoxic substances, cell proliferation inhibitors, anti-angiogenic substances, steroids or antibodies.

The compounds of formula (I), (Ia) and (Ib) may be used on their own or in combination with other active substances according to the invention, optionally also in combination with other pharmacologically active substances.

Therapeutic agents which may be administered in combination with the compounds according to the invention, include, without being restricted thereto, hormones, hormone analogues and antihormones (e.g. tamoxifen, toremifene, raloxifene, fulvestrant, megestrol acetate, flutamide, nilutamide, bicalutamide, aminoglutethimide, cyproterone acetate, finasteride, buserelin acetate, fludrocortisone, fluoxymesterone, medroxy-progesterone, octreotide), aromatase inhibitors (e.g. anastrozole, letrozole, liarozole, vorozole, exemestane, atamestane), LHRH agonists and antagonists (e.g. goserelin acetate, luprolide), inhibitors of growth factors (growth factors such as for example "platelet derived growth factor (PDGF)", "fibroblast growth factor (FGF)", "vascular endothelial growth factor (VEGF)", "epidermal growth factor (EGF)", "insuline-like growth factors (IGF)", "human epidermal growth factor (HER, e.g. HER2, HER3, HER4)" and "hepatocyte growth factor (HGF)"), inhibitors are for example "growth factor" antibodies, "growth factor receptor" antibodies and tyrosine kinase inhibitors, such as for example cetuximab, gefitinib, imatinib, lapatinib and trastuzumab); antimetabolites (e.g. antifolates such as methotrexate, raltitrexed, pyrimidine analogues such as 5-fluorouracil (5-FU), capecitabin and gemcitabin, purine and adenosine analogues such as mercaptopurine, thioguanine, cladribine and pentostatin, cytarabine (ara C), fludarabine); antitumour antibiotics (e.g. anthracyclins such as doxorubicin, daunorubicin, epirubicin and idarubicin, mitomycin-C, bleomycin, dactinomycin, plicamycin, streptozocin); platinum derivatives (e.g. cisplatin, oxaliplatin, carboplatin); alkylation agents (e.g. estramustin, meclorethamine, melphalan, chlorambucil, busulphan, dacarbazin, cyclophosphamide, ifosfamide, temozolomide, nitrosoureas such as for example carmustin and lomustin, thiotepa); antimitotic agents (e.g. Vinca alkaloids such as for example vinblastine, vindesin, vinorelbin and vincristine; and taxanes such as paclitaxel, docetaxel); angiogenesis inhibitors (e.g. tasquinimod), tubuline inhibitors; DNA synthesis inhibitors (e.g. sapacitabine), PARP inhibitors, topoisomerase inhibitors (e.g. epipodophyllotoxins such as for example etoposide and etopophos, teniposide, amsacrin, topotecan, irinotecan, mitoxantrone), serine/threonine kinase inhibitors (e.g. PDK 1 inhibitors, B-Raf inhibitors, mTOR inhibitors, mTORC1/2 inhibitors, PI3K inhibitors, dual mTOR/PI3K inhibitors, STK 33 inhibitors, AKT inhibitors, PLK 1 inhibitors, inhibitors of CDKs, Aurora kinase inhibitors), tyrosine kinase inhibitors (e.g. PTK2/FAK inhibitors), protein protein interaction inhibitors (e.g. IAP activator, Mcl-1, MDM2/MDMX), MEK inhibitors (e.g. pimasertib), ERK inhibitors, FLT3 inhibitors (e.g. quizartinib), BRD4 inhibitors, IGF-1R inhibitors, TRAILR2 agonists, Bcl-2 inhibitors (e.g. venetoclax), ErbB receptor inhibitors, rapamycin analogs (e.g. everolimus, temsirolimus, ridaforolimus, sirolimus), androgen synthesis inhibitors (e.g. abiraterone, TAK-700), androgen receptor inhibitors (e.g. enzalutamide, ARN-509), immunotherapy (e.g. sipuleucel-T), DNMT inhibitors (e.g. SGI 110, temozolomide, vosaroxin), HDAC inhibitors (e.g. vorinostat, entinostat, pracinostat, panobinostat), ANG1/2 inhibitors (e.g. trebananib), CYP17 inhibitors (e.g. galeterone), radiopharmaceuticals (e.g. radium-223, alpharadin), immunotherapeutic agents (e.g. poxvirus-based vaccine, ipilimumab) and various chemotherapeutic agents such as amifostin, anagrelid, clodronat, filgrastin, interferon, interferon alpha, leucovorin, rituximab, procarbazine, levamisole, mesna, mitotane, pamidronate and porfimer.

Other possible combination partners are 2-chlorodesoxy-adenosine, 2-fluorodesoxy-cytidine, 2-methoxyoestradiol, 2C4,3-alethine, 131-I-TM-601, 3CPA, 7-ethyl-10-hydroxycamptothecin, 16-aza-epothilone B, ABT-263/navitoclax, A 105972, A 204197, aldesleukin, alisertib/MLN8237, alitretinoin, allovectin-7, altretamine, alvocidib, amonafide, anthrapyrazole, AG-2037, AP-5280, apaziquone, apomine, aranose, arglabin, arzoxifene, atamestane, atrasentan, auristatin PE, AVLB, AZ10992, ABX-EGF, AMG-479 (ganitumab), AMG-232, ARRY 162, ARRY 438162, ARRY-300, ARRY-142886/AZD-6244 (selumetinib), ARRY-704/AZD-8330, ATSP-7041, AR-12, AR-42, AS-703988, AXL-1717, AZD-1480, AZD-4547, AZD-8055, AZD-5363, AZD-6244, AZD-7762, ARO-736, ARQ 680, AS-703026 (primasertib), avastin, AZD-2014, azacitidine (5-aza), azaepothilone B, azonafide, barasertib/AZD1152, BAY-43-9006, BAY 80-6946, BBR-3464, BBR-3576, bevacizumab, BEZ-235/dactolisib, biricodar dicitrate, birinapant, BCX-1777, BKM-120/buparlisib, bleocin, BLP-25, BMS-184476, BMS-247550, BMS-188797, BMS-275291, BMS-663513, BMS-754807, BNP-1350, BNP-7787, BIBW 2992/afatinib, BIBF 1120/nintedanib, BI 836845, BI 2536, BI 6727/volasertib, BI 836845, BI 847325, BI 853520, BIIB-022, bleomycinic acid, bleomycin A, bleomycin B, brivanib, bryostatin-1, bortezomib, brostallicin, busulphan, BYL-719/alpelisib, CA-4 prodrug, CA-4, cabazitaxel, cabozantinib, CapCell, calcitriol, canertinib, canfosfamide, capecitabine, carboxyphthalatoplatin, CCI-779, CC-115, CC-223, CEP-701, CEP-751, CBT-1 cefixime, ceflatonin, ceftriaxone, celecoxib, celmoleukin, cemadotin, CGM-097, CH4987655/RO-4987655, chlorotrianisene, cilengitide, ciclosporin, CDA-II, CDC-394, CKD-602, CKI-27, clofarabine, colchicin, combretastatin A4, COT inhibitors, CHS-828, CH-5132799, CLL-Thera, CMT-3 cryptophycin 52, CPI-613, CTP-37, CTLA-4 monoclonal antibodies, CP-461, crizotinib, CV-247, cyanomorpholinodoxorubicin, cytarabine, D 24851, dasatinib, decitabine, deoxorubicin, deoxyrubicin, deoxycoformycin, depsipeptide, desoxyepothilone B, dexamethasone, dexrazoxanet, diethylstilbestrol, diflomotecan, didox, DMDC, dolastatin 10, doranidazole, DS-7423, DS-3032, E7010, E-6201, edatrexat, edotreotide, efaproxiral, eflornithine, EGFR inhibitors, EKB-569, EKB-509, enzastaurin, elesclomol, elsamitrucin, epothilone B, epratuzumab, EPZ-004777, ER-86526, erlotinib, ET-18-OCH3, ethynylcytidine, ethynyloestradiol, exatecan, exatecan mesylate, exemestane, exisulind, fenretinide, figitumumab, floxuridine, folic acid, FOLFOX, FOLFOX4, FOLFIRI, formestane, fostamatinib, fotemustine, galarubicin, gallium maltolate, ganetespib, gefinitib, gemtuzumab, gemtuzumab ozogamicin, gimatecan, glufosfamide, GCS-IOO, GDC-0623, GDC-0941 (pictrelisib), GDC-0980, GDC-0032, GDC-0068, GDC-0349, GDC-0879, G17DT immunogen, GMK, GMX-1778, GPX-100, gp100-peptide vaccines, GSK-5126766, GSK-690693, GSK-1120212 (trametinib), GSK-1995010, GSK-2118436 (dabrafenib), GSK-2126458, GSK-2132231A, GSK-2334470, GSK-2110183, GSK-2141795, GSK-2636771, GSK-525762A/I-BET-762, GW2016, granisetron, herceptine, hexamethylmelamine, histamine, homoharringtonine, hyaluronic acid, hydroxyurea, hydroxyprogesterone caproate, HDM-201, ibandronate, ibritumomab, ibrutinib/PCI-32765, idasanutlin, idatrexate, idelalisib/CAL-101, idenestrol, IDN-5109, IGF-1R inhibitors, IMC-1C11, IMC-A12 (cixutumumab), immunol, indisulam, interferon alpha-2a, interferon alpha-2b, pegylated interferon alpha-2b, interleukin-2, INK-1117, INK-128, INSM-18, ionafarnib, iproplatin, irofulven, isohomohalichondrin-B, isoflavone, isotretinoin, ixabepilone, JRX-2, JSF-154, JQ-1, J-107088, conjugated oestrogens, kahalid F, ketoconazole, KW-2170, KW-2450, KU-55933, LCL-161, lobaplatin, leflunomide, lenalidomide, lenograstim, leuprolide, leuporelin, lexidronam, LGD-1550, linezolid, lovastatin, lutetium texaphyrin, lometrexol, lonidamine, losoxantrone, LU 223651, lurbinectedin, lurtotecan, LY-S6AKT1, LY-2780301, LY-2109761/galunisertib, mafosfam ide, marimastat, masoprocol, mechloroethamine, MEK inhibitors, MEK-162, methyltestosteron, methylprednisolone, MEDI-573, MEN-10755, MDX-H210, MDX-447, MDX-1379, MGV, midostaurin, minodronic acid, mitomycin, mivobulin, MK-2206, MK-0646 (dalotuzumab), MLN518, MLN-0128, motexafin gadolinium, MS-209, MS-275, MX6, neridronate, neratinib, Nexavar, neovastat, nilotinib, nimesulide, nitroglycerin, nolatrexed, norelin, N-acetylcysteine, NU-7441 06-benzylguanine, oblimersen, omeprazole, olaparib, oncophage, oncoVEX$^{GM-CSF}$, ormiplatin, ortataxel, OX44 antibodies, OSI-027, OSI-906 (linsitinib), 4-1BB antibodies, oxantrazole, oestrogen, onapristone, palbociclib/PD-0332991, panitumumab, panobinostat, patupilone, pazopanib, pegfilgrastim, PCK-3145, pegfilgrastim, PBI-1402, PBI-05204, PD0325901, PD-1 antibodies, PD-616, PEG-paclitaxel, albumin-stabilized paclitaxel, PEP-005, PF-05197281, PF-05212384, PF-04691502, PF-3758309, PHA-665752, PHT-427, P-04, PKC412, P54, PI-88, pelitinib, pemetrexed, pentrix, perifosine, perillylalcohol, pertuzumab, pevonedistat, PI3K inhibitors, PI3K/mTOR inhibitors, PG-TXL, PG2, PLX-4032/RO-5185426 (vemurafenib), PLX-3603/RO-5212054, PT-100, PWT-33597, PX-866, picoplatin, pivaloyloxymethylbutyrate, pixantrone, phenoxodiol 0, PK1166, plevitrexed, plicamycin, polyprenic acid, ponatinib, porfiromycin, posaconazole, prednisone, prednisolone, PRT-062607, quinamed, quinupristin, quizartinib/AC220, R115777, RAF-265, ramosetron, ranpirnase, RDEA-119/BAY 869766, RDEA-436, rebeccamycin analogues, receptor tyrosine kinase (RTK) inhibitors, revimid, RG-7167, RG-7112, RG-7304, RG-7421, RG-7321, RG-7356, RG 7440, RG-7775, rhizoxin, rhu-MAb, rigosertib rinfabate, risedronate, rituximab, robatumumab, rofecoxib, romidepsin, RO-4929097, RO-31-7453, RO-5126766, RO-5068760, RPR 109881A, rubidazone, rubitecan, R-flurbiprofen, RX-0201, ruxolitinib, S-9788, sabarubicin, SAHA, sapacitabine, SAR-405838, sargramostim, satraplatin, SB-408075, SB-431542, Se-015/Ve-015, SU5416, SU6668, SDX-101, selinexor, semustin, seocalcitol, SM-11355, SN-38, SN-4071, SR-27897, SR-31747, SR-13668, SRL-172, sorafenib, spiroplatin, squalamine, STF-31, suberanilohydroxamic acid, sutent, T 900607, T 138067, TAE-684, TAK-733, TAS-103, tacedinaline, talaporfin, Tarceva, tariquitar, tasisulam, taxotere, taxoprexin, tazarotene, tegafur, temozolamide, tesmilifene, testosterone, testosterone propionate, tesmilifene, tetraplatin, tetrodotoxin, tezacitabine, thalidomide, theralux, therarubicin, thymalfasin, thymectacin, tiazofurin, tipifarnib, tirapazamine, tocladesine, tomudex, toremofin, tosedostat, trabectedin, TransMID-107, transretinic acid, traszutumab, tremelimumab, tretinoin, triacetyluridine, triapine, triciribine, trimetrexate, TLK-286TXD 258, tykerb/tyverb, urocidin, valproic acid, valrubicin, vandetanib, vatalanib, vincristine, vinflunine, virulizin, vismodegib, vosaroxin, WX-UK1, WX-554, vectibix, XAV-939, xeloda, XELOX, XL-147, XL-228, XL-281, XL-518/R-7420/GDC-0973, XL-765, YM-511, YM-598, ZD-4190, ZD-6474, ZD-4054, ZD-0473, ZD-6126, ZD-9331, ZD1839, ZSTK-474, zoledronat and zosuquidar.

Suitable preparations include for example tablets, pills, capsules, suppositories, lozenges, troches, solutions—particularly solutions for injection (s.c., i.v., i.m.) and infusion (injectables)—elixirs, syrups, sachets, emulsions, inhalatives or dispersible powders. The content of the pharmaceutically active compound(s) should be in the range from 0.1 to 90 wt.-%, preferably 0.5 to 50 wt.-% of the composition as a whole, i.e. in amounts which are sufficient to achieve the dosage range specified below. The doses specified may, if necessary, be given several times a day.

Suitable tablets may be obtained, for example, by mixing the active substance(s) with known excipients, for example inert diluents such as calcium carbonate, calcium phosphate or lactose, disintegrants such as corn starch or alginic acid, binders such as starch or gelatine, lubricants such as magnesium stearate or talc, agents for delaying release, such as carboxymethyl cellulose, cellulose acetate phthalate, or polyvinyl acetate, carriers, adjuvants, surfactants. The tablets may also comprise several layers.

Coated tablets may be prepared accordingly by coating cores produced analogously to the tablets with substances normally used for tablet coatings, for example collidone or shellac, gum arabic, talc, titanium dioxide or sugar. To achieve delayed release or prevent incompatibilities the core may also consist of a number of layers. Similarly the tablet coating may consist of a number of layers to achieve delayed release, possibly using the excipients mentioned above for the tablets.

Syrups or elixirs containing the active substances or combinations thereof according to the invention may additionally contain a sweetener such as saccharine, cyclamate, glycerol or sugar and a flavour enhancer, e.g. a flavouring such as vanillin or orange extract. They may also contain suspension adjuvants or thickeners such as sodium carboxymethyl cellulose, wetting agents such as, for example, condensation products of fatty alcohols with ethylene oxide, or preservatives such as p-hydroxybenzoates.

Solutions for injection and infusion are prepared in the usual way, e.g. with the addition of isotonic agents, preservatives such as p-hydroxybenzoates, or stabilisers such as alkali metal salts of ethylenediamine tetraacetic acid, optionally using emulsifiers and/or dispersants, whilst if water is used as the diluent, for example, organic solvents may optionally be used as solvating agents or dissolving aids, and transferred into injection vials or ampoules or infusion bottles.

Capsules containing one or more active substances or combinations of active substances may for example be prepared by mixing the active substances with inert carriers such as lactose or sorbitol and packing them into gelatine capsules.

Suitable suppositories may be made for example by mixing with carriers provided for this purpose such as neutral fats or polyethyleneglycol or the derivatives thereof.

Excipients which may be used include, for example, water, pharmaceutically acceptable organic solvents such as paraffins (e.g. petroleum fractions), vegetable oils (e.g.

groundnut or sesame oil), mono- or polyfunctional alcohols (e.g. ethanol or glycerol), carriers such as e.g. natural mineral powders (e.g. kaolins, clays, talc, chalk), synthetic mineral powders (e.g. highly dispersed silicic acid and silicates), sugars (e.g. cane sugar, lactose and glucose), emulsifiers (e.g. lignin, spent sulphite liquors, methylcellulose, starch and polyvinylpyrrolidone) and lubricants (e.g. magnesium stearate, talc, stearic acid and sodium lauryl sulphate).

The preparations are administered by the usual methods, preferably by oral or transdermal route, most preferably by oral route. For oral administration the tablets may of course contain, apart from the above-mentioned carriers, additives such as sodium citrate, calcium carbonate and dicalcium phosphate together with various additives such as starch, preferably potato starch, gelatine and the like. Moreover, lubricants such as magnesium stearate, sodium lauryl sulphate and talc may be used at the same time for the tabletting process. In the case of aqueous suspensions the active substances may be combined with various flavour enhancers or colourings in addition to the excipients mentioned above.

For parenteral use, solutions of the active substances with suitable liquid carriers may be used.

The dosage range of the compounds of formula (I), (Ia) and (Ib) applicable per day is usually from 1 mg to 2000 mg, preferably from 50 to 1000 mg, more preferably from 100 to 500 mg.

The dosage for intravenous use is from 1 mg to 1000 mg per hour, preferably between 5 mg and 500 mg per hour.

However, it may sometimes be necessary to depart from the amounts specified, depending on the body weight, the route of administration, the individual response to the drug, the nature of its formulation and the time or interval over which the drug is administered. Thus, in some cases it may be sufficient to use less than the minimum dose given above, whereas in other cases the upper limit may have to be exceeded. When administering large amounts it may be advisable to divide them up into a number of smaller doses spread over the day.

The formulation examples which follow illustrate the present invention without restricting its scope:

Examples of Pharmaceutical Formulations

| A) Tablets | per tablet |
|---|---|
| active substance according to formulae (I) or (Ia) or (Ib) | 100 mg |
| lactose | 140 mg |
| corn starch | 240 mg |
| polyvinylpyrrolidone | 15 mg |
| magnesium stearate | 5 mg |
| | 500 mg |

The finely ground active substance, lactose and some of the corn starch are mixed together. The mixture is screened, then moistened with a solution of polyvinylpyrrolidone in water, kneaded, wet-granulated and dried. The granules, the remaining corn starch and the magnesium stearate are screened and mixed together. The mixture is compressed to produce tablets of suitable shape and size.

| B) Tablets | per tablet |
|---|---|
| active substance according to formulae (I) or (Ia) or (Ib) | 80 mg |
| lactose | 55 mg |
| corn starch | 190 mg |

-continued

| B) Tablets | per tablet |
|---|---|
| microcrystalline cellulose | 35 mg |
| polyvinylpyrrolidone | 15 mg |
| sodiumcarboxymethyl starch | 23 mg |
| magnesium stearate | 2 mg |
| | 400 mg |

The finely ground active substance, some of the corn starch, lactose, microcrystalline cellulose and polyvinylpyrrolidone are mixed together, the mixture is screened and worked with the remaining corn starch and water to form a granulate which is dried and screened. The sodiumcarboxymethyl starch and the magnesium stearate are added and mixed in and the mixture is compressed to form tablets of a suitable size.

| C) Ampoule solution | |
|---|---|
| active substance according to formulae (I) or (Ia) | 50 mg |
| sodium chloride | 50 mg |
| water for inj. | 5 mL |

The active substance is dissolved in water at its own pH or optionally at pH 5.5 to 6.5 and sodium chloride is added to make it isotonic. The solution obtained is filtered free from pyrogens and the filtrate is transferred under aseptic conditions into ampoules which are then sterilised and sealed by fusion. The ampoules contain 5 mg, 25 mg and 50 mg of active substance.

The invention claimed is:

1. A compound of formula (I)

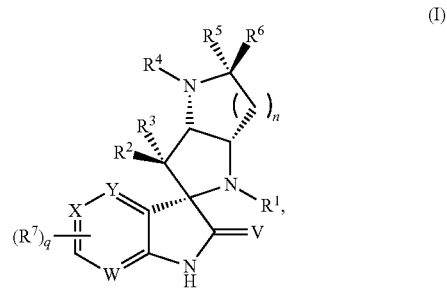

wherein
R$^1$ is C$_{1-6}$alkyl, optionally substituted by a group selected from the group consisting of C$_{3-6}$cycloalkyl, phenyl and 5-6 membered heteroaryl, wherein this C$_{3-6}$cycloalkyl, phenyl and 5-6 membered heteroaryl is optionally substituted by one or more, identical or different substituents selected from the group consisting of —OC$_{1-6}$alkyl, halogen, C$_{1-6}$alkyl and C$_{1-6}$haloalkyl;
one of R$^2$ and R$^3$ is hydrogen and the other is selected from the group consisting of phenyl and 5-6 membered heteroaryl, wherein this phenyl and 5-6 membered heteroaryl is optionally substituted by one or more, identical or different halogen(s);
R$^4$ is hydrogen or a group, optionally substituted by one or more, identical or different R$^{b3}$ and/or R$^{c3}$, selected from the group consisting of C$_{1-6}$alkyl, C$_{2-6}$alkenyl, C$_{2-6}$alkynyl, C$_{1-6}$haloalkyl, C$_{3-6}$cycloalkyl, C$_{4-6}$cycloalkenyl, $C_{6-10}$aryl, 5-10 membered heteroaryl and 3-10 membered heterocyclyl; or $R^4$ is selected from the group consisting of —CN, —C(O)$R^{c3}$, —C(O)O$R^{c3}$, —C(O)N$R^{c3}R^{c3}$, —S(O)$_2R^{c3}$ and —S(O)$_2$N$R^{c3}R^{c3}$;

each $R^{b3}$ is independently selected from the group consisting of —O$R^{c3}$, —N$R^{c3}R^{c3}$, halogen, —CN, —C(O)$R^{c3}$, —C(O)O$R^{c3}$, —C(O)N$R^{c3}R^{c3}$, —C(O)N$R^{g3}$O$R^{c3}$, —S(O)$_2R^{c3}$, —S(O)$_2$N$R^{c3}R^{c3}$, —NHC(O)$R^{c3}$ and —N(C$_{1-4}$alkyl)C(O)$R^{c3}$;

each $R^{c3}$ independently of one another denotes hydrogen or a group, optionally substituted by one or more, identical or different $R^{d3}$ and/or $R^{e3}$, selected from the group consisting of $C_{1-6}$alkyl, $C_{2-6}$alkenyl, $C_{2-6}$alkynyl, $C_{1-6}$haloalkyl, $C_{3-6}$cycloalkyl, $C_{4-6}$cycloalkenyl, $C_{6-10}$aryl, 5-10 membered heteroaryl and 3-10 membered heterocyclyl;

each $R^{d3}$ is independently selected from the group consisting of —O$R^{e3}$, —N$R^{e3}$, halogen, —CN, —C(O)$R^{e3}$, —C(O)O$R^{e3}$, —C(O)N$R^{e3}R^{e3}$, —C(O)N$R^{g3}$O$R^{e3}$, —S(O)$_2R^{e3}$, —S(O)$_2$N$R^{e3}R^{e3}$, —NHC(O)$R^{e3}$ and —N(C$_{1-4}$alkyl)C(O)$R^{e3}$;

each $R^{e3}$ independently of one another denotes hydrogen or a group, optionally substituted by one or more, identical or different $R^{f3}$ and/or $R^{g3}$, selected from the group consisting of $C_{1-6}$alkyl, $C_{2-6}$alkenyl, $C_{2-6}$alkynyl, $C_{1-6}$haloalkyl, $C_{3-6}$cycloalkyl, $C_{4-6}$cycloalkenyl, $C_{6-10}$aryl, 5-10 membered heteroaryl and 3-10 membered heterocyclyl;

each $R^{f3}$ is independently selected from the group consisting of —O$R^{g3}$, —N$R^{g3}R^{g3}$, halogen, —CN, —C(O)$R^{g3}$, —C(O)O$R^{g3}$, —C(O)N$R^{g3}R^{g3}$, —C(O)N$R^{g3}$O$R^{g3}$, —S(O)$_2R^{g3}$, —S(O)$_2$N$R^{g3}R^{g3}$, —NHC(O)$R^{g3}$ and —N(C$_{1-4}$alkyl)C(O)$R^{g3}$;

each $R^{g3}$ is independently selected from the group consisting of hydrogen, $C_{1-6}$alkyl, $C_{2-6}$alkenyl, $C_{2-6}$alkynyl, $C_{1-6}$haloalkyl, $C_{3-6}$cycloalkyl, $C_{4-6}$cycloalkenyl, $C_{6-10}$aryl, 5-10 membered heteroaryl and 3-10 membered heterocyclyl;

$R^5$ and $R^6$, each independently, is hydrogen or a group, optionally substituted by one or more, identical or different $R^{b4}$ and/or $R^{c4}$, selected from the group consisting of $C_{1-6}$alkyl, $C_{2-6}$alkenyl, $C_{2-6}$alkynyl, $C_{1-6}$haloalkyl, $C_{3-6}$cycloalkyl, $C_{4-6}$cycloalkenyl, $C_{6-10}$aryl, 5-10 membered heteroaryl and 3-10 membered heterocyclyl;

each $R^{b4}$ is independently selected from the group consisting of —O$R^{c4}$, —N$R^{c4}R^{c4}$, halogen, —CN, —C(O)$R^{c4}$, —C(O)O$R^{c4}$, —C(O)N$R^{c4}R^{c4}$, —C(O)N$R^{g4}R^{c4}$, —S(O)$_2R^{c4}$, —S(O)$_2$N$R^{c4}R^{c4}$, —NHC(O)$R^{c4}$ and —N(C$_{1-4}$alkyl)C(O)$R^{c4}$;

each $R^{c4}$ independently of one another denotes hydrogen or a group, optionally substituted by one or more, identical or different $R^{d4}$ and/or $R^{e4}$, selected from the group consisting of $C_{1-6}$alkyl, $C_{2-6}$alkenyl, $C_{2-6}$alkynyl, $C_{1-6}$haloalkyl, $C_{3-6}$cycloalkyl, $C_{4-6}$cycloalkenyl, $C_{6-10}$aryl, 5-10 membered heteroaryl and 3-10 membered heterocyclyl;

each $R^{d4}$ is independently selected from the group consisting of —O$R^{e4}$, —N$R^{e4}R^{e4}$, halogen, —CN, —C(O)$R^{e4}$, —C(O)O$R^{e4}$, —C(O)N$R^{e4}R^{e4}$, —C(O)N$R^{g4}$O$R^{e4}$, —S(O)$_2R^{e4}$, —S(O)$_2$N$R^{e4}R^{e4}$, —NHC(O)$R^{e4}$ and —N(C$_{1-4}$alkyl)C(O)$R^{e4}$;

each $R^{e4}$ independently of one another denotes hydrogen or a group, optionally substituted by one or more, identical or different $R^{f4}$ and/or $R^{g4}$, selected from the group consisting of $C_{1-6}$alkyl, $C_{2-6}$alkenyl, $C_{2-6}$alkynyl, $C_{1-6}$haloalkyl, $C_{3-6}$cycloalkyl, $C_{4-6}$cycloalkenyl, $C_{6-10}$aryl, 5-10 membered heteroaryl and 3-10 membered heterocyclyl;

each $R^{f4}$ is independently selected from the group consisting of —O$R^{g4}$, —N$R^{g4}R^{g4}$, halogen, —CN, —C(O)$R^{g4}$, —C(O)O$R^{g4}$, —C(O)N$R^{g4}R^{g4}$, —C(O)N$R^{g4}$O$R^{g4}$, —S(O)$_2R^{g4}$, —S(O)$_2$N$R^{g4}R^{g4}$, —NHC(O)$R^{g4}$ and —N(C$_{1-4}$alkyl)C(O)$R^{g4}$;

each $R^{g4}$ is independently selected from the group consisting of hydrogen, $C_{1-6}$alkyl, $C_{2-6}$alkenyl, $C_{2-6}$alkynyl, $C_{1-6}$haloalkyl, $C_{3-6}$cycloalkyl, $C_{4-6}$cycloalkenyl, $C_{6-10}$aryl, 5-10 membered heteroaryl and 3-10 membered heterocyclyl;

each $R^7$ is independently selected from the group consisting of halogen, $C_{1-4}$alkyl, —CN, $C_{1-4}$haloalkyl, —OC$_{1-4}$alkyl and —OC$_{1-4}$haloalkyl;

q denotes the number 0, 1, 2 or 3;

W, X and Y is each independently selected from —N═ and —CH═ with the proviso that the hydrogen in each —CH═ may be replaced by a substituent $R^7$ if present and that a maximum of two of W, X and Y can be —N═;

V is oxygen or sulfur;

n denotes the number 1, 2 or 3;

or a salt thereof.

2. The compound according to claim 1 of formula (Ia)

(Ia)

or a salt thereof.

3. The compound according to claim 1, wherein $R^3$ is hydrogen;

or a salt thereof.

4. The compound according to claim 1, wherein $R^4$ is hydrogen or a group, optionally substituted by one or more, identical or different $R^{b3}$ and/or $R^{c3}$, selected from the group consisting of $C_{1-6}$alkyl, $C_{6-10}$aryl and 5-10 membered heteroaryl; or $R^4$ is selected from the group consisting of —C(O)$R^{c3}$ and —S(O)$_2R^{c3}$;

each $R^{b3}$ is independently selected from the group consisting of —O$R^{c3}$, —N$R^{c3}R^{c3}$ halogen, —CN, —C(O)$R^{c3}$, —C(O)O$R^{c3}$, —C(O)N$R^{c3}R^{c3}$, —C(O)N$R^{c3}$O$R^3$, —S(O)$_2R^{c3}$, —S(O)$_2$N$R^{c3}R^{c3}$, —NHC(O)$R^{c3}$ and —N(C$_{1-4}$alkyl)C(O)$R^{c3}$;

each $R^{c3}$ independently of one another denotes hydrogen or a group, optionally substituted by one or more, identical or different $R^{d3}$ and/or $R^{e3}$, selected from the group consisting of $C_{1-6}$alkyl, $C_{3-6}$cycloalkyl, $C_{6-10}$aryl, 5-10 membered heteroaryl and 3-10 membered heterocyclyl;

each $R^{d3}$ is independently selected from the group consisting of —O$R^{e3}$, —N$R^{e3}R^{e3}$ halogen, —CN, —C(O)$R^{e3}$, —C(O)O$R^{e3}$, —C(O)N$R^{e3}R^{e3}$, —C(O)

$NR^{e3}OR^{e3}$, $-S(O)_2R^{e3}$, $-S(O)_2NR^{e3}R^{e3}$, $-NHC(O)R^{e3}$ and $-N(C_{1-4}alkyl)C(O)R^{e3}$;

each $R^{e3}$ independently of one another is selected from the group consisting of hydrogen, $C_{1-6}$alkyl, $C_{3-6}$cycloalkyl, $C_{6-10}$aryl, 5-10 membered heteroaryl and 3-10 membered heterocyclyl;

or a salt thereof.

5. The compound according to claim 4, wherein $R^4$ is hydrogen;
or a salt thereof.

6. The compound according to claim 1, wherein one of $R^5$ and $R^6$ is hydrogen and the other is hydrogen or a group, optionally substituted by one or more, identical or different $R^{b4}$ and/or $R^{e4}$, selected from the group consisting of $C_{1-6}$alkyl, $C_{6-10}$aryl and 5-10 membered heteroaryl;

each $R^{b4}$ is independently selected from the group consisting of $-OR^{c4}$, $-NR^{c4}R^{c4}$, halogen, $-CN$, $-C(O)R^{c4}$, $-C(O)OR$, $-C(O)NR^{c4}R^{c4}$, $-C(O)NR^{c4}OR^{c4}$, $-S(O)_2R^{c4}$, $-S(O)_2NR^{c4}R^{c4}$, $-NHC(O)R^4$ and $-N(C_{1-4}alkyl)C(O)R^{c4}$;

each $R^{c4}$ independently of one another denotes hydrogen or a group, optionally substituted by one or more, identical or different $R^{d4}$ and/or $R^{e4}$, selected from the group consisting of $C_{1-6}$alkyl, $C_{3-6}$cycloalkyl, $C_{6-10}$aryl, 5-10 membered heteroaryl and 3-10 membered heterocyclyl;

each $R^{d4}$ is independently selected from the group consisting of $-OR^{e4}$, $-NR^{e4}R^{e4}$, halogen, $-CN$, $-C(O)R^{e4}$, $-C(O)OR^{e4}$, $-C(O)NR^{e4}R^{e4}$, $-C(O)NR^{e4}OR^{e4}$, $-S(O)_2R^{e4}$, $-S(O)_2NR^{e4}R^{e4}$, $-NHC(O)R^{e4}$ and $-N(C_{1-4}alkyl)C(O)R^{e4}$;

each $R^{e4}$ independently of one another is selected from the group consisting of hydrogen, $C_{1-6}$alkyl, $C_{3-6}$cycloalkyl, $C_{6-10}$aryl, 5-10 membered heteroaryl and 3-10 membered heterocyclyl;

or a salt thereof.

7. The compound according to claim 1, wherein $R^5$ is hydrogen and $R^6$ is not hydrogen;
or a salt thereof.

8. The compound according to claim 1, wherein $R^5$ and $R^6$ is hydrogen;
or a salt thereof.

9. A pharmaceutical composition comprising a compound according to claim 1, or a pharmaceutically acceptable salt thereof, and pharmaceutically acceptable carrier or excipient.

10. The pharmaceutical composition of claim 9 further comprising at least one other cytostatic or cytotoxic active substance.

11. A method for treating cancer, mediated through the inhibition of the interaction between MDM2 and p53, selected from a group consisting of osteosarcoma, ovarian adenocarcinoma, acute lymphoblastic leukaemia and acute myelogenous leukaemia, the method comprising administering a therapeutically effective amount the compound of formula (I) according to claim 1, or a pharmaceutically acceptable salt thereof, to a patient in need thereof.

12. The method of claim 11, wherein said compound of formula (I) is administered before, after or together with at least one other cytostatic or cytotoxic active substance.

\* \* \* \* \*